(12) United States Patent
Villagra et al.

(10) Patent No.: US 12,024,493 B2
(45) Date of Patent: *Jul. 2, 2024

(54) ISOXAZOLE HYDROXAMIC ACIDS AS HISTONE DEACETYLASE 6 INHIBITORS

(71) Applicants: The George Washington University, A Congressionally Chartered Not-for-Profit Corporation, Washington, DC (US); The Board of Trustees of the University of Illinois, Urbana, IL (US)

(72) Inventors: Alejandro Villagra, Falls Church, VA (US); Alan P. Kozikowski, Chicago, IL (US); Sida Shen, Chicago, IL (US)

(73) Assignees: The George Washington University, A Congressionally Chartered Not-for-Profit Corporation, Washington, DC (US); The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,503

(22) Filed: Feb. 1, 2022

(65) Prior Publication Data

US 2022/0153709 A1 May 19, 2022

Related U.S. Application Data

(63) Continuation of application No. 16/498,651, filed as application No. PCT/US2018/025177 on Mar. 29, 2018, now Pat. No. 11,472,780.

(60) Provisional application No. 62/478,365, filed on Mar. 29, 2017.

(51) Int. Cl.

| | |
|---|---|
| *C07D 261/18* | (2006.01) |
| *A61K 45/06* | (2006.01) |
| *A61P 35/00* | (2006.01) |
| *C07D 413/06* | (2006.01) |
| *C07D 417/06* | (2006.01) |
| *C07D 471/04* | (2006.01) |

(52) U.S. Cl.
CPC ............ *C07D 261/18* (2013.01); *A61P 35/00* (2018.01); *C07D 413/06* (2013.01); *C07D 417/06* (2013.01); *C07D 471/04* (2013.01); *A61K 45/06* (2013.01)

(58) Field of Classification Search
CPC .. C07D 261/18; C07D 413/06; C07D 417/06; C07D 471/04; A61P 35/00
See application file for complete search history.

(56) References Cited

U.S. PATENT DOCUMENTS

| | | |
|---|---|---|
| 9,382,197 B2 | 7/2016 | Blackburn et al. |
| 10,836,733 B2 | 11/2020 | Kozikowski et al. |
| 2015/0344466 A1 | 12/2015 | Mitsudera et al. |

FOREIGN PATENT DOCUMENTS

| | | |
|---|---|---|
| WO | WO-2003050261 A2 | 6/2003 |
| WO | WO-2003060523 A1 | 7/2003 |
| WO | WO-2008055068 A2 | 5/2008 |
| WO | WO-2017040564 A1 | 3/2017 |
| WO | WO-2018183701 A1 | 10/2018 |

OTHER PUBLICATIONS

Andrews, K.T., et al., "Potent antimalarial activity of histone deacetylase inhibitor analogues," *Antimicrob Agents Chemother* 52(4):1454-61, American Society for Microbiology, United States (Apr. 2008).

Barlev, N.A., et al., "Acetylation of p53 Activates Transcription Through Recruitment of coactivators/histone Acetyltransferases," *Mol. Cell* 8(6):1243-1254, American Society for Microbiology, United States (Dec. 2001).

Bingham, A.L., et al., "Over one hundred solvates of sulfathiazole," *Chem Commun* (7): 603-604, Royal Society of Chemistry, United Kingdom (Mar. 2001).

Bradley, M.O., et al., "Tumor Targeting by Covalent Conjugation of a Natural Fatty Acid to Paclitaxel," *Clinical Cancer Research* 7(10):3229-3238, The American Association for Cancer Research, United States (Oct. 2001).

Caira, M,R., et al., "Preparation and Crystal Characterization of a Polymorph, a Monohydrate, and an Ethyl Acetate Solvate of the Antifungal Fluconazole," *Journal of Pharmaceutical Sciences* 93(3):601-611, American Pharmaceutical Assn, United States (Mar. 2004).

Gu, W., et al., "Activation of p53 Sequence-Specific DNA Binding by Acetylation of the p53 C-terminal Domain," *Cell* 90(4):595-606, Cell Press, United States (Aug. 1997).

(Continued)

*Primary Examiner* — Alicia L Otton
(74) *Attorney, Agent, or Firm* — Sterne, Kessler, Goldstein & Fox P.L.L.C.

(57) ABSTRACT

The present disclosure provides compounds represented by Formula I:

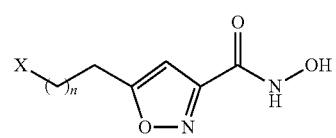

and pharmaceutically acceptable salts, solvates, e.g., hydrates, and prodrugs thereof, wherein X and n are as defined as set forth in the specification. The present disclosure also provides compounds of Formula I for use to treat diseases and conditions, e.g., cancer, wherein inhibition of HDAC provides a benefit.

15 Claims, 18 Drawing Sheets

(56) References Cited

OTHER PUBLICATIONS

Herrmann, K., and Niedobitek, G., "Epstein-Barr Virus-Associated Carcinomas: Facts and Fiction," *Journal of Pathology* 199(2):140-145, John Wiley And Sons, United Kingdom (Feb. 2003).
Hillgren, K.M., et al., "In Vitro Systems for Studying Intestinal Drug Absorption," *Medicinal Research Reviews* 15(2):83-109, Wiley, United states (Mar. 1995).
International Search Report and Written Opinion for Application No. PCT/US2018/025177, dated Aug. 1, 2018, 10 pages.
Ito, A., et al., "p300/CBP-mediated p53 acetylation is commonly induced by p53-activating agents and inhibited by MDM2," *EMBO Journal* 20(6): 1331-1340, EMBO Press, Germany (Mar. 2001).
Ito, A., et al., "MDM2-HDAC1-mediated Deacetylation of p53 Is Required for Its Degradation," *EMBO* 21(22):6236-6245, EMBO Press, Germany (Nov. 2002).
Liu, L., et al., "P53 Sites Acetylated in Vitro by PCAF and p300 Are Acetylated in Vivo in Response to DNA Damage," *Mol Cell Biol* 19(2):1202-1209, American Society for Microbiology, United States (Feb. 1999).
Mortreux, F., et al., "Molecular and Cellular Aspects of HTLV-1 Associated Leukemogenesis in Vivo," *Leukemia* 17(1):26-38, Williams & Wilkins, United Kingdom (Jan. 2003).
Sakaguchi, K., et al., "DNA Damage Activates p53 Through a Phosphorylation-Acetylation Cascade," *Genes Dev.* 12(18):2831-2841, Cold Spring Harbor Press, United States (Sep. 1998).
Silverman, "Prodrugs and Drug Delivery Systems," Chapter 8, The Organic Chemistry of Drug Design and Drug Action, Academic Press, pp. 352-401, 1992.
Tapadar, S., et al., "Isoxazole moiety in the linker region of HDAC inhibitors adjacent to the Zn-chelating group: Effects on HDAC biology and antiproliferative activity," *Bioorganic & Medicinal Chemistry Letters* 19(11):3023-3026, Elsevier, Netherlands (Jun. 2009).
Tao, R., et al., "Deacetylase Inhibition Promotes the Generation and Function of Regulatory T Cells," *Nature Medicine* 13(11):1299-1307, Nature Publishing Company, United States (Nov. 2007).
Van Tonder, E.C., et al., "Preparation and Physicochemical Characterization of 5 Niclosamide Solvates and 1 Hemisolvate," *AAPS PharmSciTech* 5(1):E12, American Association of Pharmaceutical Scientists, United States (Feb. 2004).
Abel, T. and Zukin, R. S., "Epigenetic targets of HDAC inhibition in neurodegenerative and psychiatric disorders," *Curr Opin Pharmacol.* 8(1):57-64, National Institute of Health, United States (2008).
Baltan, S., et al., "Novel Protective effects ofHistone Deacetylase Inhibition on Stroke and White Matter Ischemic Injury," *Neurotherapeutics* 10:798-807, The American Society for Experimental Neuro Therapeutics, Inc., United States (2013).
Bergman, J.A., et al., "Selective histone deacetylase 6 inhibitors bearing substituted urea linkers inhibit melanoma cell growth," *Journal of Medicinal Chemistry* 55(22):9891-9899, American Chemical Society, United States (2012).
Butler, K.V., et al., "Rational design and simple chemistry yield a superior, neuroprotective HDAC6 inhibitor, tubastatin A," *Journal of the American Chemical Society* 132(31):10842-10846, American Chemical Society, United States (2010).
Conti, P., et al., "Design and synthesis of novel isoxazole-based HDAC inhibitors," *European Journal of Medicinal Chemistry* 45:4331-4338, Elsevier Masson SAS, France (2010).
Didonna, A. and Opal, P., "The promise and perils of HDAC inhibitors in neurodegeneration," *Annals of Clinical and Translational Neurology* 2(1):79-101, John Wiley & Sons, Inc., United States (2015).

Dow, G.S., et al., "Antimalarial activity of phenylthiazolyl-bearing hydroxamate-based histone deacetylase inhibitors," *Antimicrobial Agents and Chemotherapy* 52(10):3467-3477, American Society for Microbiology, United States (2008).
Extended European Search Report for EP Application No. EP 18776871, Munich, Germany, dated Mar. 5, 2021, 11 pages.
Gaisina, I.N., et al., "Identification of HDAC6-Selective Inhibitors of Low Cancer Cell Cytotoxicity," *ChemMedChem* 11:81-92, John Wiley and Sons Ltd, United Kingdom (2016).
Huang, P., et al., "Selective HDAC inhibition by ACY-241 enhances the activity of paclitaxel in solid tumor models," *Oncotarget* 8(2):2694-2707, Impact Journals LLC, United States (2017).
Jochems, J., et al., "Antidepressant-like properties of novel HDAC6-selective inhibitors with improved brain bioavailability," *Neuropsychopharmacology* 39(2):389-400, Nature Publishing Group, United Kingdom (2014).
Lu, J., et al., "Histone deacetylase inhibitors ae neuroprotective and preserve NGF-mediated cell survival following traumatic brain injury," *PNAS* 110(26): 10747-10752, United States National Academy of Sciences, United States (2013).
Machado-Vieira, R., et al., "Histone Deacetylases and Mood Disorders: Epigenetic Programming in Gene-environment Interactions," *CNS Neuroscience & Therapeutics* 17:699-704, Blackwell Publishing Ltd., United States (2011).
Mithraprabhu, S., et al., "Histone deacetylase (HDAC) inhibitors as single agents induce multiple myeloma cell death principally through the inhibition of class I HDAC," *British Journal of Haematology* 162(4):559-62, John Wiley & Son Ltd., United Kingdom (2013).
Ren, J., et al., "Selective HDAC6 inhibition decreases early stage of lupus nephritis by down-regulating both innate and adaptive immune responses," *Clinical and Experimental Immunology* 191(1):19-31, Wiley-Blackwell Publishing Ltd, United Kingdom (2018).
Saito, S., et al., "Tubastatin ameliorates pulmonary fibrosis by targeting the TGF-PBK-Akt pathway," *PLoS One* 12(10):e0186615, Public Library of Science, United States (2017).
Santo, L., et al., "Preclinical activity, pharmacodynamic, and pharmacokinetic properties of a selective HDAC6 inhibitor, ACY-1215, in combination with bortezomib in multiple myeloma," *Blood* 119(11):2579-89, American Society of Hematology, United States (2012).
Shen, S. and Kozikowski, A.P., "A patent review of histone deacetylase 6 inhibitors in neurodegenerative diseases (2014-2019)," *Expert Opinion on Therapeutic Patents* 30(2):121-136, Taylor and Francis Ltd., United Kingdom (2020).
Shen, S., et al., "Discovery of a New Isoxazole-3-hydroxamate-Based Histone Deacetylase 6 Inhibitor SS-208 with Antitumor Activity in Syngeneic Melanoma Mouse Models," *Journal of Medicinal Chemistry* 62(18):8557-8577, American Chemical Society, United States (2019).
Supplementary European Search Report for EP Application No. EP 18, 77 6871, Munich, Germany, dated Dec. 2, 2020, 15 pages.
Tang, J., et al., "Histone deacetylases as targets for treatment of multiple diseases," *Clin Sci (Land)* 124(11):651-662, National Institute of Health, United States (2013).
Volmar, C-H., and Wahlestedt, C., "Histone deacetylases (HDACs) and brain function," *Neuroepigenetics* 1:20-27, Elsevier, Netherlands (2015).
Yang, F., et al., "Next-generation of selective histone deacetylase inhibitors," *RSC Advances* 9:19571-19583, Royal Society of Chemistry, United Kingdom (2019).
Qvortrup, K., et al., "In-bead screening of hydroxamic acids for the identification of HDAC inhibitors," *Angew Chem Int Ed Engl* 55(14):4472-5, Wiley-VCH, Germany (Mar. 2016).
Andrews, K.T., et al., "Anti-malarial Effect of Histone Deacetylation Inhibitors and Mammalian Tumour Cytodifferentiating Agents," *International Journal for Parasitology* 30(6):761-768, Elsevier Science, United Kingdom (May 2000).

ISOXAZOLE HYDROXAMIC ACIDS AS HISTONE DEACETYLASE 6 INHIBITORS

STATEMENT OF GOVERNMENTAL INTEREST

This invention was made with government support under grant number 5R01NS079183 awarded by the National Institutes of Health. The government has certain rights in this invention.

TECHNICAL FIELD

This disclosure relates to isoxazole-substituted hydroxamic acid HDAC inhibitors (HDACIs), pharmaceutical compositions comprising HDACIs, and methods of treating diseases and conditions, e.g., cancer, wherein inhibition of HDAC provides a benefit.

BACKGROUND OF THE INVENTION

Covalent post-translational modifications (PTMs) of epigenomic proteins contribute to their biological roles, and thus serve as carriers of epigenetic information from one cell generation to the next. Epigenetics means on top of or above genetics, and refers to external modifications to DNA and associated histones that turn genes "on" or "off." These modifications do not change the DNA sequence, but instead, they affect how cells "read" genes. PTMs play key roles in the regulation of protein function, transcription, DNA replication, and repair of DNA damage.

The major events surrounding epigenetic control are focused on three modes of action: writers, readers, and erasers. The writers are responsible for adding a variety of PTM marks to histones which include, inter alia, acetylation which is catalyzed by histone acetyltransferases (HATs). Readers refer to the proteins that recognize and bind to these PTM marks thereby mediating their effects, and erasers encompass various enzymes such as the histone deacetylases (HDACs) that catalyze the removal of these marks. In the case of acetylated histone lysine residues, HDACs are responsible for catalyzing the hydrolysis of the acetyl mark to provide the unsubstituted lysine residue. The HDAC family consists of at present 18 enzymes which are classified into four subgroups according to their homology to the yeast family. HDAC1, 2, 3 and 8—categorized as class I HDACs according to their homology with yeast Rpd3—are characterized by ubiquitous expression and localization to the nucleus. Class II HDACs show tissue-specific expression and shuttle between the nucleus and cytoplasm. Homologous to yeast Hda1, these enzymes are subdivided in class IIa (HDAC4, 5, 7 and 9) and class IIb (HDAC6 and 10). HDAC11, the only member of the class IV subfamily, shows similarities to the catalytic domains of both class I and II enzymes. Class I, II, and IV HDACs require $Zn^{2+}$ as a cofactor of the deacetylating activity and are also referred to as the conventional HDACs. The sirtuins 1-7 are dependent on nicotinamide adenine dinucleotide for their activity and form class III of the HDACs.

Pharmacologic manipulation of the enzymes involved in regulating protein PTMs, especially those tied to very specific PTM marks, holds tremendous possibilities in better understanding the workings of the cell. The discovery of selective small molecule modulators of these enzymes would provide chemical tools to better understand the role of these PTMs at the cellular level, but may also lead to important disease modifiers. Within the HDAC field, there exists a plethora of compounds that are able to block the deacetylase enzymes, and several have made their way to the marketplace for cancer therapy. The majority of these HDACIs, however, are not very isoform selective. Many of them inhibit across more than one class of HDAC enzymes and are thus labeled pan-selective. Of the various HDAC isoforms that appear to be promising therapeutic targets for treating humans diseases such as cancer and certain CNS disorders, HDAC6 has emerged as a particularly attractive target, especially in view of the fact that HDAC6 knockout animals remain viable. HDAC6 has no apparent role in the PTM of histone proteins, but rather is involved in regulating the acetylation status of α-tubulin, HSP-90, cortactin, HSF-1, and other protein targets. This enzyme also plays a role in the recognition and clearance of polyubiquitinated misfolded proteins from the cell through aggresome formation.

HDACIs are disclosed in WO 2017/040564. There is an ongoing need for new agents, e.g., small molecules, for treating and/or preventing cancer and other diseases responsive to inhibition of HDAC.

SUMMARY OF THE INVENTION

In one aspect, the present disclosure provides compounds having any one of Formulae I-V, below, and the pharmaceutically acceptable salts, solvates, e.g., hydrates, and prodrugs thereof, collectively referred to as "Compounds of the Disclosure." Compounds of the Disclosure are histone deacetylase inhibitors.

In one aspect, the present disclosure provides compounds having any one of Formulae VI-X, below, collectively referred to as "Intermediates of the Disclosure." Intermediates of the Disclosure are synthetic intermediates that can be used to prepare histone deacetylase inhibitors having Formulae I-V.

In another aspect, the present disclosure provides methods of treating diseases and conditions wherein inhibition of HDAC provides a benefit, e.g., cancer, a neurological disease, a psychiatric illness, a neurodegenerative disorder, a peripheral neuropathy, stroke, hypertension, an inflammation, traumatic brain injury, rheumatoid arthritis, allograft rejection, or autoimmune disease, the method comprising administering a therapeutically effective amount of a Compound of the Disclosure to an individual, e.g., a human patient, in need thereof.

In another aspect, the present disclosure provides methods of treating diseases and conditions such as a cancer, a neurological disease, a psychiatric illness, a neurodegenerative disorder, a peripheral neuropathy, stroke, hypertension, an inflammation, traumatic brain injury, rheumatoid arthritis, allograft rejection, and autoimmune diseases, the method comprising administering a therapeutically effective amount of a Compound of the Disclosure to an individual in need thereof.

In another aspect, the present disclosure provides a method of increasing the sensitivity of a cancer cell to radiotherapy and/or chemotherapy, the method comprising administering a therapeutically effective amount of a Compound of the Disclosure to an individual in need thereof.

In another aspect, the present disclosure provides for the use of Compounds of the Disclosure in combination with other drugs and/or therapeutic approaches.

In another aspect, the present disclosure provides Compounds of the Disclosure that exhibit selectivity for particular HDAC isozymes, such as HDAC6, over other HDAC isozymes.

In another aspect, the present disclosure provides a Compound of the Disclosure for use in treatment of a disease or condition of interest, e.g., a cancer, a neurological disease, a psychiatric illness, a neurodegenerative disorder, a peripheral neuropathy, stroke, hypertension, an inflammation, traumatic brain injury, rheumatoid arthritis, allograft rejection, and autoimmune diseases.

In another aspect, the present disclosure provides a use of a Compound of the Disclosure for the manufacture of a medicament for treating a disease or condition of interest, e.g., a cancer, a neurological disease, a psychiatric illness, a neurodegenerative disorder, a peripheral neuropathy, stroke, hypertension, an inflammation, traumatic brain injury, rheumatoid arthritis, allograft rejection, and autoimmune diseases.

In another aspect, the present disclosure provides a kit comprising a Compound of the Disclosure and, optionally, a packaged composition comprising a second therapeutic agent useful in the treatment of a disease or condition of interest, and a package insert containing directions for use in the treatment of a disease or condition, e.g., a cancer, a neurological disease, a psychiatric illness, a neurodegenerative disorder, a peripheral neuropathy, stroke, hypertension, an inflammation, traumatic brain injury, rheumatoid arthritis, allograft rejection, and autoimmune diseases.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Figure 1:
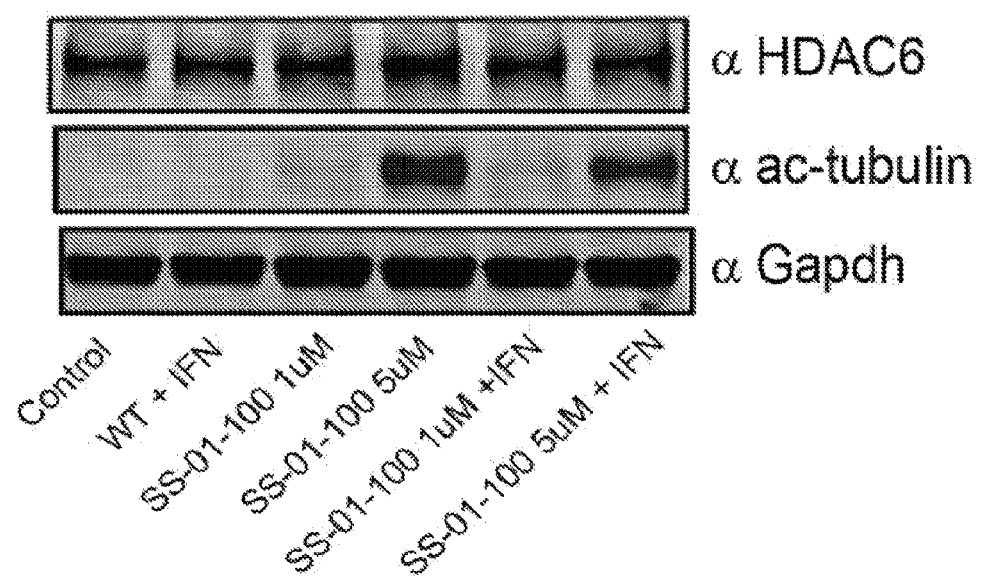
FIG. 1 is an immunoblot illustration showing the activity of SS-01-100 in WM164 human melanoma cell lines in the presence or absence of IFNg.

In one embodiment, the present disclosure provides HDACIs having Formula I:

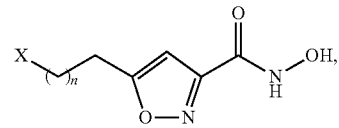

and the pharmaceutically acceptable salts, solvates, and prodrugs thereof, wherein:

X is selected from the group consisting of:

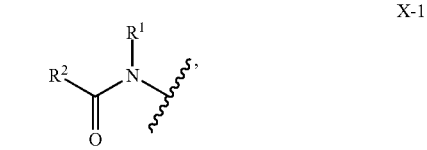

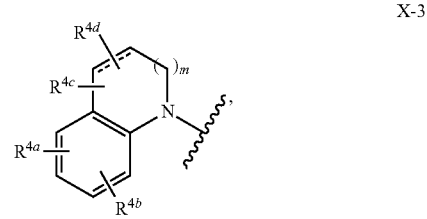

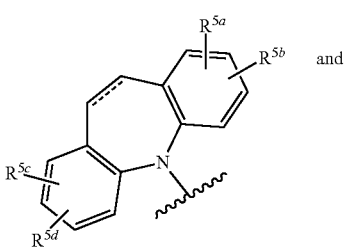

X-4

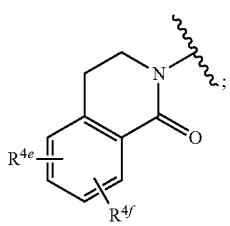

X-5

R¹ is selected from the group consisting of hydrogen and C1-C4 alkyl;

R2 is selected from the group consisting of optionally substituted C6-C14 aryl and aralkyl;

R3 is selected from the group consisting of optionally substituted C6-C14 aryl, optionally substituted 5- to 14-membered heteroaryl, and —C(=O)NR$^d$R$^e$;

$R^{4a}$, $R^{4b}$, $R^{4e}$, and $R^{4f}$ are independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

$R^{4c}$ and $R^{4d}$ are independently selected from the group consisting of hydrogen and $C_{1-4}$ alkyl; or $R^{4c}$ and $R^{4d}$ taken together form a —C(=O)— with the carbon atom to which they are attached;

$R^{5a}$, $R^{5b}$, $R^{5c}$, and $R^{5d}$ are independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

Z is selected from the group consisting of —O—, —N(R$^8$)—, and —C(=O)—; or

Z is absent;

R$^8$ is selected from the group consisting of hydrogen, $C_{1-4}$ alkyl, optionally substituted $C_{3-6}$ cycloalkyl, optionally substituted $C_6$-$C_{14}$ aryl, aralkyl, optionally substituted 5- to 14-membered heteroaryl, and heteroaralkyl;

m is 0, 1, or 2;

n is 1, 2, 3, 4, 5, or 6;

==== represents a single or double bond;

R$^a$, R$^b$, R$^d$, and R$^e$ are independently selected from the group consisting of hydrogen, $C_{1-6}$ alkyl, optionally substituted $C_{3-6}$ cycloalkyl, optionally substituted $C_6$-$C_{14}$ aryl, optionally substituted 5- to 14-membered heteroaryl; or R$^a$ and R$^b$ taken together with the nitrogen atom to which they are attached form an optionally substituted 3- to 12-membered heterocyclo;

R$^d$ and R$^e$ taken together with the nitrogen atom to which they are attached form an optionally substituted 3- to 12-membered heterocyclo; and R$^c$ is $C_{1-4}$ alkyl.

In another embodiment, the present disclosure provides HDACIs having Formula I, and the pharmaceutically acceptable salts, solvates, and prodrugs thereof, with the proviso that when Z is absent, R³ is a bicyclic or tricyclic $C_{10-14}$ aryl, a bicyclic or tricyclic 9- to 14-membered heteroaryl, or —C(=O)NR$^d$R$^e$.

In one embodiment, the present disclosure provides HDACIs having Formula I, and the pharmaceutically acceptable salts, solvates, and prodrugs thereof, wherein X is X-1, X-2, X-3, or X-4;

Z is —O—;

R¹ is selected from the group consisting of hydrogen and $C_{1-4}$ alkyl;

R² is optionally substituted $C_6$-$C_{14}$ aryl;

R³ is selected from the group consisting of optionally substituted $C_6$-$C_{14}$ aryl and optionally substituted 5- to 14-membered heteroaryl;

$R^{4a}$ and $R^{4b}$ are independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

$R^{4c}$ and $R^{4d}$ are independently selected from the group consisting of hydrogen and $C_{1-4}$ alkyl;

$R^{5a}$, $R^{5b}$, $R^{5c}$, and $R^{5d}$ are independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

R$^a$ and R$^b$ are independently selected from the group consisting of hydrogen and $C_{1-6}$ alkyl; or R$^a$ and R$^b$ taken together with the nitrogen atom to which they are attached form a 3- to 7-membered heterocyclo; and R$^c$ is $C_{1-4}$ alkyl.

In another embodiment, the present disclosure provides HDACIs having Formula I, and the pharmaceutically acceptable salts, solvates, e.g., hydrates, and prodrugs thereof, wherein X is X-1. In another embodiment, R¹ is hydrogen. In another embodiment, R² is optionally substituted phenyl. In another embodiment, R² is optionally substituted 1-naphthyl. In another embodiment, R² is optionally substituted 2-naphthyl. In another embodiment, R² is aralkyl.

In another embodiment, the present disclosure provides HDACIs having Formula I, and the pharmaceutically acceptable salts, solvates, e.g., hydrates, and prodrugs thereof, wherein X is X-2. In another embodiment, Z is —O—. In another embodiment, Z is —N(R$^8$)— In another embodiment, Z is —C(=O)—. In another embodiment, R³ is optionally substituted $C_6$-$C_{14}$ aryl. In another embodiment, R³ is optionally substituted 5- to 14-membered heteroaryl. In another embodiment, R³ is —C(=O)NR$^d$R$^e$. In another embodiment, Z is absent and R³ is a bicyclic or tricyclic $C_{10-14}$ aryl, a bicyclic or tricyclic 9- to 14-membered heteroaryl, or —C(=O)NR$^d$R$^e$.

In another embodiment, the present disclosure provides HDACIs having Formula I, and the pharmaceutically acceptable salts, solvates, e.g., hydrates, and prodrugs thereof, wherein X is X-3.

In another embodiment, the present disclosure provides HDACIs having Formula I, and the pharmaceutically acceptable salts, solvates, e.g., hydrates, and prodrugs thereof, wherein X is X-4.

In another embodiment, the present disclosure provides HDACIs having Formula I, and the pharmaceutically acceptable salts, solvates, e.g., hydrates, and prodrugs thereof, wherein X is X-5.

In another embodiment, the present disclosure provides HDACIs having Formula II:

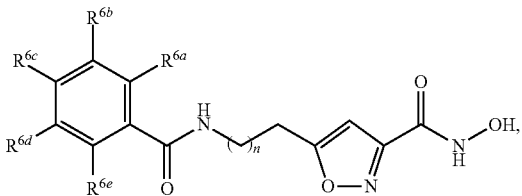

II and the pharmaceutically acceptable salts, solvates, e.g., hydrates, and prodrugs thereof, wherein:

$R^{6a}$, $R^{6b}$, $R^{6c}$, $R^{6d}$, an $R^{6e}$ are each independently selected from the group consisting of hydrogen, halogen, hydroxy, nitro, cyano, —$NR^aR^b$, —C(=O)$NR^aR^b$, —C(=O)$R^c$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-6}$ cycloalkyl, optionally substituted phenyl, optionally substituted 5- or 6-membered heteroaryl, and optionally substituted 5- or 6-membered heterocyclo;

$R^a$ and $R^b$ are independently selected from the group consisting of hydrogen and $C_{1-4}$ alkyl; or $R^a$ and $R^b$ taken together with the nitrogen atom to which they are attached form a 3- to 7-membered heterocyclo;

$R^c$ is $C_{1-4}$ alkyl; and n is 1, 2, or 3.

In another embodiment, the present disclosure provides HDACIs having Formula II, and the pharmaceutically acceptable salts, solvates, e.g., hydrates, and prodrugs thereof, wherein $R^{6a}$, $R^{6b}$, $R^{6c}$, $R^{6d}$, and $R^{6e}$ are each independently selected from the group consisting of hydrogen, halogen, hydroxy, nitro, cyano, —$NR^aR^b$, —C(=O)$NR^aR^b$, —C(=O)$R^c$, $C_{1-4}$ alkyl, $C_{1-4}$ alkoxy, and $C_{1-4}$ haloalkyl. In another embodiment, $R^{6a}$, $R^{6b}$, $R^{6c}$, $R^{6d}$, and $R^{6e}$ are each independently selected from the group consisting of hydrogen, halogen, cyano, $C_{1-4}$ alkyl, and $C_{1-4}$ alkoxy.

In another embodiment, the present disclosure provides HDACIs having Formula II, and the pharmaceutically acceptable salts, solvates, e.g., hydrates, and prodrugs thereof, wherein n is 1. In another embodiment, n is 2. In another embodiment, n is 3.

In another embodiment, the present disclosure provides HDACIs having Formula III:

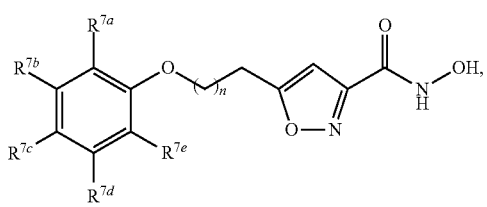

III and the pharmaceutically acceptable salts, solvates, e.g., hydrates, and prodrugs thereof, wherein:

$R^{7a}$, $R^{7b}$, $R^{7c}$, $R^{7d}$, and $R^{7e}$ are each independently selected from the group consisting of hydrogen, halogen, hydroxy, nitro, cyano, —$NR^aR^b$, —C(=O)$NR^aR^b$, —C(=O)$R^c$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-6}$ cycloalkyl, optionally substituted phenyl, optionally substituted 5- or 6-membered heteroaryl, and optionally substituted 5- or 6-membered heterocyclo;

$R^a$ and $R^b$ are independently selected from the group consisting of hydrogen and $C_{1-4}$ alkyl; or $R^a$ and $R^b$ taken together with the nitrogen atom to which they are attached form a 3- to 7-membered heterocyclo;

$R^c$ is $C_{1-4}$ alkyl; and n is 1, 2, or 3.

In another embodiment, the present disclosure provides HDACIs having Formula III, and the pharmaceutically acceptable salts, solvates, e.g., hydrates, and prodrugs thereof, wherein $R^{7a}$, $R^{7b}$, $R^{7c}$, $R^{7d}$, and $R^{7e}$ are each independently selected from the group consisting of hydrogen, halogen, hydroxy, nitro, cyano, —$NR^aR^b$, —C(=O)$NR^aR^b$, —C(=O)$R^c$, $C_{1-4}$ alkyl, $C_{1-4}$ alkoxy, and $C_{1-4}$ haloalkyl. In another embodiment, $R^{7a}$, $R^{7b}$, $R^{7c}$, $R^{7d}$, and $R^{7e}$ are each independently selected from the group consisting of hydrogen, halogen, cyano, $C_{1-4}$ alkyl, and $C_{1-4}$ alkoxy.

In another embodiment, the present disclosure provides HDACIs having Formula III, and the pharmaceutically acceptable salts, solvates, e.g., hydrates, and prodrugs thereof, wherein n is 1. In another embodiment, n is 2. In another embodiment, n is 3.

In another embodiment, the present disclosure provides HDACIs having Formula IV:

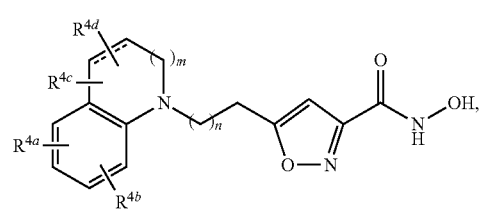

IV and the pharmaceutically acceptable salts, solvates, e.g., hydrates, and prodrugs thereof, wherein:

$R^{4a}$ and $R^{ob}$ are independently selected from the group consisting of hydrogen, halogen, cyano, $C_{1-4}$ alkyl, and $C_{1-4}$ alkoxy;

$R^{4c}$ and $R^{4d}$ are independently selected from the group consisting of hydrogen and methyl;

m is 0 or 1;

n is 1, 2, or 3; and

==== represents a single or double bond.

In another embodiment, the present disclosure provides HDACIs having Formula IV, and the pharmaceutically acceptable salts, solvates, e.g., hydrates, and prodrugs thereof, wherein m is 0 and ==== represents a double bond.

In another embodiment, the present disclosure provides HDACIs having Formula IV, and the pharmaceutically acceptable salts, solvates, e.g., hydrates, and prodrugs thereof, wherein m is 1 and ==== represents a single bond.

In another embodiment, the present disclosure provides HDACIs having Formula IV, and the pharmaceutically acceptable salts, solvates, e.g., hydrates, and prodrugs thereof, wherein n is 1. In another embodiment, n is 2. In another embodiment, n is 3.

In another embodiment, the present disclosure provides HDACIs having Formula V:

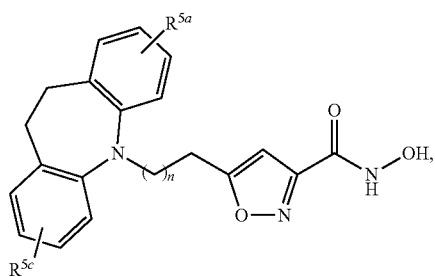

and the pharmaceutically acceptable salts, solvates, e.g., hydrates, and prodrugs thereof, wherein:

$R^{5a}$ and $R^{5c}$ are independently selected from the group consisting of hydrogen, halogen, cyano, $C_{1-4}$ alkyl, and $C_{1-4}$ alkoxy; and n is 1, 2, or 3.

In another embodiment, the present disclosure provides HDACIs having Formula V, and the pharmaceutically acceptable salts, solvates, e.g., hydrates, and prodrugs thereof, wherein n is 1. In another embodiment, n is 2. In another embodiment, n is 3.

In another embodiment, Compounds of the Disclosure are any one or more of the compounds having Formula I of Table 1, and the pharmaceutically acceptable salts, solvates, e.g., hydrates, and prodrugs thereof.

TABLE 1

| Structure | Name |
|---|---|
| 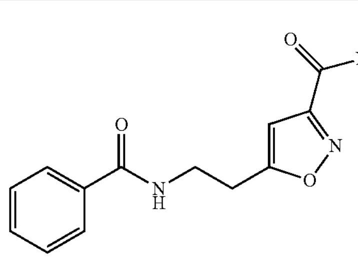 | 5-(2-benzamidoethyl)-N-hydroxyisoxazole-3-carboxamide |
| 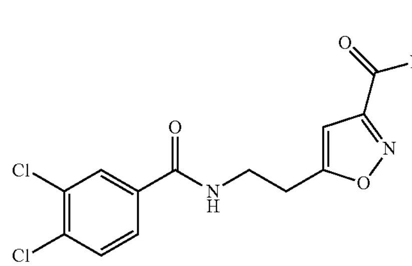 | 5-(2-(3,4-dichlorobenzamido)ethyl)-N-hydroxyisoxazole-3-carboxamide |
| 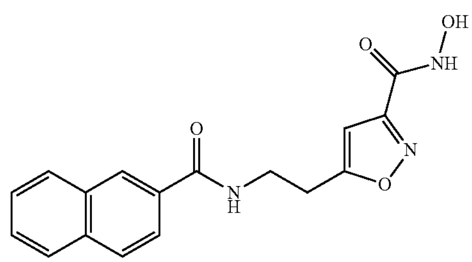 [SMILES: O=C(NCCc1cc(C(=O)NO)no1)c1ccc2ccccc2c1] | 5-(2-(2-naphthamido)ethyl)-N-hydroxyisoxazole-3-carboxamide |
| 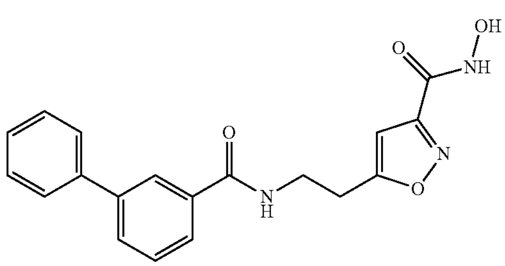 [SMILES: O=C(NCCc1cc(C(=O)NO)no1)c1cccc(-c2ccccc2)c1] | 5-(2-([1,1'-biphenyl]-3-carboxamido)ethyl)-N-hydroxyisoxazole-3-carboxamide |
| 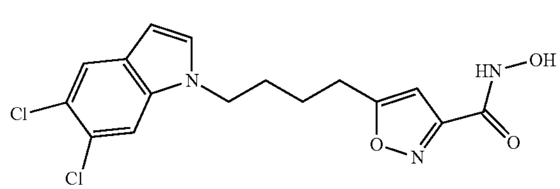 [SMILES: O=C(NO)c1cc(CCCCn2ccc3cc(Cl)c(Cl)cc32)on1] | 5-(4-(5,6-dichloro-1H-indol-1-yl)butyl)-N-hydroxyisoxazole-3-carboxamide |

TABLE 1-continued

| Structure | Name |
|---|---|
| 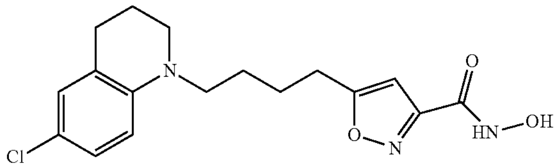 [SMILES: O=C(NO)c1cc(CCCCN2CCCc3cc(Cl)ccc32)on1] | 5-(4-(6-chloro-3,4-dihydroquinolin-1(2H)-yl)butyl)-N-hydroxyisoxazole-3-carboxamide |
| 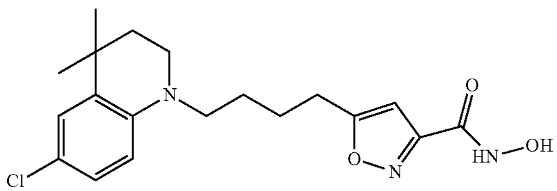 [SMILES: CC1(C)CCN(CCCCc2cc(C(=O)NO)no2)c2ccc(Cl)cc21] | 5-(4-(6-chloro-4,4-dimethyl-3,4-dihydroquinolin-1(2H)-yl)butyl)-N-hydroxyisoxazole-3-carboxamide |
| 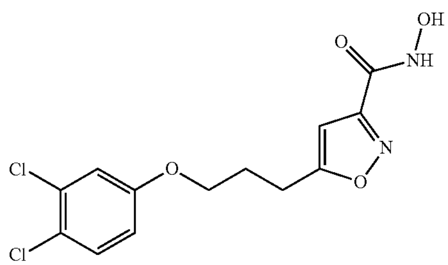 [SMILES: O=C(NO)c1cc(CCCOc2ccc(Cl)c(Cl)c2)on1] | 5-(3-(3,4-dichlorophenoxy)propyl)-N-hydroxyisoxazole-3-carboxamide |
| 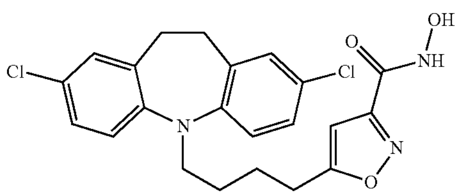 [SMILES: O=C(NO)c1cc(CCCCN2c3ccc(Cl)cc3CCc3cc(Cl)ccc32)on1] | 5-(4-(2,8-dichloro-10,11-dihydro-5H-dibenzo[b,f]azepin-5-yl)butyl)-N-hydroxyisoxazole-3-carboxamide |
| 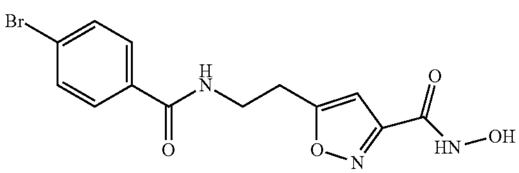 | 5-(2-(4-bromobenzamido)ethyl)-N-hydroxyisoxazole-3-carboxamide |
| 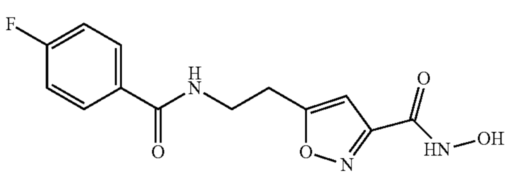 [SMILES: O=C(NCCc1cc(C(=O)NO)no1)c1ccc(F)cc1] | 5-(2-(4-fluorobenzamido)ethyl)-N-hydroxyisoxazole-3-carboxamide |
| 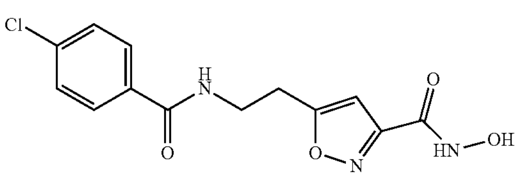 [SMILES: O=C(NCCc1cc(C(=O)NO)no1)c1ccc(Cl)cc1] | 5-(2-(4-chlorobenzamido)ethyl)-N-hydroxyisoxazole-3-carboxamide |
| 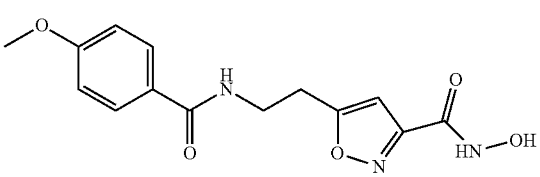 [SMILES: COc1ccc(C(=O)NCCc2cc(C(=O)NO)no2)cc1] | N-hydroxy-5-(2-(4-methoxybenzamido)ethyl)isoxazole-3-carboxamide |

TABLE 1-continued

| | |
|---|---|
| 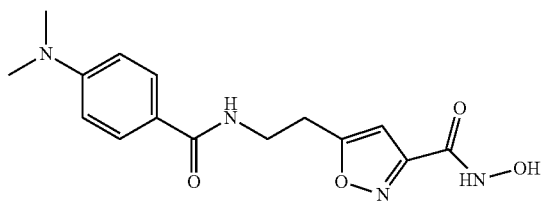 [SMILES: CN(C)c1ccc(C(=O)NCCc2cc(C(=O)NO)no2)cc1] | 5-(2-(4-(dimethylamino)benzamido)ethyl)-N-hydroxyisoxazole-3-carboxamide |
| 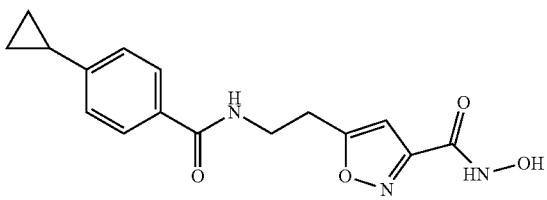 [SMILES: O=C(NCCc1cc(C(=O)NO)no1)c1ccc(C2CC2)cc1] | 5-(2-(4-cyclopropylbenzamido)ethyl)-N-hydroxyisoxazole-3-carboxamide |
| 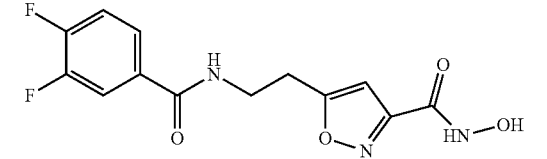 [SMILES: O=C(NCCc1cc(C(=O)NO)no1)c1ccc(F)c(F)c1] | 5-(2-(3,4-difluorobenzamido)ethyl)-N-hydroxyisoxazole-3-carboxamide |
| 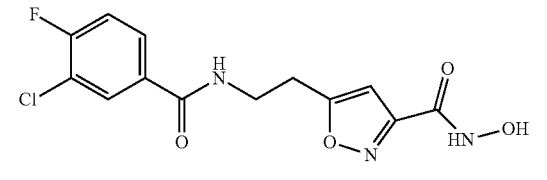 [SMILES: O=C(NCCc1cc(C(=O)NO)no1)c1ccc(F)c(Cl)c1] | 5-(2-(3-chloro-4-fluorobenzamido)ethyl)-N-hydroxyisoxazole-3-carboxamide |
| 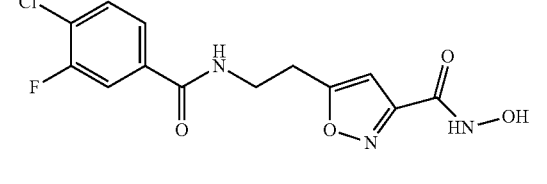 | 5-(2-(4-chloro-3-fluorobenzamido)ethyl)-N-hydroxyisoxazole-3-carboxamide |
| 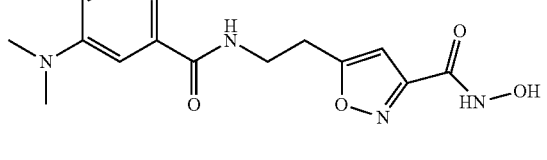 | 5-(2-(3-(dimethylamino)benzamido)ethyl)-N-hydroxyisoxazole-3-carboxamide |
| 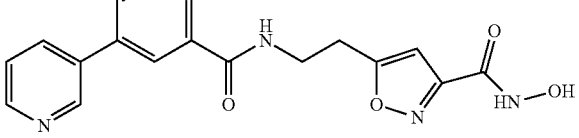 | N-hydroxy-5-(2-(3-(pyridin-3-yl)benzamido)ethyl)isoxazole-3-carboxamide |
| 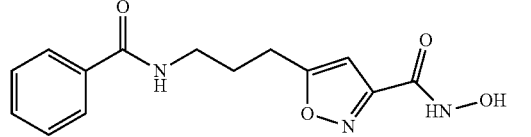 [SMILES: O=C(NCCCc1cc(C(=O)NO)no1)c1ccccc1] | 5-(3-benzamidopropyl)-N-hydroxyisoxazole-3-carboxamide |

TABLE 1-continued

| | |
|---|---|
| 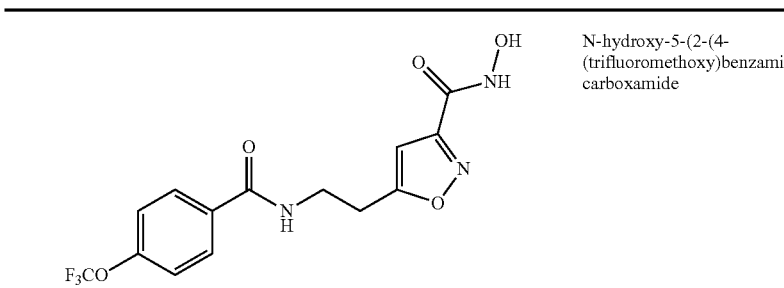 | N-hydroxy-5-(2-(4-(trifluoromethoxy)benzamido)ethyl)isoxazole-3-carboxamide |
| 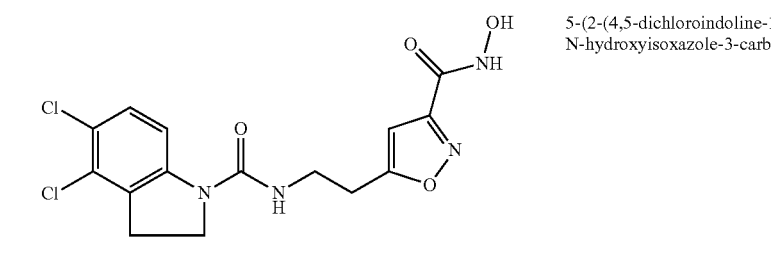 | 5-(2-(4,5-dichloroindoline-1-carboxamido)ethyl)-N-hydroxyisoxazole-3-carboxamide |
| 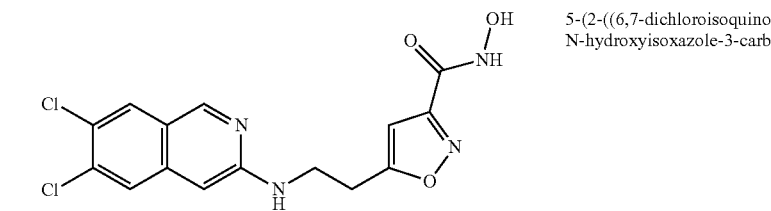 | 5-(2-((6,7-dichloroisoquinolin-3-yl)amino)ethyl)-N-hydroxyisoxazole-3-carboxamide |
| 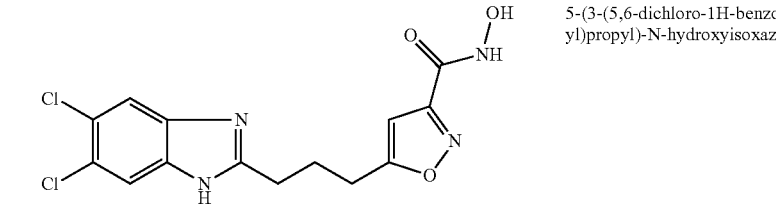 | 5-(3-(5,6-dichloro-1H-benzo[d]imidazol-2-yl)propyl)-N-hydroxyisoxazole-3-carboxamide |
| 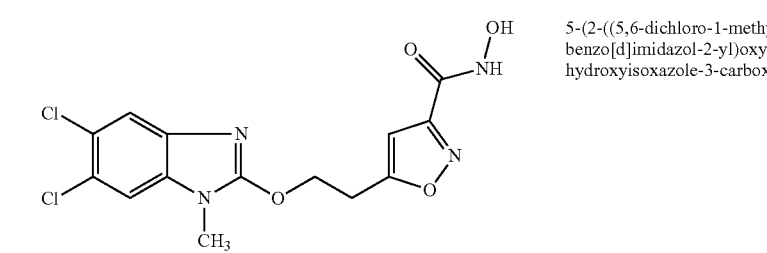 | 5-(2-((5,6-dichloro-1-methyl-1H-benzo[d]imidazol-2-yl)oxy)ethyl)-N-hydroxyisoxazole-3-carboxamide |
| 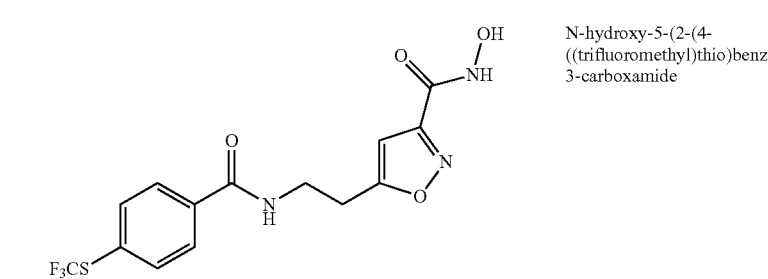 | N-hydroxy-5-(2-(4-((trifluoromethyl)thio)benzamido)ethyl)isoxazole-3-carboxamide |

TABLE 1-continued

| Structure | Name |
|---|---|
| (structure) | 5-(4-(4,5-dichloroindolin-1-yl)-4-oxobutyl)-N-hydroxyisoxazole-3-carboxamide |
| (structure) | 5-(2-((6,7-dichloroquinolin-2-yl)amino)ethyl)-N-hydroxyisoxazole-3-carboxamide |
| (structure) | 5-(3-(5,6-dichlorobenzo[d]thiazol-2-yl)propyl)-N-hydroxyisoxazole-3-carboxamide |
| (structure) | 5-(3-(5,6-dichlorobenzo[d]oxazol-2-yl)propyl)-N-hydroxyisoxazole-3-carboxamide |
| (structure) | N-hydroxy-5-(2-(4-(trifluoromethyl)benzamido)ethyl)isoxazole-3-carboxamide |
| (structure) | 2-(3-(hydroxycarbamoyl)isoxazol-5-yl)ethyl 4,5-dichloroindoline-1-carboxylate |
| (structure) | 5-(2-((6,7-dichloronaphthalen-2-yl)amino)ethyl)-N-hydroxyisoxazole-3-carboxamide |

TABLE 1-continued

| | |
|---|---|
| 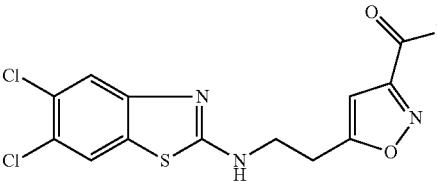 | 5-(2-((5,6-dichlorobenzo[d]thiazol-2-yl)amino)ethyl)-N-hydroxyisoxazole-3-carboxamide |
| 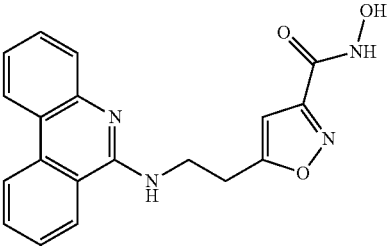 [SMILES: O=C(NO)c1cc(CCNc2nc3ccccc3c3ccccc23)on1] | N-hydroxy-5-(2-(phenanthridin-6-ylamino)ethyl)isoxazole-3-carboxamide |
| 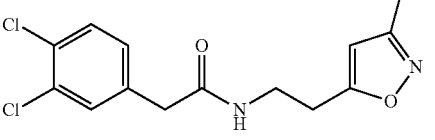 | 5-(2-(2-(3,4-dichlorophenyl)acetamido)ethyl)-N-hydroxyisoxazole-3-carboxamide |
| 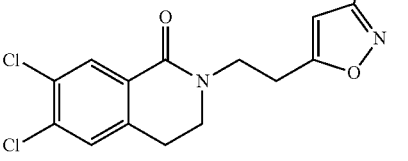 | 5-(2-(6,7-dichloro-1-oxo-3,4-dihydroisoquinolin-2(1H)-yl)ethyl)-N-hydroxyisoxazole-3-carboxamide |
| 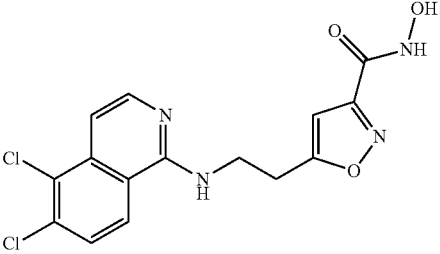 [SMILES: O=C(NO)c1cc(CCNc2nccc3c(Cl)c(Cl)ccc23)on1] | 5-(2-((5,6-dichloroisoquinolin-1-yl)amino)ethyl)-N-hydroxyisoxazole-3-carboxamide |
| 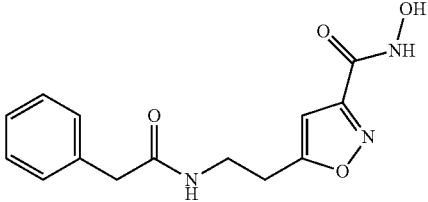 [SMILES: O=C(Cc1ccccc1)NCCc1cc(C(=O)NO)no1] | N-hydroxy-5-(2-(2-phenylacetamido)ethyl)isoxazole-3-carboxamide |

TABLE 1-continued

| | |
|---|---|
| 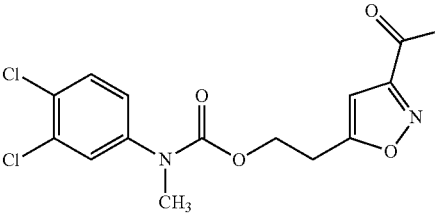 | 2-(3-(hydroxycarbamoyl)isoxazol-5-yl)ethyl (3,4-dichlorophenyl)(methyl)carbamate |
| 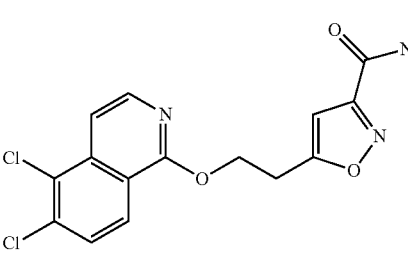 | 5-(2-((5,6-dichloroisoquinolin-1-yl)oxy)ethyl)-N-hydroxyisoxazole-3-carboxamide |
| 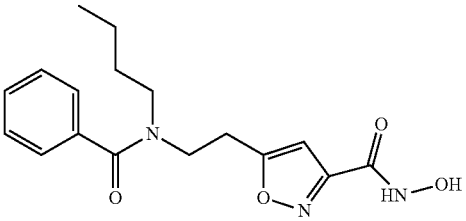 [SMILES: CCCCN(CCc1cc(C(=O)NO)no1)C(=O)c1ccccc1] | 5-(2-(N-butylbenzamido)ethyl)-N-hydroxyisoxazole-3-carboxamide |
| 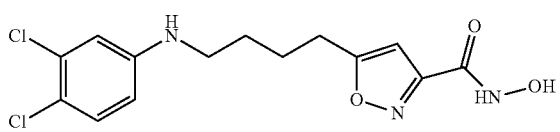 [SMILES: O=C(NO)c1cc(CCCCNc2ccc(Cl)c(Cl)c2)on1] | 5-(4-((3,4-dichlorophenyl)amino)butyl)-N-hydroxyisoxazole-3-carboxamide |
| 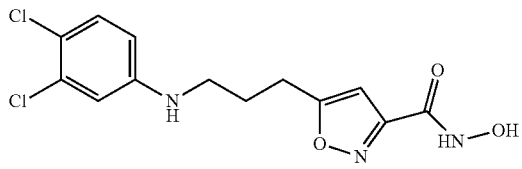 [SMILES: O=C(NO)c1cc(CCCNc2ccc(Cl)c(Cl)c2)on1] | 5-(3-((3,4-dichlorophenyl)amino)propyl)-N-hydroxyisoxazole-3-carboxamide |
| 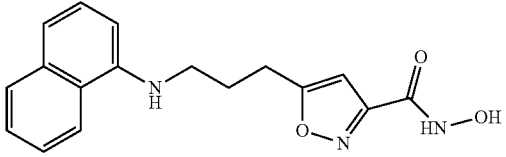 [SMILES: O=C(NO)c1cc(CCCNc2cccc3ccccc23)on1] | N-hydroxy-5-(3-(naphthalen-1-ylamino)propyl)isoxazole-3-carboxamide |
| 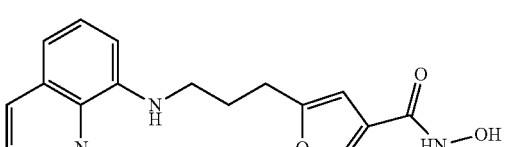 | N-hydroxy-5-(3-(quinolin-8-ylamino)propyl)isoxazole-3-carboxamide |

TABLE 1-continued

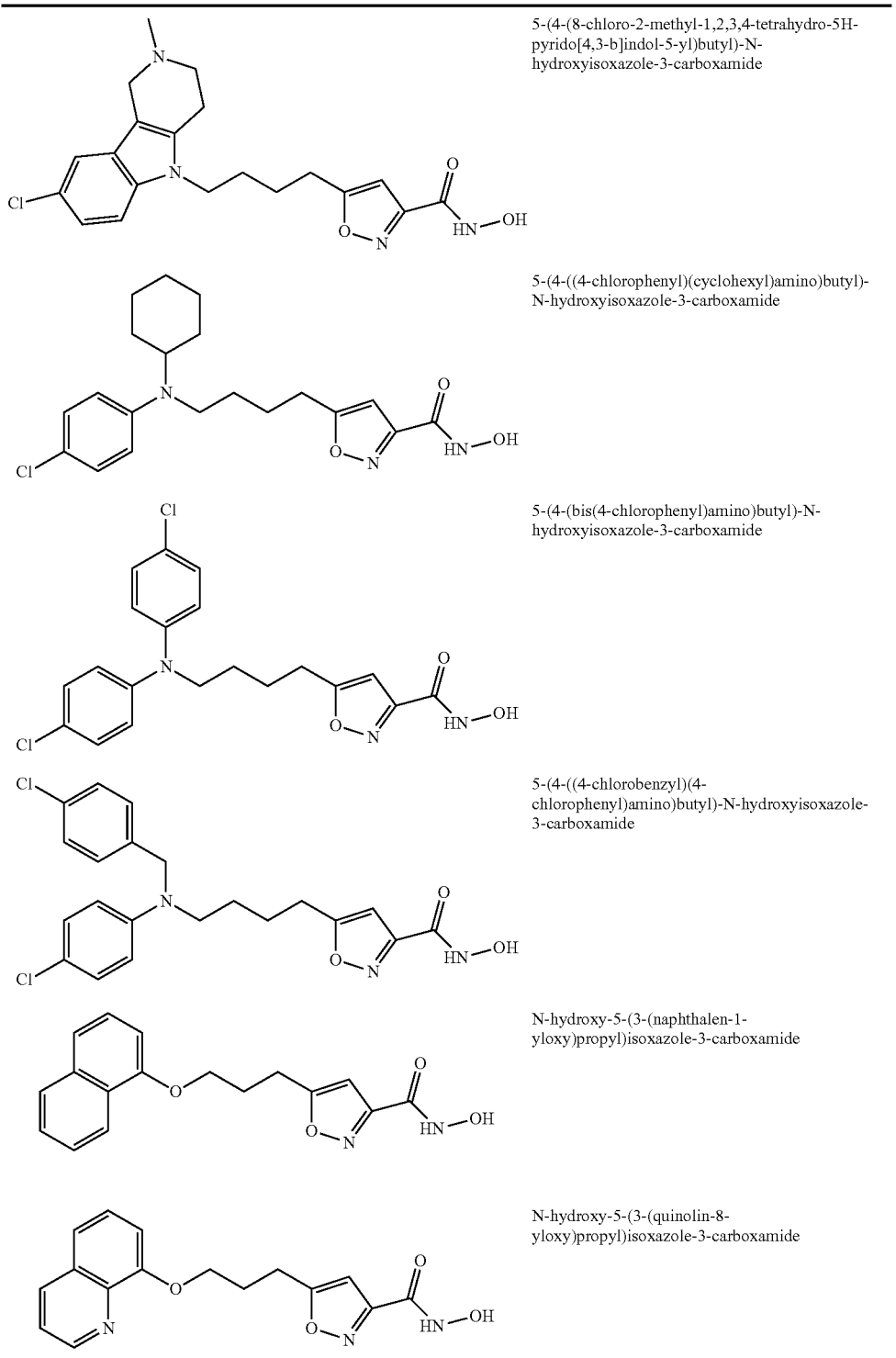

| | |
|---|---|
| | 5-(4-(8-chloro-2-methyl-1,2,3,4-tetrahydro-5H-pyrido[4,3-b]indol-5-yl)butyl)-N-hydroxyisoxazole-3-carboxamide |
| | 5-(4-((4-chlorophenyl)(cyclohexyl)amino)butyl)-N-hydroxyisoxazole-3-carboxamide |
| | 5-(4-(bis(4-chlorophenyl)amino)butyl)-N-hydroxyisoxazole-3-carboxamide |
| | 5-(4-((4-chlorobenzyl)(4-chlorophenyl)amino)butyl)-N-hydroxyisoxazole-3-carboxamide |
| | N-hydroxy-5-(3-(naphthalen-1-yloxy)propyl)isoxazole-3-carboxamide |
| | N-hydroxy-5-(3-(quinolin-8-yloxy)propyl)isoxazole-3-carboxamide |

In another embodiment, the present disclosure provides pharmaceutical compositions comprising a Compound of the Disclosure and a pharmaceutically acceptable carrier.

In another embodiment, the present disclosure provides a Compound of the Disclosure for use in therapeutic treatments of, for example, cancers, inflammations, traumatic brain injuries, neurodegenerative disorders, neurological diseases, peripheral neuropathies, strokes, hypertension, autoimmune diseases, inflammatory diseases, and malaria.

In another embodiment, the present disclosure provides a Compound of the Disclosure for use in therapeutic treatments of cancers.

In another embodiment, the present disclosure provides a Compound of the Disclosure that increases the sensitivity of a cancer cell to the cytotoxic effects of radiotherapy and/or chemotherapy.

In another embodiment, the present disclosure provides a Compound of the Disclosure that selectively inhibits HDAC6 over other HDAC isozymes.

In another embodiment, the present disclosure provides a use of a Compound of the Disclosure for the manufacture of a medicament for treating a disease or condition of interest, e.g., a cancer, a neurological disease, a psychiatric illness, a neurodegenerative disorder, a peripheral neuropathy, stroke, hypertension, an inflammation, traumatic brain injury, rheumatoid arthritis, allograft rejection, and autoimmune diseases.

In another embodiment, the present disclosure provides a kit comprising a Compound of the Disclosure and, optionally, a packaged composition comprising a second therapeutic agent useful in the treatment of a disease or condition of interest, and a package insert containing directions for use in the treatment of a disease or condition, e.g., a cancer, a neurological disease, a psychiatric illness, a neurodegenerative disorder, a peripheral neuropathy, stroke, hypertension, an inflammation, traumatic brain injury, rheumatoid arthritis, allograft rejection, and autoimmune diseases.

In another embodiment, the present disclosure provides synthetic intermediates that can be used to prepare histone deacetylase inhibitors having Formulae I-V.

In another embodiment, the present disclosure provides a compound having Formula VI:

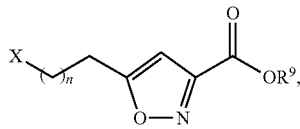

VI wherein:

X is selected from the group consisting of X-1, X-2, X-3, X-4, and X-5 (as defined in connection with Formula I);

$R^1$ is selected from the group consisting of hydrogen and $C_{1-4}$ alkyl;

$R^2$ is selected from the group consisting of optionally substituted $C_6$-$C_{14}$ aryl and aralkyl;

$R^3$ is selected from the group consisting of optionally substituted $C_6$-$C_{14}$ aryl, optionally substituted 5- to 14-membered heteroaryl, and —C(=O)$NR^dR^e$;

$R^{4a}$, $R^{4b}$, $R^{4e}$, and $R^{4f}$ are independently selected from the group consisting of hydrogen, halogen, hydroxy, nitro, cyano, —$NR^aR^b$, —C(=O)$NR^aR^b$, —C(=O)$R^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

$R^{4c}$ and $R^{4d}$ are independently selected from the group consisting of hydrogen and $C_{1-4}$ alkyl; or $R^{4c}$ and $R^{4d}$ taken together form a —C(=O)— with the carbon atom to which they are attached;

$R^{5a}$, $R^{5b}$, $R^{5c}$, and $R^{5d}$ are independently selected from the group consisting of hydrogen, halogen, hydroxy, nitro, cyano, —$NR^aR^b$, —C(=O)$NR^aR^b$, —C(=O)$R^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

Z is selected from the group consisting of —O—, —N($R^8$)—, and —C(=O)—; or

Z is absent;

$R^8$ is selected from the group consisting of hydrogen, $C_{1-4}$ alkyl, optionally substituted $C_{3-6}$ cycloalkyl, optionally substituted $C_6$-$C_{14}$ aryl, aralkyl, optionally substituted 5- to 14-membered heteroaryl, and heteroaralkyl;

$R^9$ is $C_{1-4}$ alkyl;

m is 0, 1, or 2;

n is 1, 2, 3, 4, 5, or 6;

==== represents a single or double bond;

$R^a$, $R^b$, $R^d$, and $R^e$ are independently selected from the group consisting of hydrogen, $C_{1-6}$ alkyl, optionally substituted $C_{3-6}$ cycloalkyl, optionally substituted $C_6$-$C_{14}$ aryl, optionally substituted 5- to 14-membered heteroaryl; or $R^a$ and $R^b$ taken together with the nitrogen atom to which they are attached form an optionally substituted 3- to 12-membered heterocyclo; or $R^d$ and $R^e$ taken together with the nitrogen atom to which they are attached form an optionally substituted 3- to 12-membered heterocyclo; and $R^c$ is $C_{1-4}$ alkyl.

In another embodiment, the present disclosure provides a compound having Formula VI with the proviso that when Z is absent, $R^3$ is a bicyclic or tricyclic $C_{10-14}$ aryl, a bicyclic or tricyclic 9- to 14-membered heteroaryl, or —C(=O)$NR^dR^e$.

In one embodiment, the present disclosure provides a compound having Formula VI, and the pharmaceutically acceptable salts, solvates, and prodrugs thereof, wherein X is X-1, X-2, X-3, or X-4;

Z is —O—;

$R^1$ is selected from the group consisting of hydrogen and $C_{1-4}$ alkyl;

$R^2$ is optionally substituted $C_6$-$C_{14}$ aryl;

$R^3$ is selected from the group consisting of optionally substituted $C_6$-$C_{14}$ aryl and optionally substituted 5- to 14-membered heteroaryl;

$R^{4a}$ and $R^{4b}$ are independently selected from the group consisting of hydrogen, halogen, hydroxy, nitro, cyano, —$NR^aR^b$, —C(=O)$NR^aR^b$, —C(=O)$R^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

$R^{4c}$ and $R^{4d}$ are independently selected from the group consisting of hydrogen and $C_{1-4}$ alkyl;

$R^{5a}$, $R^{5b}$, $R^{5c}$, and $R^{5d}$ are independently selected from the group consisting of hydrogen, halogen, hydroxy, nitro, cyano, —$NR^aR^b$, —C(=O)$NR^aR^b$, —C(=O)$R^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

$R^a$ and $R^b$ are independently selected from the group consisting of hydrogen and $C_{1-6}$ alkyl; or $R^a$ and $R^b$ taken together with the nitrogen atom to which they are attached form a 3- to 7-membered heterocyclo; and $R^c$ is $C_{1-4}$ alkyl.

In another embodiment, the present disclosure provides a compound having Formula VI, wherein X is X-1. In another embodiment, le is hydrogen. In another embodiment, $R^2$ is optionally substituted phenyl. In another embodiment, $R^2$ is optionally substituted 1-naphthyl. In another embodiment, $R^2$ is optionally substituted 2-naphthyl. In another embodiment, $R^2$ is aralkyl.

In another embodiment, the present disclosure provides a compound having Formula VI, wherein X is X-2. In another embodiment, Z is —O—. In another embodiment, Z is —N($R^8$)— In another embodiment, Z is —C(=O)—. In another embodiment, $R^3$ is optionally substituted $C_6$-$C_{14}$ aryl. In another embodiment, $R^3$ is optionally substituted 5- to 14-membered heteroaryl. In another embodiment, $R^3$ is —C(=O)$NR^dR^e$. In another embodiment, Z is absent and $R^3$ is a bicyclic or tricyclic $C_{10-14}$ aryl, a bicyclic or tricyclic 9- to 14-membered heteroaryl, or —C(=O)$NR^dR^e$.

In another embodiment, the present disclosure provides a compound having Formula VI, wherein X is X-3.

In another embodiment, the present disclosure provides a compound having Formula VI, wherein X is X-4.

In another embodiment, the present disclosure provides a compound having Formula VI, wherein X is X-5.

In another embodiment, the present disclosure provides a compound having Formula VII:

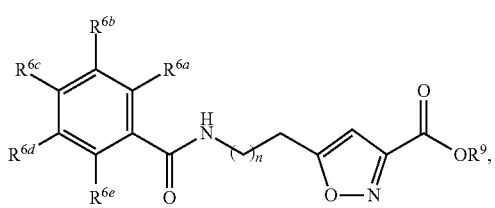

wherein:

$R^{6a}$, $R^{6b}$, $R^{6c}$, $R^{6d}$, an $R^{6e}$ are each independently selected from the group consisting of hydrogen, halogen, hydroxy, nitro, cyano, —$NR^a R^b$, —$C(=O)NR^a R^b$, —$C(=O)R^c$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-6}$ cycloalkyl, optionally substituted phenyl, optionally substituted 5- or 6-membered heteroaryl, and optionally substituted 5- or 6-membered heterocyclo;

$R^a$ and $R^b$ are independently selected from the group consisting of hydrogen and $C_{1-4}$ alkyl; or $R^a$ and $R^b$ taken together with the nitrogen atom to which they are attached form a 3- to 7-membered heterocyclo;

$R^c$ is $C_{1-4}$ alkyl;

n is 1, 2, or 3; and $R^9$ is $C_{1-4}$ alkyl.

In another embodiment, the present disclosure provides a compound having Formula VII, wherein $R^{6a}$, $R^{6b}$, $R^{6c}$, $R^{6d}$, an $R^{6e}$ are each independently selected from the group consisting of hydrogen, halogen, hydroxy, nitro, cyano, —$NR^a R^b$, —$C(=O)NR^a R^b$, —$C(=O)R^c$, $C_{1-4}$ alkyl, $C_{1-4}$ alkoxy, and $C_{1-4}$ haloalkyl. In another embodiment, $R^{6a}$, $R^{6b}$, $R^{6c}$, $R^{6d}$, and $R^{6e}$ are each independently selected from the group consisting of hydrogen, halogen, cyano, $C_{1-4}$ alkyl, and $C_{1-4}$ alkoxy.

In another embodiment, the present disclosure provides a compound having Formula VII, wherein n is 1. In another embodiment, n is 2. In another embodiment, n is 3.

In another embodiment, the present disclosure provides a compound having Formula VIII:

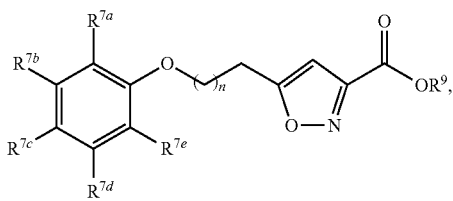

wherein:

$R^{7a}$, $R^{7b}$, $R^{7c}$, $R^{7d}$, and $R^{7e}$ are each independently selected from the group consisting of hydrogen, halogen, hydroxy, nitro, cyano, —$NR^a R^b$, —$C(=O)NR^a R^b$, —$C(=O)R^c$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-6}$ cycloalkyl, optionally substituted phenyl, optionally substituted 5- or 6-membered heteroaryl, and optionally substituted 5- or 6-membered heterocyclo;

$R^a$ and $R^b$ are independently selected from the group consisting of hydrogen and $C_{1-4}$ alkyl; or $R^a$ and $R^b$ taken together with the nitrogen atom to which they are attached form a 3- to 7-membered heterocyclo;

$R^c$ is $C_{1-4}$ alkyl;

n is 1, 2, or 3; and $R^9$ is $C_{1-4}$ alkyl.

In another embodiment, the present disclosure provides a compound having Formula VIII, wherein $R^{7a}$, $R^{7b}$, $R^{7c}$, $R^{7d}$, and $R^{7e}$ are each independently selected from the group consisting of hydrogen, halogen, hydroxy, nitro, cyano, —$NR^a R^b$, —$C(=O)NR^a R^b$, —$C(=O)R^c$, $C_{1-4}$ alkyl, $C_{1-4}$ alkoxy, and $C_{1-4}$ haloalkyl. In another embodiment, $R^{7a}$, $R^{7b}$, $R^{7c}$, $R^{7d}$, and $R^{7e}$ are each independently selected from the group consisting of hydrogen, halogen, cyano, $C_{1-4}$ alkyl, and $C_{1-4}$ alkoxy.

In another embodiment, the present disclosure provides a compound having Formula VIII, wherein n is 1. In another embodiment, n is 2. In another embodiment, n is 3.

In another embodiment, the present disclosure provides a compound having Formula IX:

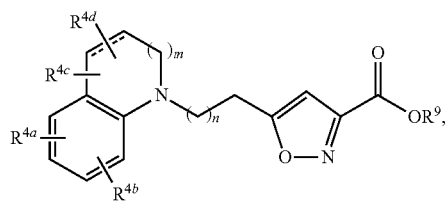

wherein:

$R^{4a}$ and $R^{4b}$ are independently selected from the group consisting of hydrogen, halogen, cyano, $C_{1-4}$ alkyl, and $C_{1-4}$ alkoxy;

$R^{7c}$ and $R^{4d}$ are independently selected from the group consisting of hydrogen and methyl;

m is 0 or 1;

n is 1, 2, or 3;

==== represents a single or double bond; and $R^9$ is $C_{1-4}$ alkyl.

In another embodiment, the present disclosure provides a compound having Formula IX, wherein m is 0 and ==== represents a double bond.

In another embodiment, the present disclosure provides a compound having Formula IX, wherein m is 1 and ==== represents a single bond.

In another embodiment, the present disclosure a compound having Formula IX, wherein n is 1. In another embodiment, n is 2. In another embodiment, n is 3.

In another embodiment, the present disclosure provides a compound having Formula X:

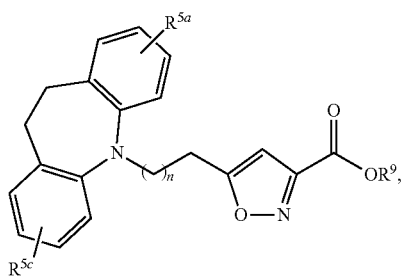

wherein:

R[5a] and R[5c] are independently selected from the group consisting of hydrogen, halogen, cyano, $C_{1-4}$ alkyl, and $C_{1-4}$ alkoxy;

n is 1, 2, or 3; and

R[9] is $C_{1-4}$ alkyl.

In another embodiment, the present disclosure provides a compound having Formula X, wherein n is 1. In another embodiment, n is 2. In another embodiment, n is 3.

In another embodiment, the present disclosure provides a compound having any one of Formula VI-X, wherein R[9] is —CH$_2$CH$_3$.

In another embodiment, Intermediates of the Disclosure are any one or more of the compounds having Formula VI of Table 1A.

TABLE 1A

| Structure | Name |
|---|---|
| 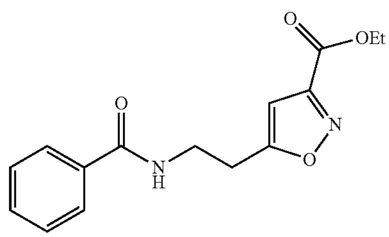 [SMILES: CCOC(=O)c1cc(CCNC(=O)c2ccccc2)on1] | ethyl 5-(2-benzamidoethyl)isoxazole-3-carboxylate |
| 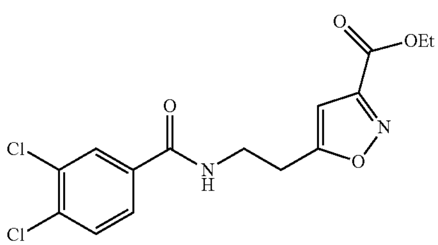 [SMILES: CCOC(=O)c1cc(CCNC(=O)c2ccc(Cl)c(Cl)c2)on1] | ethyl 5-(2-(3,4-dichlorobenzamido)ethyl)isoxazole-3-carboxylate |
| 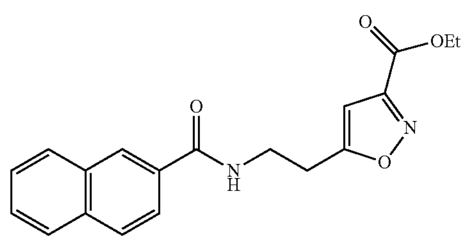 [SMILES: CCOC(=O)c1cc(CCNC(=O)c2ccc3ccccc3c2)on1] | ethyl 5-(2-(2-naphthamido)ethyl)isoxazole-3-carboxylate |
| 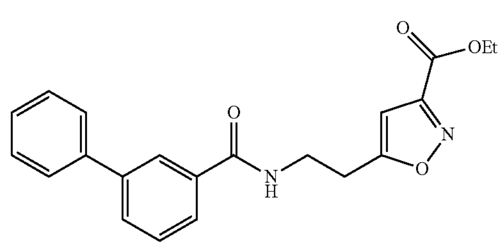 [SMILES: CCOC(=O)c1cc(CCNC(=O)c2cccc(-c3ccccc3)c2)on1] | ethyl 5-(2-([1,1'-biphenyl]-3-carboxamido)ethyl)isoxazole-3-carboxylate |
| 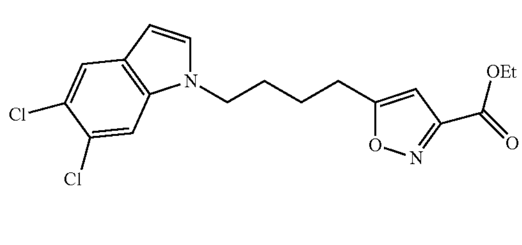 [SMILES: CCOC(=O)c1cc(CCCCn2ccc3cc(Cl)c(Cl)cc32)on1] | ethyl 5-(4-(5,6-dichloro-1H-indol-1-yl)butyl)isoxazole-3-carboxylate |

TABLE 1A-continued

| | |
|---|---|
| 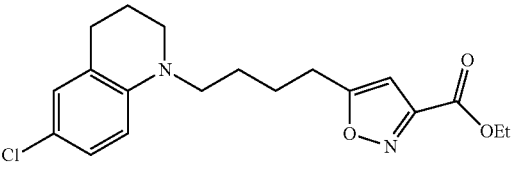 [SMILES: CCOC(=O)c1cc(CCCCN2CCCc3cc(Cl)ccc32)on1] | ethyl 5-(4-(6-chloro-3,4-dihydroquinolin-1(2H)-yl)butyl)isoxazole-3-carboxylate |
| 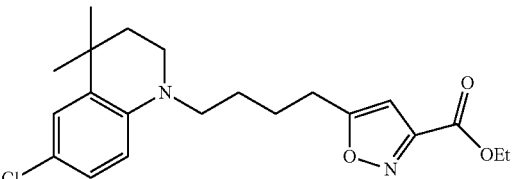 | ethyl 5-(4-(6-chloro-4,4-dimethyl-3,4-dihydroquinolin-1(2H)-yl)butyl)isoxazole-3-carboxylate |
| 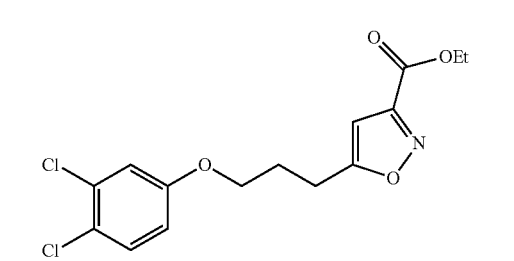 [SMILES: CCOC(=O)c1cc(CCCOc2ccc(Cl)c(Cl)c2)on1] | ethyl 5-(3-(3,4-dichlorophenoxy)propyl)isoxazole-3-carboxylate |
| 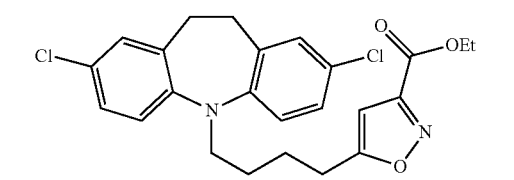 [SMILES: CCOC(=O)c1cc(CCCCN2c3ccc(Cl)cc3CCc3cc(Cl)ccc32)on1] | ethyl 5-(4-(2,8-dichloro-10,11-dihydro-5H-dibenzo[b,f]azepin-5-yl)butyl)isoxazole-3-carboxylate |
| 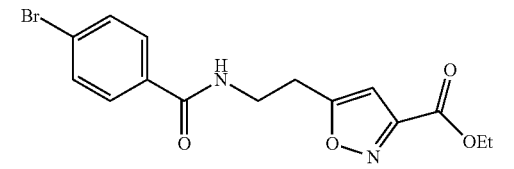 | ethyl 5-(2-(4-bromobenzamido)ethyl)isoxazole-3-carboxylate |
| 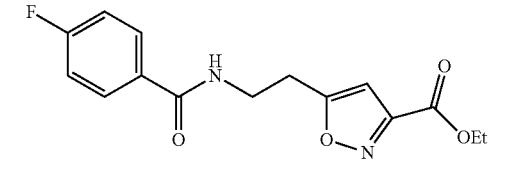 [SMILES: CCOC(=O)c1cc(CCNC(=O)c2ccc(F)cc2)on1] | ethyl 5-(2-(4-fluorobenzamido)ethyl)isoxazole-3-carboxylate |
| 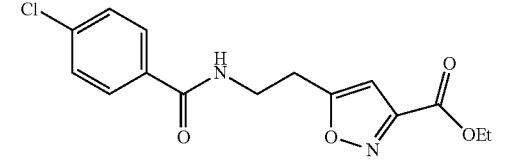 [SMILES: CCOC(=O)c1cc(CCNC(=O)c2ccc(Cl)cc2)on1] | ethyl 5-(2-(4-chlorobenzamido)ethyl)isoxazole-3-carboxylate |
| 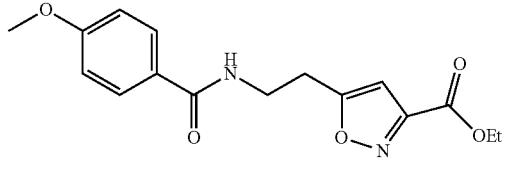 [SMILES: CCOC(=O)c1cc(CCNC(=O)c2ccc(OC)cc2)on1] | ethyl 5-(2-(4-methoxybenzamido)ethyl)isoxazole-3-carboxylate |

TABLE 1A-continued

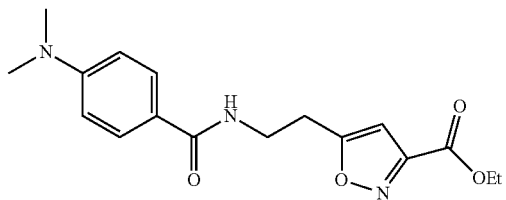 [SMILES: CCOC(=O)c1cc(CCNC(=O)c2ccc(N(C)C)cc2)on1]
ethyl 5-(2-(4-(dimethylamino)benzamido)ethyl)isoxazole-3-carboxylate

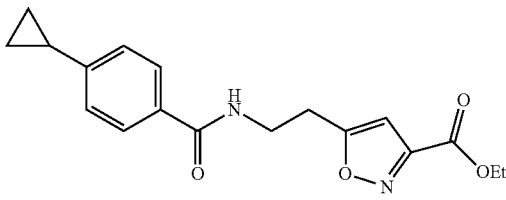 [SMILES: CCOC(=O)c1cc(CCNC(=O)c2ccc(C3CC3)cc2)on1]
ethyl 5-(2-(4-cyclopropylbenzamido)ethyl)isoxazole-3-carboxylate

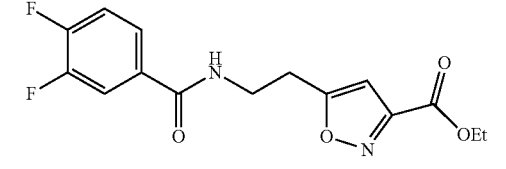 [SMILES: CCOC(=O)c1cc(CCNC(=O)c2ccc(F)c(F)c2)on1]
ethyl 5-(2-(3,4-difluorobenzamido)ethyl)isoxazole-3-carboxylate

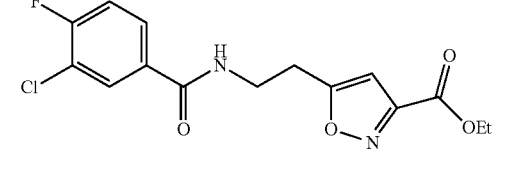
ethyl 5-(2-(3-chloro-4-fluorobenzamido)ethyl)isoxazole-3-carboxylate

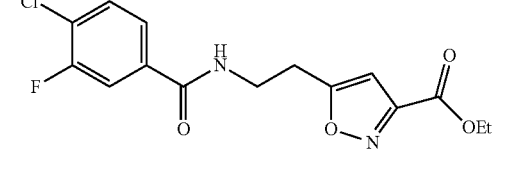
ethyl 5-(2-(4-chloro-3-fluorobenzamido)ethyl)isoxazole-3-carboxylate

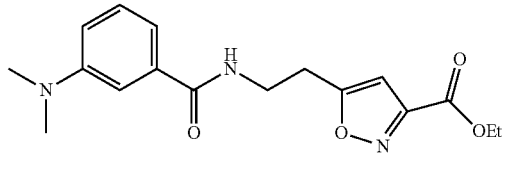 [SMILES: CCOC(=O)c1cc(CCNC(=O)c2cccc(N(C)C)c2)on1]
ethyl 5-(2-(3-(dimethylamino)benzamido)ethyl)isoxazole-3-carboxylate

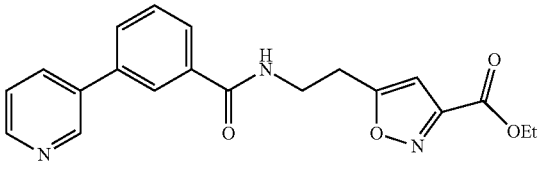 [SMILES: CCOC(=O)c1cc(CCNC(=O)c2cccc(-c3cccnc3)c2)on1]
ethyl 5-(2-(3-(pyridin-3-yl)benzamido)ethyl)isoxazole-3-carboxylate

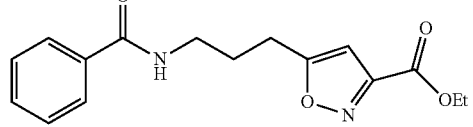
ethyl 5-(3-benzamidopropyl)isoxazole-3-carboxylate

TABLE 1A-continued

| Structure | Name |
|---|---|
| 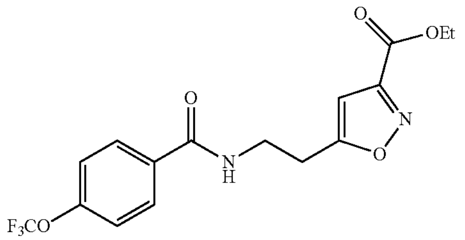 | ethyl 5-(2-(4-(trifluoromethxoy)benzamido)ethyl)isoxazole-3-carboxylate |
| 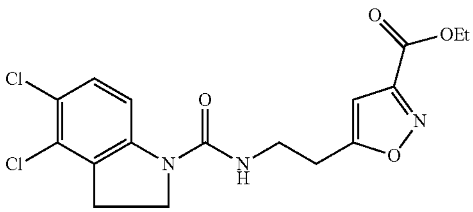 [SMILES: CCOC(=O)c1cc(CCNC(=O)N2CCc3c2ccc(Cl)c3Cl)on1] | ethyl 5-(2-(4,5-dichloroindoline-1-carboxamido)ethyl)isoxazole-3-carboxylate |
| 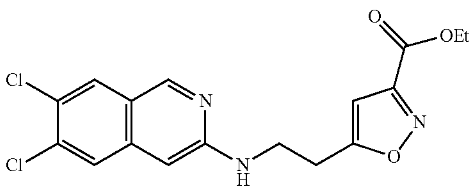 [SMILES: CCOC(=O)c1cc(CCNc2cc3cc(Cl)c(Cl)cc3cn2)on1] | ethyl 5-(2-((6,7-dichloroisoquinolin-3-yl)amino)ethyl)isoxazole-3-carboxylate |
| 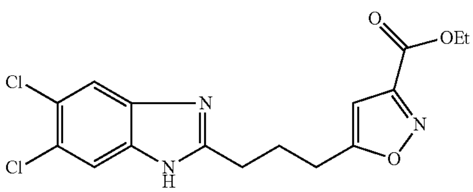 [SMILES: CCOC(=O)c1cc(CCCc2nc3cc(Cl)c(Cl)cc3[nH]2)on1] | ethyl 5-(3-(5,6-dichloro-1H-benzo[d]imidazol-2-yl)propyl)isoxazole-3-carboxylate |
| 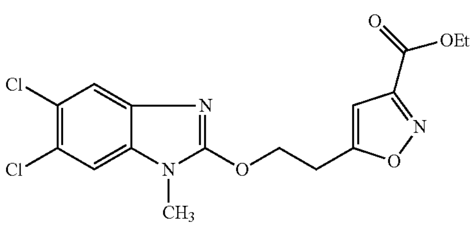 [SMILES: CCOC(=O)c1cc(CCOc2nc3cc(Cl)c(Cl)cc3n2C)on1] | ethyl 5-(2-((5,6-dichloro-1-methyl-1H-benzo[d]imidazol-2-yl)oxy)ethyl)isoxazole-3-carboxylate |
| 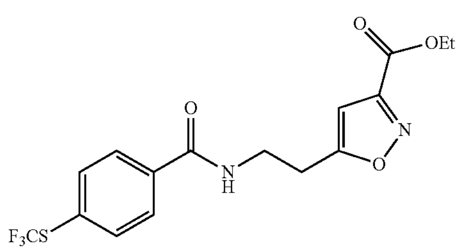 | ethyl 5-(2-(4-((trifluoromethyl)thio)benzamido)ethyl)isoxazole-3-carboxylate |
| 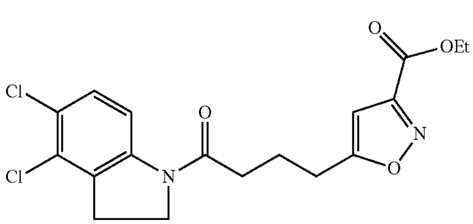 [SMILES: CCOC(=O)c1cc(CCCC(=O)N2CCc3c2ccc(Cl)c3Cl)on1] | ethyl 5-(4-(4,5-dichloroindolin-1-yl)-4-oxobutyl)isoxazole-3-carboxylate |

TABLE 1A-continued

| Structure | Name |
|---|---|
| (structure) | ethyl 5-(2-((6,7-dichloroquinolin-2-yl)amino)ethyl)isoxazole-3-carboxylate |
| (structure) | ethyl 5-(3-(5,6-dichlorobenzo[d]thiazol-2-yl)propyl)isoxazole-3-carboxylate |
| (structure) | ethyl 5-(3-(5,6-dichlorobenzo[d]oxazol-2-yl)propyl)isoxazole-3-carboxylate |
| (structure) | ethyl 5-(2-(4-(trifluoromethyl)benzamido)ethyl)isoxazole-3-carboxylate |
| (structure) | ethyl 5-(2-((4,5-dichloroindolin-1-carbonyl)oxy)ethyl)isoxazole-3-carboxylate |
| (structure) | ethyl 5-(2-((6,7-dichloronaphthalen-2-yl)amino)ethyl)isoxazole-3-carboxylate |
| (structure) | ethyl 5-(2-((5,6-dichlorobenzo[d]thiazol-2-yl)amino)ethyl)isoxazole-3-carboxylate |
| (structure) | ethyl 5-(2-(phenanthridin-6-ylamino)ethyl)isoxazole-3-carboxylate |

TABLE 1A-continued

| Structure | Name |
|---|---|
| | ethyl 5-(2-(2-(3,4-dichlorophenyl)acetamido)ethyl)isoxazole-3-carboxylate |
| | ethyl 5-(2-(6,7-dichloro-1-oxo-3,4-dihydroisoquinolin-2(1H)-yl)ethyl)isoxazole-3-carboxylate |
| | ethyl 5-(2-((5,6-dichloroisoquinolin-1-yl)amino)ethyl)isoxazole-3-carboxylate |
| | ethyl 5-(2-(2-phenylacetamido)ethyl)isoxazole-3-carboxylate |
| | ethyl 5-(2-(((3,4-dichlorophenyl)(methyl)carbamoyl)oxy)ethyl)isoxazole-3-carboxylate |
| | ethyl 5-(2-((5,6-dichloroisoquinolin-1-yl)oxy)ethyl)isoxazole-3-carboxylate |
| | ethyl 5-(2-(N-butylbenzamido)ethyl)isoxazole-3-carboxylate |

TABLE 1A-continued

| Structure | Name |
|---|---|
| | ethyl 5-(4-((3,4-dichlorophenyl)amino)butyl)isoxazole-3-carboxylate |
| | ethyl 5-(3-((3,4-dichlorophenyl)amino)propyl)isoxazole-3-carboxylate |
| | ethyl 5-(3-(naphthalen-1-ylamino)propyl)isoxazole-3-carboxylate |
| | ethyl 5-(3-(quinolin-8-ylamino)propyl)isoxazole-3-carboxylate |
| | ethyl 5-(4-(8-chloro-2-methyl-1,2,3,4-tetrahydro-5H-pyrido[4,3-b]indol-5-yl)butyl)isoxazole-3-carboxylate |
| | ethyl 5-(4-((4-chlorophenyl)(cyclohexyl)amino)butyl)isoxazole-3-carboxylate |
| | ethyl 5-(4-(bis(4-chlorophenyl)amino)butyl)isoxazole-3-carboxylate |

TABLE 1A-continued

| Structure | Name |
|---|---|
| (structure) | ethyl 5-(4-((4-chlorobenzyl)(4-chlorophenyl)amino)butyl)isoxazole-3-carboxylate |
| (structure) | ethyl 5-(3-(naphthalen-1-yloxy)propyl)isoxazole-3-carboxylate |
| (structure) | ethyl 5-(3-(quinolin-8-yloxy)propyl)isoxazole-3-carboxylate |

In another embodiment, the present disclosure provides methods of preparing the Compounds of the Disclosure.

In another embodiment, the present disclosure provides a method of making a compound having Formula I, the method comprising (1) contacting a compound having Formula VI with NH$_2$OH in the presence of a solvent; and, optionally, (2) isolating the compound having Formula I.

In another embodiment, the present disclosure provides a method of making a compound having Formula II, the method comprising (1) contacting a compound having Formula VII with NH$_2$OH in the presence of a solvent; and, optionally, (2) isolating the compound having Formula II.

In another embodiment, the present disclosure provides a method of making a compound having Formula III, the method comprising (1) contacting a compound having Formula VIII with NH$_2$OH in the presence of a solvent; and, optionally, (2) isolating the compound having Formula III.

In another embodiment, the present disclosure provides a method of making a compound having Formula IV, the method comprising (1) contacting a compound having Formula IX with NH$_2$OH in the presence of a solvent; and, optionally, (2) isolating the compound having Formula IV.

In another embodiment, the present disclosure provides a method of making a compound having Formula X, the method comprising (1) contacting a compound having Formula X with NH$_2$OH in the presence of a solvent; and, optionally, (2) isolating the compound having Formula X.

In another embodiment, the present disclosure provides a method of making a compound having any one of Formulae V-X, wherein the contacting of NH$_2$OH is carried out in the presence of a base. In one embodiment, the base is NaOH.

In another embodiment, the present disclosure provides a method of making a compound having any one of Formulae V-X, wherein the contacting of NH$_2$OH is carried out at a temperature of about 20° C. or less. In one embodiment, the temperature is about 0° C.

In another embodiment, the present disclosure provides a method of making a compound having any one of Formulae V-X, wherein the solvent comprises water, methanol, or tetrahydrofuran (THF), or a mixture thereof.

In the present disclosure, the term "halo" or "halogen" as used by itself or as part of another group refers to —Cl, —F, —Br, or —I. In one embodiment, the halo is —Cl or —F. In one embodiment, the halo is —Cl.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., C$_{1-12}$ alkyl, or the number of carbon atoms designated, e.g., a C$_1$ alkyl such as methyl, a C$_2$ alkyl such as ethyl, a C$_3$ alkyl such as propyl or isopropyl, a C$_{1-3}$ alkyl such as methyl, ethyl, propyl, or isopropyl, and so on. In one embodiment, the alkyl is a C$_{1-10}$ alkyl. In another embodiment, the alkyl is a C$_{1-6}$ alkyl. In another embodiment, the alkyl is a C$_{1-4}$ alkyl. In another embodiment, the alkyl is a straight chain C$_{1-10}$ alkyl. In another embodiment, the alkyl is a branched chain C$_{3-10}$ alkyl. In another embodiment, the alkyl is a straight chain C$_{1-6}$ alkyl. In another embodiment, the alkyl is a branched chain C$_{3-6}$ alkyl. In another embodiment, the alkyl is a straight chain C$_{1-4}$ alkyl. In another embodiment, the alkyl is a branched chain C$_{3-4}$ alkyl. In another embodiment, the alkyl is a straight or branched chain C$_{3-4}$ alkyl. Non-limiting exemplary C$_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary C$_{1-4}$ alkyl groups include methyl, ethyl, propyl, isopropyl, butyl, sec-butyl, tert-butyl, and iso-butyl.

In the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms, i.e., C$_{3-12}$ cycloalkyl, or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

In the present disclosure, the term "optionally substituted cycloalkyl" as used by itself or as part of another group means that the cycloalkyl as defined above is either unsubstituted or substituted with one, two, or three substituents independently selected from the group consisting of halogen, hydroxy, nitro, cyano, —$SCH_3$, —$SCF_3$, —$NR^aR^b$, —$C(O)NR^aR^b$, —$C(=O)CH_3$, $C_{1-6}$ alkyl, $C_{2-6}$ alkenyl, $C_{2-6}$ alkynyl, $C_{1-6}$ alkoxy, $C_{1-6}$ haloalkyl, optionally substituted $C_{3-8}$ cycloalkyl, optionally substituted aryl, optionally substituted heteroaryl, and optionally substituted heterocyclo. In one embodiment, the optionally substituted cycloalkyl is substituted with two substituents. In another embodiment, the optionally substituted cycloalkyl is substituted with one substituent.

In the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In another embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-6}$ haloalkyl group In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-6}$ alkoxy group. In another embodiment, the alkoxy group is chosen from a $C_{1-4}$ alkyl attached to a terminal oxygen atom, e.g., methoxy, ethoxy, and tert-butoxy.

In the present disclosure, the term "haloalkoxy" as used by itself or as part of another group refers to a $C_{1-4}$ haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic, bicyclic, or tricyclic aromatic ring system having from six to fourteen carbon atoms, i.e., $C_6$-$C_{14}$ aryl. Non-limiting exemplary aryl groups include phenyl (abbreviated as "Ph"), 1-naphthyl, 1-naphthyl, phenanthryl, anthracyl, indenyl, azulenyl, biphenyl, biphenylenyl, and fluorenyl groups. In one embodiment, the aryl group is chosen from phenyl, 1-naphthyl, or 2-naphthyl. In one embodiment, the aryl is a bicyclic or tricyclic $C_{10}$-$C_{14}$ aromatic ring system.

In the present disclosure, the term "optionally substituted aryl" as used herein by itself or as part of another group means that the aryl as defined above is either unsubstituted or substituted with one to five substituents independently selected from the group consisting of halogen, hydroxy, nitro, cyano, —$SCH_3$, —$SCF_3$, —$NR^aR^b$, —$C(=O)NR^aR^b$, —$C(=O)R^c$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-12}$ cycloalkyl, optionally substituted $C_6$-$C_{14}$ aryl, optionally substituted 5- to 14-membered heteroaryl, and optionally substituted 3- to 14-membered heterocyclo, wherein $R^a$ and $R^b$ are independently selected from the group consisting of hydrogen and $C_{1-6}$ alkyl; or $R^a$ and $R^b$ taken together with the nitrogen atom to which they are attached form a 3- to 12-membered heterocyclo; and $R^c$ is $C_{1-4}$ alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl, 3,4-di-chlorophenyl, 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

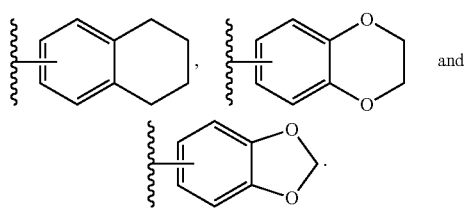

In the present disclosure, the term "heteroaryl" refers to monocyclic, bicyclic, and tricyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In another embodiment, the heteroaryl is a 9- to 14-membered bicyclic aromatic ring system, wherein at least one carbon atom of one of the rings is replaced with a heteroatom independently selected from the group consisting of oxygen, nitrogen and sulfur. Non-limiting exemplary 9- to 14-membered bicyclic aromatic ring systems include:

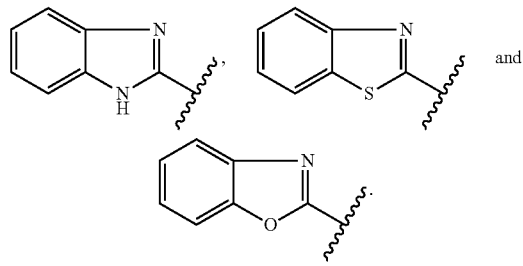

In the present disclosure, the term "optionally substituted heteroaryl" as used by itself or as part of another group means that the heteroaryl as defined above is either unsubstituted or substituted with one to four substituents independently selected from the group consisting of halogen, hydroxy, nitro, cyano, —SCH$_3$, —SCF$_3$, —NR$^a$R$^b$, —C(O)NR$^a$R$^b$, —C(=O)R$^c$, C$_{1-6}$ alkyl, C$_{2-6}$ alkenyl, C$_{2-6}$ alkynyl, C$_{1-6}$ alkoxy, C$_{1-6}$ haloalkyl, haloalkoxy, optionally substituted C$_{3-12}$ cycloalkyl, optionally substituted C$_6$-C$_{14}$ aryl, optionally substituted 5- to 14-membered heteroaryl, and optionally substituted 3- to 14-membered heterocyclo, wherein R$^a$ and R$^b$ are independently selected from the group consisting of hydrogen and C$_{1-6}$ alkyl; or R$^a$ and R$^b$ taken together with the nitrogen atom to which they are attached form a 3- to 12-membered heterocyclo; and R$^c$ is C$_{1-4}$ alkyl. In one embodiment, the optionally substituted heteroaryl has one substituent. Any available carbon or nitrogen atom can be substituted.

In the present disclosure, the term "heterocycle" or "heterocyclo" as used by itself or as part of another group refers to saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring—CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from the group consisting of halogen, hydroxy, nitro, cyano, —SCH$_3$, —SCF$_3$, —NR$^a$R$^b$, —C(O)NR$^a$R$^b$, —C(=O)R$^c$, C$_{1-6}$ alkyl, C$_{2-6}$ alkenyl, C$_{2-6}$ alkynyl, C$_{1-6}$ alkoxy, C$_{1-6}$ haloalkyl, haloalkoxy, optionally substituted C$_{3-12}$ cycloalkyl, optionally substituted C$_6$-C$_{14}$ aryl, optionally substituted 5- to 14-membered heteroaryl, and optionally substituted 3- to 14-membered heterocyclo, wherein R$^a$ and R$^b$ are independently selected from the group consisting of hydrogen and C$_{1-6}$ alkyl; or R$^a$ and R$^b$ taken together with the nitrogen atom to which they are attached form a 3- to 12-membered heterocyclo; and R$^c$ is C$_{1-4}$ alkyl.

In the present disclosure, the term "aralkyl" as used by itself or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the aralkyl group is a C$_1$ or C$_2$ alkyl substituted with one optionally substituted aryl group. In one embodiment, the aralkyl group is a C$_1$ or C$_2$ alkyl substituted with one optionally substituted phenyl group. Non-limiting exemplary aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the term "heteroaralkyl" as used by itself or as part of another group refers to an alkyl group substituted with one, two, or three optionally substituted heteroaryl groups. In one embodiment, the heteroaralkyl group is a C$_{1-4}$ alkyl substituted with one optionally substituted heteroaryl group. In one embodiment, the aralkyl group is a C$_1$ or C$_2$ alkyl substituted with one optionally substituted heteroaryl group. In one embodiment, the heteroaralkyl group is a C$_1$ or C$_2$ alkyl substituted with one optionally substituted heteroaryl group. Non-limiting exemplary heteroaralkyl groups include:

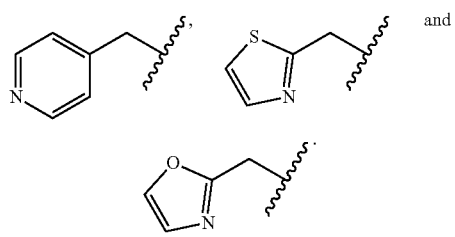

The term "contacting" is used as known in the art and generally refers to the bringing together, e.g., reacting, of reactants, reagents, solvents, catalysts, and reactive groups in such a manner so as to allow their interaction at the molecular level to achieve the desired chemical or physical transformation. In some embodiments, the contacting involves two reactants or reagents, wherein one or more equivalents of one reactant/reagent are used with respect to the other reactant/reagent. The contacting steps of the processes of this disclosure can be conducted for a time and under conditions suitable for preparing the desired product. Unless otherwise specified, reactants, reagents, solvents, catalysts, and reactive groups can be added individually, simultaneously, or separately, and/or can be added in any order. They can be added in the presence or absence of heat, and can optionally be added under an inert atmosphere.

The term "a disease or condition wherein inhibition of HDAC provides a benefit" pertains to a condition in which HDAC and/or the action of HDAC is important or necessary, e.g., for the onset, progress, expression of that disease or condition, or a disease or a condition which is known to be treated by an HDAC inhibitor (such as, e.g., TSA, pivaloyloxymethylbutane (AN-9; Pivanex), FK-228 (Depsipeptide), PXD-101, NVP-LAQ824, SAHA, MS-275, and or MGCD0103). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spino-cerebellar degeneration, Rett syndrome), peripheral neuropathies (Charcot-Marie-Tooth disease, Giant Axonal Neuropathy (GAN)), inflammatory diseases (e.g., osteoarthritis, rheumatoid arthritis, colitis), diseases involving angiogenesis (e.g., cancer, rheumatoid arthritis, psoriasis, diabetic retinopathy), hematopoietic disorders (e.g., anemia, sickle cell anemia, thalassemia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants). One of ordinary skill in the art is readily able to determine whether a compound treats a disease or condition mediated by HDAC for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example, when a cancer is the disease or condition of interest, the second therapeutic agent can be a known chemotherapeutic drug, like taxol, or radiation, for example.

The term "HDAC" refers to a family of enzymes that remove acetyl groups from a protein, for example, the ε-amino groups of lysine residues at the N-terminus of a histone. The HDAC can be a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

The terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the disclosure to an individual, e.g., a mammalian patient including, but not limited to, humans and veterinary animals, in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual, e.g., human patient, in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce HDAC signaling in the target cells; and/or relieve, to some extent, one or more of the symptoms associated with the cancer. To extent the administered compound or composition prevents growth and/or kills existing cancer cells, it may be cytostatic and/or cytotoxic.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

Prodrugs of Compounds of the Disclosure also are included in the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., *Med. Res. Rev.*, 15, 83 (1995)). Specific prodrugs of HDAC inhibitors are discussed in WO 2008/055068.

Compounds of the Disclosure can exist as salts. As used herein, the term "pharmaceutically acceptable salts" refers to salts or zwitterionic forms of the present compounds. Salts of the present compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartarate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. Any reference to compounds of the present disclosure appearing herein is intended to include Compounds of the Disclosure as well as pharmaceutically acceptable salts, solvates, hydrates, or prodrugs thereof.

Compounds of the Disclosure also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies, such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., *Clin. Cancer Res.* (2001) 7:3229).

Compounds of the Disclosure inhibit HDAC and are useful in the treatment of a variety of diseases and conditions. In particular, Compounds of the Disclosure are used in methods of treating a disease or condition wherein inhibition of HDAC provides a benefit, for example, cancers, neurological diseases, neurodegenerative conditions, peripheral neuropathies, autoimmune diseases, inflammatory diseases and conditions, stroke, hypertension, traumatic brain injury, autism, and malaria. The methods comprise administering a therapeutically effective amount of a Compound of the Disclosure to an individual in need thereof.

The present methods also encompass administering a second therapeutic agent to the individual in addition to a Compound of the Disclosure. The second therapeutic agent is selected from agents, such as drugs and adjuvants, known as useful in treating the disease or condition afflicting the individual, e.g., a chemotherapeutic agent and/or radiation known as useful in treating a particular cancer.

Compounds of the Disclosure have been evaluated for their activity at HDAC6 and their selectivity for HDAC6 compared to HDAC1. Selective HDAC6 inhibitors are implicated in a variety of disease states including, but not limited to, arthritis, autoimmune disorders, inflammatory disorders, cancer, neurological diseases such as Rett syndrome, peripheral neuropathies such as CMT, stroke, hypertension, and diseases in which oxidative stress is a causative factor or a result thereof. Also, selective HDAC6 inhibitors, when administered in combination with rapamycin, prolonged the lifespan of mice with kidney xenografts. This model was used to evaluate the immunosuppressant properties of the present compounds and serve as a model of transplant rejection. Furthermore, selective HDAC6 inhibitors confer neuroprotection in rat primary cortical neuron models of oxidative stress. These studies identified selective HDAC6 inhibitors as non-toxic neuroprotective agents.

Compounds of the Disclosure are selective HDAC6 agents having drug-like physiochemical properties.

Thus, in one embodiment, the present disclosure provides a method of treating an individual suffering from a disease or condition, e.g., a disease or condition wherein inhibition of HDAC provides a benefit, the method comprising administering a therapeutically effective amount of a Compound of the Disclosure to an individual in need thereof.

The methods of the present disclosure can be accomplished by administering a Compound of the Disclosure as the neat compound or as a pharmaceutical composition. Administration of a pharmaceutical composition, or a neat Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered.

In some embodiments, a Compound of the Disclosure may be administered in conjunction with a second therapeutic agent useful in the treatment of a disease or condition wherein inhibition of HDAC provides a benefit. The second therapeutic agent is different from a Compound of the Disclosure. A Compound of the Disclosure and the second therapeutic agent can be administered simultaneously or sequentially. In addition, a Compound of the Disclosure and second therapeutic agent can be administered from a single composition or two separate compositions. A Compound of the Disclosure and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present disclosure therefore provides compositions and methods of using a Compound of the Disclosure and, optionally, a second therapeutic agent, in treating diseases or conditions wherein inhibition of HDAC provides a benefit.

The present disclosure also provides pharmaceutical compositions comprising a Compound of the Disclosure and an optional second therapeutic agent useful in the treatment of diseases and conditions wherein inhibition of HDAC provides a benefit.

Further provided are kits comprising a Compound of the Disclosure and, optionally, a second therapeutic agent useful in the treatment of diseases and conditions wherein inhibition of HDAC provides a benefit, packaged separately or together, and an insert having instructions for using these active agents.

A Compound of the Disclosure and the second therapeutic agent can be administered together as a single-unit dose or separately as multi-unit doses, wherein the Compound of the Disclosure is administered before the second therapeutic agent or vice versa. One or more doses of a Compound of the Disclosure and/or one or more doses of the second therapeutic agent can be administered. Compounds of the Disclosure therefore can be used in conjunction with one or more second therapeutic agents, for example, but not limited to, anticancer agents.

Within the meaning of the present disclosure, the term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors of HDAC and can be used in treating diseases and conditions wherein inhibition of HDAC provides a benefit, for example, cancer, a neurological disease, a neurodegenerative condition, traumatic brain injury, stroke, an inflammation, an autoimmune disease, and autism.

In one embodiment, the present disclosure provides methods for treating cancer, including but not limited to killing a cancer cell or neoplastic cell; inhibiting the growth of a cancer cell or neoplastic cell; inhibiting the replication of a cancer cell or neoplastic cell; or ameliorating a symptom thereof, the methods comprising administering to a subject in need thereof an amount of a Compound of the Disclosure, and the pharmaceutically acceptable salts, solvates, e.g., hydrates, and prodrugs thereof, sufficient to treat the cancer. Additionally, it is noted that a selective Compound of the Disclosure may be able to facilitate the killing of cancer cells through reactivation of the immune system by mechanisms relating to the PDI receptor. A Compound of the Disclosure can be used as the sole anticancer agent, or in combination with another anticancer treatment, e.g., radiation, chemotherapy, and surgery.

In another embodiment, the disclosure provides a method for increasing the sensitivity of a cancer cell to the cytotoxic effects of radiotherapy and/or chemotherapy comprising contacting the cell with a Compound of the Disclosure, and the pharmaceutically acceptable salts, solvates, e.g., hydrates, and prodrugs thereof, in an amount sufficient to increase the sensitivity of the cell to the cytotoxic effects of radiotherapy and/or chemotherapy.

In a further embodiment, the present disclosure provides a method for treating cancer comprising: (a) administering to an individual in need thereof an amount of a Compound of the Disclosure; and (b) administering to the individual an amount of radiotherapy, chemotherapy, or both. The amounts administered are each effective to treat cancer. In another embodiment, the amounts are together effective to treat cancer.

This combination therapy of the disclosure can be used accordingly in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated has demonstrated resistance to radiotherapy and/or chemotherapy or is known to be refractory to radiotherapy and/or chemotherapy. A cancer is refractory to a therapy when at least some significant portion of the cancer cells are not killed or their cell division is not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced or has increased.

Other cancers that can be treated with the compounds and methods of the disclosure include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiornyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforma, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myclomonocytic leukemia, acute nonlymphocyctic leukemia, acute undifferentiated leukemia, chronic myclocytic leukemia, chronic lymphocytic leukemia, hairy cell leukemia, and multiple myeloma; acute and chronic leukemias: lymphoblastic, myelogenous, lymphocytic, and myelocytic leukemias; lymphomas: Hodgkin's disease and non-Hodgkin's lymphoma; multiple myeloma; Waldenstrom's macroglobulinemia; heavy chain disease; and polycythemia vera.

Compounds of the Disclosure can also be administered to prevent progression to a neoplastic or malignant state, including but not limited to the cancers listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where chronic irritation or inflammation exists, and often is found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the disclosure. Such characteristics of a transformed phenotype include, for example, morphology changes, looser substratum attachment, loss of contact inhibition, loss of anchorage dependence, protease release, increased sugar transport, decreased serum requirement, expression of fetal antigens, disappearance of the 250,000 dalton cell surface protein.

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present disclosure are also indicated in some viral infections that may lead to cancer. For example, human papilloma virus can lead to cervical cancer (see, e.g., Hernandez-Avila et al., *Archives of Medical Research* (1997) 28:265-271), Epstein-Barr virus (EBV) can lead to lymphoma (see, e.g., Herrmann et al., *J Pathol* (2003) 199(2): 140-5), hepatitis B or C virus can lead to liver carcinoma (see, e.g., El-Serag, *J Clin Gastroenterol* (2002) 35(5 Suppl 2):572-8), human T cell leukemia virus (HTLV)-I can lead to T-cell leukemia (see e.g., Mortreux et al., *Leukemia* (2003) 17(1):26-38), human herpesvirus-8 infection can lead to Kaposi's sarcoma (see, e.g., Kadow et al., *Curr Opin Investig Drugs* (2002) 3(11):1574-9), and Human Immune deficiency Virus (HIV) infection contribute to cancer development as a consequence of immunodeficiency (see, e.g., Dal Maso et al., *Lancet Oncol* (2003) 4(2): 110-9).

In other embodiments, a subject exhibiting one or more of the following predisposing factors for malignancy can be treated by administration of a Compound of the Disclosure and methods of the disclosure: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or procancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W.B. Saunders Co., Philadelphia, pp. 112-113) etc.), and exposure to carcinogens (e.g., smoking, and inhalation of or contacting with certain chemicals).

In another specific embodiment, Compounds of the Disclosure and methods of the disclosure are administered to a human subject to prevent progression of breast, colon, ovarian, or cervical cancer.

In one embodiment, the disclosure provides methods for treating cancer comprising (a) administering to an individual in need thereof an amount of a Compound of the Disclosure; and (b) administering to the individual one or more additional anticancer treatment modality including, but not limited to, radiotherapy, chemotherapy, surgery or immunotherapy, such as a cancer vaccine. In one embodiment, the administering of step (a) is prior to the administering of step (b). In another embodiment, the administering of step (a) is subsequent to the administering of step (b). In still another embodiment, the administering of step (a) is concurrent with the administering of step (b).

In one embodiment, the additional anticancer treatment modality is radiotherapy and/or chemotherapy. In another embodiment, the additional anticancer treatment modality is surgery.

In still another embodiment, the additional anticancer treatment modality is immunotherapy, such as cancer vaccines.

In one embodiment, a Compound of the Disclosure is administered adjunctively with the additional anticancer treatment modality.

In another embodiment, the additional anticancer treatment modality is radiotherapy. In the methods of the present disclosure, any radiotherapy protocol can be used depending upon the type of cancer to be treated. Embodiments of the present disclosure employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

For example, but not by way of limitation, X-ray radiation can be administered; in particular, high-energy megavoltage (radiation of greater than 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present disclosure include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a Compound of the Disclosure, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

In one embodiment, a Compound of the Disclosure is administered prior to the administration of radiotherapy and/or chemotherapy.

In another embodiment, a Compound of the Disclosure is administered adjunctively with radiotherapy and/or chemotherapy.

A Compound of the Disclosure and additional treatment modalities can act additively or synergistically (i.e., the combination of a Compound of the Disclosure and an additional anticancer treatment modality is more effective than their additive effects when each are administered alone). A synergistic combination permits the use of lower dosages of a Compound of the Disclosure and/or the additional treatment modality and/or less frequent administration of a Compound of the Disclosure and/or additional treatment modality to a subject with cancer. The ability to utilize lower dosages of a Compound of the Disclosure and/or an additional treatment modality and/or to administer a compound of the disclosure and the additional treatment modality less frequently can reduce the toxicity associated with the administration without reducing the efficacy of a Compound of the Disclosure and/or the additional treatment modality in the treatment of cancer. In addition, a synergistic effect can result in the improved efficacy of the treatment of cancer and/or the reduction of adverse or unwanted side effects associated with the administration of a Compound of the Disclosure and/or an additional anticancer treatment modality as monotherapy.

In one embodiment, the Compound of the Disclosure may act synergistically with radiotherapy when administered in doses typically employed when such HDACIs are used alone for the treatment of cancer. In another embodiment, the Compound of the Disclosure may act synergistically with radiotherapy when administered in doses that are less than doses typically employed when such HDACIs are used as monotherapy for the treatment of cancer.

In one embodiment, radiotherapy may act synergistically with a Compound of the Disclosure when administered in doses typically employed when radiotherapy is used as monotherapy for the treatment of cancer. In another embodiment, radiotherapy may act synergistically with a compound of the disclosure when administered in doses that are less than doses typically employed when radiotherapy is used as monotherapy for the treatment of cancer.

The effectiveness of the Compounds of the Disclosure as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation, and the survival of the cells monitored. Irradiated cells are plated and cultured for about 14- about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the disclosure.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the $TCD_{50}$ assay.

In vivo assay systems typically use transplantable solid tumor systems in experimental subjects. Radiation survival parameters for normal tissues as well as for tumors can be assayed using in vivo methods known in the art.

The present disclosure provides methods of treating cancers comprising the administration of an effective amount of a Compound of the Disclosure in conjunction with recognized methods of surgery, radiotherapy, and chemotherapies, including, for example, chemical-based mimics of radiotherapy whereby a synergistic enhancement of the effectiveness of the recognized therapy is achieved. The effectiveness of a treatment can be measured in clinical studies or in model systems, such as a tumor model in mice, or cell culture sensitivity assays.

The present disclosure provides combination therapies that result in improved effectiveness and/or reduced toxicity. Accordingly, in one aspect, the disclosure relates to the use of Compounds of the Disclosure as radiosensitizers in conjunction with radiotherapy.

When the combination therapy of the disclosure comprises administering a Compound of the Disclosure with one or more additional anticancer agents, the Compound of the Disclosure and the additional anticancer agents can be administered concurrently or sequentially to an individual. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; any one or a combination of the additional anticancer agents listed below may be administered.

The present disclosure includes methods for treating cancer comprising administering to an individual in need thereof a Compound of the Disclosure and one or more additional anticancer agents or pharmaceutically acceptable salts thereof. A Compound of the Disclosure and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug selected from the group consisting of alkylating agents, nitrogen mustards, cyclophosphamide, trofosfamide, chlorambucil, nitrosoureas, carmustine (BCNU), lomustine (CCNU), alkyl sulphonates, busulfan, treosulfan, triazenes, plant alkaloids, vinca alkaloids (vineristine, vinblastine, vindesine, vinorelbine), taxoids, DNA topoisomcrase inhibitors, epipodophyllins, 9-aminocamptothecin, camptothecin, crisnatol, mitomycins, mitomycin C, anti-metabolites, anti-folates, DHFR inhibitors, trimetrexate, IMP dehydrogenase inhibitors, mycophenolic acid, tiazofurin, ribavirin, EICAR, ribonucleotide reductase inhibitors, hydroxyurea, deferoxamine, pyrimidine analogs, uracil analogs, floxuridine, doxifluridine, ratitrexed, cytosine analogs, cytarabine (ara C), cytosine arabinoside, fludarabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodialdehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivative, all-trans retinoic acid (ATRA-IV), vitamin D3 analogs, El 1089, CB 1093, ICH 1060, photodynamic therapies, verto-porfin, BPD-MA, phthalocyanine, photosensitizer Pc4, demethoxy-hypocrellin A (2BA-2-DMHA), cytokines, interferon-a, interferon-I3, interferon-y, tumor necrosis factor, angiogenesis inhibitors, angiostatin (plasminogen fragment), antiangiogenic antithrombin UI, angiozyme, ABT-627, Bay 12-9566, benefin, bevacizumab, BMS-275291, cartilage-derived inhibitor (CDI), CAI, CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein (IP-10), interleukin-12, kringle 5 (plasminogen fragment), marimastat, metalloproteinase inhibitors (UMPs), 2-methoxyestradiol, MMI 270 (CGS 27023A), MoAb IMC-I C11, neovastat, NM-3, panzem, P1-88, placental ribonuclease inhibitor, plasminogen activator inhibitor, platelet factor-4 (PF4), prinomastat, prolactin 161 (D fragment, proliferin-related protein (PRP), PTK 787/ZK 222594, retinoids, solimastat, squalamine, SS 3304, SU 5416, SU 6668, SU 11248, tetrahydrocortisol-S, tetrathiomolybdate, thalidomide, thrombospondin-1 (TSP-1), TNP-470, transforming growth factor-beta (TGF-11), vasculostatin, vasostatin (calreticulin fragment), ZD 6126, ZD 6474, famesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, 1-methyl-4-phenylpyridinium ion, cell cycle inhibitors, staurosporine, actinomycins, actinomycin D, dactinomycin, bleomycins, bleomycin A2, bleomycin B2, peplomycin, anthracycline, adriamycin, epirubicin, pirarnbicin, zorubicin, mitoxantrone, MDR inhibitors, verapamil, $Ca^{2+}$ATPase inhibitors, and thapsigargin.

Other anti-cancer agents that may be used in the present disclosure include, but are not limited to, acivicin; aclarubicin; acodazole hydrochloride; acronine; adozelesin; aldesleukin; altretamine; arnbomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelcsin; bleomycin sulfate; brequinar sodium; bropirimine; busulfan; cactinomycin; calusterone; caracemide; carbetimer; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mecchlorethamine hydrochloride; megestrol acetate; melengestrol acetate; melphalan; menogaril; mercaptopurine; methotrexate sodium; metoprine; meturedepa; mitindomide; mitocarcin; mitocromin; mitogillin; mitomalcin; mitomycin; mitusper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsornycin; spirogermanium hydrochloride; spiromustine; spiroplatin; streptonigrin; streptozocin; sulofenur; talisomycin; tecogalan sodium; tegafur; teloxantrone hydrochloride; temoporfin; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracit mustard; uredepa; vapreotide; verteporfln; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozolc; zeniplatin; zinostatin; zorubicin hydrochloride.

Further anti-cancer drugs that can be used in the present disclosure include, but are not limited to: 17-AAG; 20-epi-1,25-dihydroxyvitamin D3; 5-ethynyluracil; abiraterone; aclarubicin; acylfulvene; adecypenol; adozelesin; aldesleukin; ALL TK antagonists; altretamine; ambamustine; amidox; arnifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR-ABL antagonists; benzochlorins; benzoylstaurosporine; beta lactam derivatives; beta alethine; beta-clarnycin B; betulinic acid; bFGF inhibitor; bicalutamide; bisantrene; bisaziridinylsperrnine; bisnafide; bistratene A; bizelesin; bortezomib; breflate; bropirimine; budotitane; buthionine sulfoximine; calcipotriol; calphostin C; camptothecin derivatives; canarypox IL-2; carboxamide amino triazole; carboxyarnidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexveraparnil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fltidarabine; fluorodaunoruniein hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubiein; ipomeanol, 4; iroplact; irsogladine; isobengazole; isohomohalicondrin B; itasetron; jasplakinolide; kahalalide F; larnellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anti-cancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum triamine complex; porfimer sodium; porfiromycin; prednisone; acridones; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloaeridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RH retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It is a further aspect of the disclosure that a Compound of the Disclosure can be administered in conjunction with chemical agents that are understood to mimic the effects of radiotherapy and/or that function by direct contact with DNA. Agents for use in combination with a Compound of the Disclosure for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the disclosure provides methods of treatment of cancer using Compounds of the Disclosure as an alternative to chemotherapy alone or radiotherapy alone where the chemotherapy or the radiotherapy has proven or can prove too toxic, e.g., results in unacceptable or unbearable side effects, for the subject being treated. The individual being treated can, optionally, be treated with another anticancer treatment modality such as chemotherapy, surgery, or immunotherapy, depending on which treatment is found to be acceptable or bearable.

Compounds of the Disclosure can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a Compound of the Disclosure effective to eradicate the subject's remaining bone-marrow cell population, then the stem cell graft is infused back into the subject. Supportive care then is provided while bone marrow function is restored and the subject recovers.

The present methods for treating cancer can further comprise the administration of a Compound of the Disclosure and an additional therapeutic agent or pharmaceutically acceptable salts or hydrates thereof. In one embodiment, a composition comprising a Compound of the Disclosure is administered concurrently with the administration of one or more additional therapeutic agent(s), which may be part of the same composition or in a different composition from that comprising the Compound of the Disclosure. In another embodiment, a Compound of the Disclosure is administered prior to or subsequent to administration of another therapeutic agent(s).

In the present methods for treating cancer, the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron.

In one embodiment, the antiemetic agent is granisetron or ondansetron. In another embodiment, the other therapeutic agent may be an hematopoietic colony stimulating factor. Suitable hematopoietic colony stimulating factors include, but are not limited to, filgrastim, sargramostim, molgramostim, and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, and sulindac.

In still another embodiment, the other therapeutic agent may be an anxiolytic agent. Suitable anxiolytic agents include, but are not limited to, buspirene, and benzodiazepines such as diazepam, lorazepam, oxazapam, chlorazepate, clonazepam, chlordiazepoxide and alprazolam.

In addition to treating cancers and sensitizing a cancer cell to the cytotoxic effects of radiotherapy and chemotherapy, Compounds of the Disclosure are used in methods of treating diseases, conditions, and injuries to the central nervous system, such as neurological diseases, neurodegenerative disorders, and traumatic brain injuries (TBIs). In one embodiment, a Compound of the Disclosure HDACI having Formula I is capable of crossing the blood brain barrier to inhibit HDAC in the brain of the individual.

Compounds of the Disclosure also provide a therapeutic benefit in models of peripheral neuropathies, such as CMT. HDAC6 inhibitors have been found to cross the blood nerve barrier and rescue the phenotype observed in transgenic mice exhibiting symptons of distal hereditary motor neuropathy. Administration of HDAC6 inhibitors to symptomatic mice increased acetylated α-tubulin levels, restored proper mitochondrial motility and axonal transport, and increased muscle re-innervation. Other peripheral neuropathies include, but are not limited to, giant axonal neuropathy and various forms of mononeuropathies, polyneuropathies, autonomic neuropathies, and neuritis.

Compounds of the Disclosure are useful for treating a neurological disease by administration of amounts of a Compound of the Disclosure effective to treat the neurological disease or by administration of a pharmaceutical composition comprising amounts of a Compound of the Disclosure effective to treat the neurological disease. The neurological diseases that can be treated include, but are not limited to, Huntington's disease, lupus, schizophrenia, multiple sclerosis, muscular dystrophy, dentatorubralpallidoluysian atrophy (DRRLA), spinal and bulbar muscular atrophy (SBMA), and fine spinocerebellar ataxias (SCA1, SCA2, SCA3/MJD (Machado-Joseph Disease), SCA6, and SCAT), drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's syndrome, tremor, chorea, restless leg syndrome, Parkinson's disease, Parkinsonian syndromes, anxiety, depression, psychosis, manic depression, Friedreich's ataxia, Fragile X syndrome, spinal muscular dystrophy, Rett syndrome, Rubinstein-Taybi syndrome, Wilson's disease, multi-infarct state, CMT, GAN and other peripheral neuropathies.

In an embodiment, the neurological disease treated is Huntington's disease, Parkinson's disease, Alzheimer's disease, spinal muscular atrophy, lupus, or schizophrenia.

Charcot-Marie-Tooth disease (CMT) is one of the most common inherited neurological disorders that affects ~1 in 2,500 people in the US. CMT affects both motor and sensory nerves which may result in foot drop and a high-stepped gait with frequent tripping or falls. Mutations in the small heat-shock protein 27 (HSPB1) cause axonal CMT or distal hereditary motor neuropathy (distal HMN). Expression of mutant HSPB1 decreased acetylated α-tubulin levels and induced severe axonal transport deficits. Pharmacological inhibition of histone deacetylase 6 (HDAC6)-induced α-tubulin deacetylation caused by HDAC6i Tubastatin A corrects the axonal transport defects induced by HSPB1 mutations and rescues the CMT phenotype of symptomatic mutant HSPB1 mice. The pathogenic role of α-tubulin deacetylation has been demonstrated in mutant HSPB1-induced neuropathies and offers valuable perspectives for HDAC6 inhibitors as a therapeutic strategy for hereditary axonopathies. Compounds of the disclosure show potent HDAC6 isoform inhibition, high HDAC6 selectivity, impressive α-tubulin acetylation in various cell lines.

Accordingly, in another embodiment, the neurological disease is Charcot-Marie-Tooth disease.

Compounds of the Disclosure also can be used with a second therapeutic agent in methods of treating conditions, diseases, and injuries to the CNS. Such second therapeutic agents are those drugs known in the art to treat a particular condition, diseases, or injury, for example, but not limited to, lithium in the treatment of mood disorders, estradiol benzoate, and nicotinamide in the treatment of Huntington's disease.

Compounds of the Disclosure also are useful in the treatment of TBIs. Traumatic brain injury (TBI) is a serious and complex injury that occurs in approximately 1.4 million people each year in the United States. TBI is associated with a broad spectrum of symptoms and disabilities, including a risk factor for developing neurodegenerative disorders, such as Alzheimer's disease.

TBI produces a number of pathologies including axonal injury, cell death, contusions, and inflammation. The inflammatory cascade is characterized by proinflammatory cytokines and activation of microglia which can exacerbate other pathologies. Although the role of inflammation in TBI is well established, no efficacious anti-inflammatory therapies are currently available for the treatment of TBI.

Several known HDAC inhibitors have been found to be protective in different cellular and animal models of acute and chronic neurodegenerative injury and disease, for example, Alzheimer's disease, ischemic stroke, multiple sclerosis (MS), Huntington's disease (HD), amyotrophic lateral sclerosis (ALS), spinal muscular atrophy (SMA), and spinal and bulbar muscular atrophy (SBMA). A recent study in experimental pediatric TBI reported a decrease in hippocampal CA3 histone H3 acetylation lasting hours to days after injury. These changes were attributed to documented upstream excitotoxic and stress cascades associated with TBI. HDACIs also have been reported to have anti-inflammatory actions acting through acetylation of non-histone proteins. The HDAC6 selective inhibitor, 4-dimethylamino-N-[5-(2-mercaptoacetylamino)pentyl]benzamide (DMA-PB), was found to be able to increase histone H3 acetylation and reduce microglia inflammatory response following traumatic brain injury in rats, which demonstrates the utility of HDACIs as therapeutics for inhibiting neuroinflammation associated with TBI.

Compounds of the Disclosure therefore also are useful in the treatment of inflammation and strokes, and in the treatment of autism and autism spectrum disorders. Compounds of the Disclosure further can be used to treat parasitic infections, (e.g., malaria, toxoplasmosis, trypanosomiasis, helminthiasis, protozoal infections (see Andrews et al. *Int. J. Parasitol.* 2000, 30(6), 761-768).

In certain embodiments, the compound of the disclosure can be used to treat malaria. Compounds of the Disclosure can be co-administered with an antimalarial compound selected from the group consisting of aryl amino alcohols, cinchona alkaloids, 4-aminoquinolines, type 1 or type 2 folate synthesis inhibitors, 8-aminoquinolines, antimicrobials, peroxides, naphthoquinones, and iron chelating agents. The antimalarial compound can be, but is not limited to, quinine, quinidine, mefloquine, halfantrine, chloroquine, amodiaquine, proguanil, chloroproquanil, pyrimethamine, primaquine, 8-[(4-amino-1-methylbutyl)amino]-2,6-dimethoxy-4-methyl-5-[(3-trifluoromethyl)phenoxy]quinoline succinate (WR238,605), tetracycline, doxycycline, clindamycin, azithromycin, fluoroquinolones, artemether, areether, artesunate, artelinic acid, atovaquone, and deferrioxamine. In one embodiment, the antimalarial compound is chloroquine.

Compounds of the Disclosure also can be used as imaging agents. In particular, by providing a radiolabeled, isotopically labeled, or fluorescently-labeled HDACI, the labeled compound can image HDACs, tissues expressing HDACs, and tumors. Labeled Compound of the Disclosure also can image patients suffering from a cancer, or other HDAC-mediated diseases, e.g., stroke, by administration of an effective amount of the labeled compound or a composition containing the labeled compound. In one embodiment, the labeled HDACI is capable of emitting positron radiation and is suitable for use in positron emission tomography (PET). Typically, a labeled Compound of the Disclosure is used to identify areas of tissues or targets that express high concentrations of HDACs. The extent of accumulation of labeled HDACI can be quantified using known methods for quantifying radioactive emissions. In addition, the labeled HDACI can contain a fluorophore or similar reporter capable of tracking the movement of particular HDAC isoforms or organelles in vitro.

Compounds of the Disclosure useful in the imaging methods contain one or more radioisotopes capable of emitting one or more forms of radiation suitable for detection by any standard radiology equipment, such as PET, SPECT, gamma cameras, Mill, and similar apparatus. Isotopes include tritium ($^3$H) and carbon ($^{11}$C). The HDACIs of the present disclosure also can contain isotopes of fluorine ($^{18}$F) and iodine ($^{123}$I) for imaging methods. Typically, a labeled Compound of the Disclosure contains an alkyl group having a $^{11}$C label, i.e., a $^{11}$C-methyl group, or an alkyl group substituted with 18F, $^{123}$I, $^{125}$I, $^{131}$I, or a combination thereof.

Fluorescently-labeled Compounds of the Disclosure also can be used in the imaging method of the present disclosure. Such compounds have an FITC, carbocyamine moiety or other fluorophore which will allow visualization of the HDAC proteins in vitro.

The labeled Compounds of the Disclosure and methods of use can be in vivo, and particularly on humans, and for in vitro applications, such as diagnostic and research applications, using body fluids and cell samples. Imaging methods are discussed in WO 03/060523. Typically, the method comprises contacting cells or tissues with a radiolabeled, isotopically labeled, fluorescently labeled, or tagged (such as biotin tagged) compound of the disclosure, and making a radiographic, fluorescent, or similar type of image depending on the visualization method employed, i.e., in regared to radiographic images, a sufficient amount to provide about 1 to about 30 mCi of the radiolabeled compound.

Imaging methods include the use of labeled Compounds of the Disclosure which are capable of generating at least a 2:1 target to background ratio of radiation intensity, or about 5:1, about 10:1, or about 15:1 ratio of radiation intensity between target and background.

In some methods, the labeled Compounds of the Disclosure are excreted from tissues of the body quickly to prevent prolonged exposure to the radiation of the radiolabeled compound administered to the individual. In some embodiments, labeled Compounds of the Disclosure are eliminated from the body in less than about 24 hours. In some embodiments, labeled Compounds of the Disclosure are eliminated from the body in less than about 16 hours, 12 hours, 8 hours, 6 hours, 4 hours, 2 hours, 90 minutes, or 60 minutes. In some embodiments, labeled Compounds of the Disclosure are eliminated in about 60 to about 120 minutes.

In addition to isotopically labeled and fluorescently labeled derivatives, the present disclosure also embodies the use of derivatives containing tags (such as biotin) for the identification of biomolecules associated with the HDAC isoforms of interest for diagnostic, therapeutic or research purposes.

Compounds of the Disclosure also are useful in the treatment of autoimmune diseases and inflammations. Compounds of the present disclosure are particularly useful in overcoming graft and transplant rejections and in treating forms of arthritis.

Despite successes of modern transplant programs, the nephrotoxicity, cardiovascular disease, diabetes, and hyperlipidemia associated with current therapeutic regimens, plus the incidence of post-transplant malignancies and graft loss from chronic rejection, drive efforts to achieve long-term allograft function in association with minimal immunosuppression. Likewise, the incidence of inflammatory bowel disease (IBD), including Crohn's disease and ulcerative colitis, is increasing. Animal studies have shown that T regulatory cells (Tregs) expressing the forkhead transcription family member, Foxp3, are key to limiting autoreactive and alloreactive immunity. Moreover, after their induction by costimulation blockade, immunosuppression, or other strategies, Tregs may be adoptively transferred to naïve hosts to achieve beneficial therapeutic effects. However, attempts to develop sufficient Tregs that maintain their suppressive functions post-transfer in clinical trials have failed. Murine studies show that HDACIs limit immune responses, at least in significant part, by increasing Treg suppressive functions, (R. Tao et al., *Nat Med,* 13, 1299-1307, (2007)), and that selective targeting of HDAC6 is especially efficacious in this regard.

With organ transplantation, rejection begins to develop in the days immediately post-transplant, such that prevention rather than treatment of rejection is a paramount consideration. The reverse applies in autoimmunity, wherein a patient presents with the disease already causing problems. Accordingly, HDAC6−/− mice treated for 14 days with low-dose RPM (rapamycin) are assessed for displaying signs of tolerance induction and resistance to the development of chronic rejection, a continuing major loss of graft function long-term in the clinical transplant population. Tolerance is assessed by testing whether mice with long-surviving allografts reject a subsequent third-party cardiac graft and accept additional donor allografts without any immunosuppression, as can occur using a non-selective HDACI plus RPM. These in vivo stuides are accompanied by assessment of ELISPOT and MLR activities using recipient lymphocytes challenged with donor cells. Protection against chronic rejection is assessed by analysis of host anti-donor humoral responses and analysis of graft transplant arteriosclerosis and interstitial fibrosis in long-surviving allograft recipients.

The importance of HDAC6 targeting is assessed in additional transplant models seeking readouts of biochemical significance, as is monitored clinically. Thus, the effects of HDAC6 in targeting in renal transplant recipients (monitoring BUN, proteinuria) and islet allografts (monitoring blood glucose levels) are assessed. Renal transplants are the most common organ transplants performed, and the kidney performs multiple functions, e.g., regulating acid/base metabolism, blood pressure, red cell production, such that efficacy in this model indicates the utility of HDAC6 targeting. Likewise, islet transplantation is a major unmet need given that clinical islet allografts are typically lost after the first one or two years post-transplant. Having a safe and non-toxic means to extend islet survival without maintenance CNI therapy would be an important advance. Transplant studies also are strengthened by use of mice with foxed HDAC6. Using existing Foxp3-Cre mice, for example, the effects of deletion of HDAC6 just in Tregs is tested. This approach can be extended to targeting of HDAC6 in T cells (CD4-Cre) and dendritic cells (CD11c-Cre), for example. Using tamoxifen-regulated Cre, the importance of HDAC6 in induction vs. maintenance of transplants (with implications for short-term vs. maintenance HDAC6I therapy) is assessed by administering tamoxifen and inducing HDAC6 deletion at varying periods post-transplant.

Studies of autoimmunity also are undertaken. In this case, interruption of existing disease is especially important and HDAC6 targeting can be efficacious without any requirement for additional therapy (in contrast to a need for brief low-dose RPM in the very aggressive, fully MHC-mismatched transplant models). Studies in mice with colitis indicated that HDAC6−/− Tregs were more effective than WT Tregs in regulating disease, and tubacin was able to rescue mice if treatment was begun once colitis had developed. These studies are extended by assessing whether deletion of HDAC6 in Tregs (Foxp3/Cre) vs. T cells (CD4=Cre) vs. DC (CD11c-Cre) differentially affect the development and severity of colitis. Similarly, control of colitis is assessed by inducing HDAC6 deletion at varying intervals after the onset of colitis with tamoxifen-regulated Cre.

The present compounds are envisioned to demonstrate anti-arthritic efficacy in a collagen-induced arthritis model in DBA1/J mice. In this test, DBA1/J mice (male, 7-8 weeks) are used, with 8 animals per group. Systemic arthritis is induced with bovine collagen type II and CFA, plus an IFA booster injection on day 21. A Compound of the Disclosure is dosed at 50 mg/kg and 100 mg/kg on day 28 for 2 consecutive weeks, and the effects determined from the Average Arthritic Score vs. Days of Treatment data.

Despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin, and corticosteroids.

Compounds of the Disclosure may be used as immunosuppressive agents that suppress humoral immunity and cell-mediated immune reactions, such as allograft rejection, delayed hypersensitivity, experimental allergic encephalomyelitis, Freund's adjuvant arthritis and graft versus host disease. Compounds of the Disclosure are useful for the prophylaxis of organ rejection subsequent to organ transplantation, for treatment of rheumatoid arthritis, for the treatment of psoriasis, and for the treatment of other autoimmune diseases, such as type I diabetes, Crohn's disease, and lupus.

A therapeutically effective amount of a Compound of the Disclosure can be used for immunosuppression including, for example, to prevent organ rejection or graft vs. host disease, and to treat diseases and conditions, in particular, autoimmune and inflammatory diseases and conditions. Examples of autoimmune and inflammatory diseases include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronic progrediente, and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, and glomerulonephritis.

A Compounds of the Disclosure can be used alone, or in conjunction with a second therapeutic agent known to be useful in the treatment of autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, and particularly HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present disclosure.

In the present method, a therapeutically effective amount of one or more Compounds of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of Compounds of the Disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg of body weight. The dosage of a composition may be at any dosage including, but not limited to, about 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

A Compound of the Disclosure used in a method of the present disclosure typically is administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and auxiliaries that facilitate processing of a Compound of the Disclosure.

The term "carrier" refers to a diluent, adjuvant, or excipient, with which a Compound of the Disclosure is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a carrier when a Compound of the Disclosure is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

The present disclosure encompasses the preparation and use of solvates of a Compound of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A Compound of the Disclosure can be infused with other fluids over a 10-30 minute span or over several hours.

Compounds of the Disclosure can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compounds of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, a Compound of the Disclosure also can be formulated as a depot preparation. Such long-acting formulations can be administered by implantation (for example, subcutaneously or intramuscularly) or by intramuscular injection. Thus, for example, a Compound of the Disclosure can be formulated with suitable polymeric or hydrophobic materials (for example, as an emulsion in an acceptable oil) or ion exchange resins.

In particular, a Compound of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compounds of the Disclosure also can be injected parenterally, for example, intravenously, intramuscularly, subcutaneously, or intracoronarily. For parenteral administration, Compounds of the Disclosure are best used in the form of a sterile aqueous solution which can contain other substances, for example, salts or monosaccharides, such as mannitol or glucose, to make the solution isotonic with blood.

As an additional embodiment, the present disclosure includes kits which comprise one or more compounds or compositions packaged in a manner that facilitates their use to practice methods of the disclosure. In one simple embodiment, the kit includes a compound or composition described herein as useful for practice of a method (e.g., a composition comprising a Compound of the Disclosure and an optional second therapeutic agent), packaged in a container, such as a sealed bottle or vessel, with a label affixed to the container or included in the kit that describes use of the compound or composition to practice the method of the disclosure. Preferably, the compound or composition is packaged in a unit

75 dosage form. The kit further can include a device suitable for administering the composition according to the intended route of administration, for example, a syringe, drip bag, or patch. In another embodiment, the present compounds is a lyophilate. In this instance, the kit can further comprise an additional container which contains a solution useful for the reconstruction of the lyophilate.

Compounds of the Disclosure demonstrate an increased HDAC6 potency and selectivity against HDAC1 and HDAC8 with improvements in BEI relative to prior compounds. The improved properties of the present compounds, particularly the increase in BEI and reduced potency at HDAC8, indicate that the present compounds are useful for applications such as, but not limited to, immunosuppresssive and neuroprotective agents. For example, compounds of the present disclosure typically have a bonding affinity ($IC_{50}$) to HDAC6 of less than 100 μM, less than 25 μM, less than 10 μM, less than 1 μM, less than 0.5 μM, and less than 0.2 μM.

EXAMPLES

General Synthetic Methods and Procedures

All starting materials and solvents were purchased from commercial suppliers at reagent purity and, unless otherwise noted, were used as obtained without any further purification. Dry solvents used as media in moisture-sensitive reactions were purchased from Sigma-Aldrich at anhydrous grade and handled under argon. All reactions were carried out in dry conditions, under inert (argon) atmosphere. Microwave reactions were run in a Biotage Initiator microwave reactor. Reactions were monitored by thin layer chromatography on silica gel-coated glass plates (TLC LuxPlate Silica gel 60 $F_{254}$, Merck), with visualization at 254 nm, and/or using appropriate dyes. Where indicated, synthetic intermediates were purified by 230-400 mesh silica gel flash chromatography on a CombiFlash system, using appropriate solvent mixtures. Final products were purified by preparative HPLC using a Shimadzu preparative liquid chromatograph [ACE 5AQ (150×21.2 mm) with 5 μm particle size. Method 1: 25-100% MeOH/$H_2O$, 30 min; 100% MeOH, 5 min; 100-25% MeOH/$H_2O$, 4 min. Method 2: 8-100% MeOH/$H_2O$, 30 min; 100% MeOH, 5 min; 100-8% MeOH/$H_2O$, 4 min. Method 3: 0% MeOH, 5 min; 0-100% MeOH/$H_2O$, 25 min; 100% MeOH, 5 min; 100-0% MeOH/$H_2O$, 4 min. Flow rate=17 mL/min], with monitoring at 254 and 280 nm. Both solvents were spiked with 0.05% TFA. $^1H$ and $^{13}C$ NMR spectra were recorded at 400 MHz and 100.6 MHz, respectively, on Bruker DPX-400 or AVANCE-400 spectrometers. Chemical shifts (δ scale) are reported in parts per million (ppm) relative to TMS. $^1H$ NMR spectra are reported in this order: multiplicity and number of protons; signals were characterized as: s (singlet), d (doublet), dd (doublet of doublets), t (triplet), m (multiplet), bs (broad signal). HRMS spectra were recorded using ESI with an LCMS-IT-TOF (Shimadzu). Purity of all final compounds was determined by analytical HPLC [ACE 3AQ $C_{18}$ column (150×4.6 mm, particle size 3 μM); 0.05% TFA in $H_2O$/0.05% TFA in MeOH gradient eluting system; flow rate=1.0 mL/min]. All compounds were tested at >95% purity as determined by HPLC analysis.

76

Example 1

Synthesis of 5-(2-Benzamidoethyl)-N-hydroxy-isoxazole-3-carboxamide

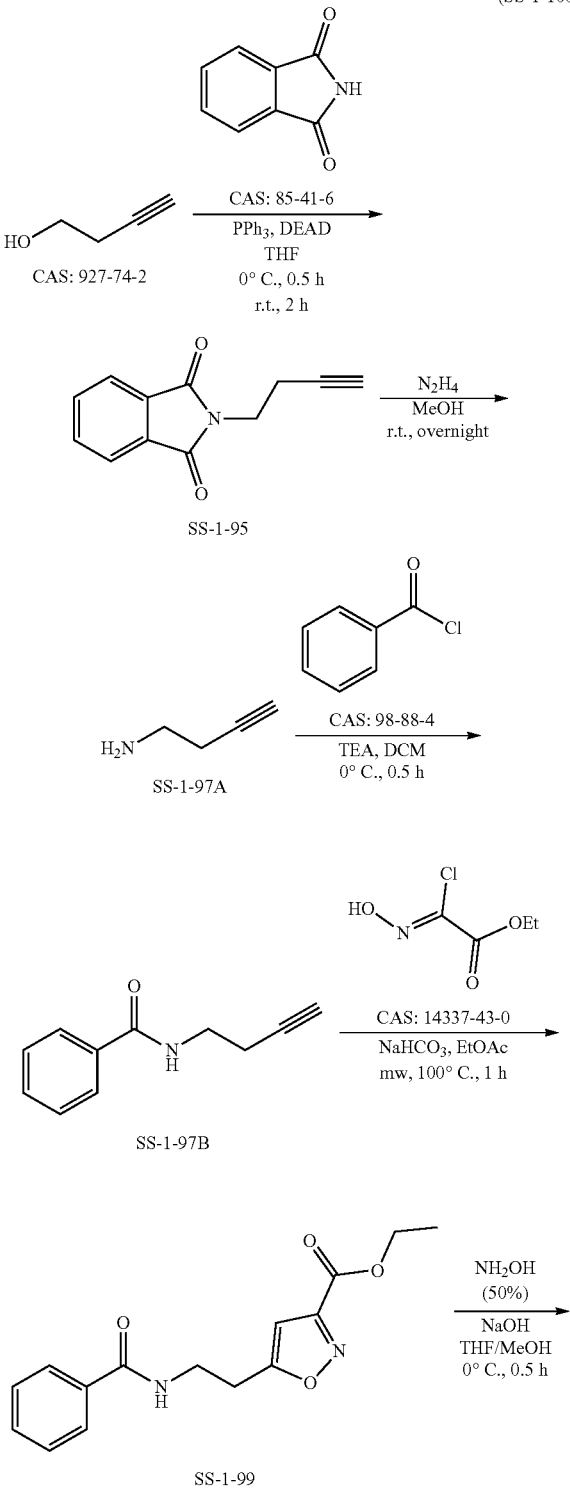

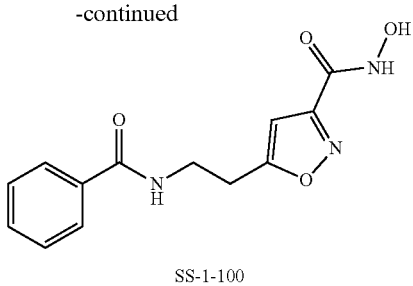

SS-1-100

SS-1-95: To a stirred solution of 3-butyn-1-ol (140 mg, 2.0 mmol), phthalimide (382 mg, 2.6 mmol), and PPh₃ (682 mg, 2.6 mmol) was added DEAD (525 mg, 2.6 mmol) at 0° C. under Ar protection. The resulting mixture was slowly warmed up to room temperature and stirred at the same temperature for 2.5 h. Then the reaction was quenched with H₂O, and extracted with EtOAc (3×20 mL). The combined organic extracts were washed with brine (40 mL), dried over sodium sulfate, and concentrated under vacuum. The crude product was purified by flash chromatography (0-50% EtOAc/Hexene), and the title compound was obtained as white powder (370 mg, 93%). $^1$H NMR (400 MHz, CDCl₃) δ 7.86 (dd, J=5.5, 3.0 Hz, 2H), 7.73 (dd, J=5.5, 3.0 Hz, 2H), 3.89 (t, J=7.1 Hz, 2H), 2.62 (td, J=7.1, 2.7 Hz, 2H), 1.96 (t, J=2.7 Hz, 1H). $^{13}$C NMR (100 MHz, CDCl₃) δ 168.04, 134.05, 132.01, 123.39, 80.27, 70.26, 36.55, 18.36.

SS-1-97B: To a stirred solution of SS-1-95 (180 mg, 0.9 mmol) in MeOH (5 mL) was added N₂H₄ (0.06 mL, 1.13 mmol). The resulting mixture was stirred at room temperature for 16 h. Then participate was filtered off, and the filtrate was quenched with water (5 mL), and acidified to pH 2 with 2 N HCl. The solution was concentrated under vacuum to afford SS-1-97A as white powder. The crude product was used directly into the next step. To a stirred solution of SS-1-97A in DCM (5 mL) was added TEA (0.37 mL, 2.7 mmol) and benzoyl chloride (252 mg, 1.8 mmol) at 0° C. Then the resulting mixture was stirred at the same temperature for 30 min. The reaction was quenched with water (5 mL), and extracted with DCM (3×10 mL). The combined organic extracts were washed with brine (40 mL), dried over sodium sulfate, and concentrated under vacuum. The crude product was purified by flash chromatography (0-50% EtOAc/Hexene), and the title compound was obtained as white powder (140 mg, 90%). $^1$H NMR (400 MHz, Acetone-d₆) δ 7.93 (dd, J=5.3, 3.2 Hz, 3H), 7.58-7.53 (m, 1H), 7.49 (dd, J=8.1, 6.6 Hz, 2H), 3.57 (td, J=7.1, 6.0 Hz, 2H), 2.55 (td, J=7.1, 2.7 Hz, 2H), 2.43 (t, J=2.7 Hz, 1H).

SS-1-99: To a solution of SS-1-97B (140 mg, 0.8 mmol) in EtOAc (2 mL) were added NaHCO₃ (201 mg, 2.4 mmol) and Ethyl 2-chloro-2-(hydroxyimino)acetate (367 mg, 2.4 mmol) in a microwave reaction tube. The mixture was heated at 100° C. for 1 h in a microwave reactor. After completion of the reaction, precipitate solid was filtered off and the filtrate was concentrated under reduced pressure. The crude product was purified by flash chromatography (0-50% EtOAc/Hexene), and the title compound was obtained as colorless oil (140 mg, 61%). $^1$H NMR (400 MHz, CDCl₃) δ 7.73 (dd, J=5.2, 3.2 Hz, 2H), 7.50 (ddd, J=6.6, 3.9, 1.3 Hz, 1H), 7.46-7.36 (m, 2H), 6.51 (s, 2H), 4.42 (q, J=7.1 Hz, 2H), 3.82 (q, J=6.4 Hz, 2H), 3.19 (t, J=6.5 Hz, 2H), 1.40 (t, J=7.1 Hz, 3H). $^{13}$C NMR (100 MHz, CDCl₃) δ 172.65, 167.78, 159.92, 156.62, 134.05, 131.76, 128.67, 126.91, 102.74, 62.21, 37.89, 27.16, 14.13.

SS-1-100: In a round bottom flask, NaOH (160 mg, 4.0 mmol) was dissolved in 50% aqueous NH₂OH (1.6 mL, approx. 50 equiv) at 0° C. A solution of SS-1-99 (140 mg, 0.5 mmol) in 1:1 THF/MeOH (6 mL) was added dropwise, and stirring was continued for 30 min while warming to room temperature. The solution was neutralized with 6N HCl and extracted with EtOAc (3×15 mL). The organic layers were separated, washed with brine, dried over Na₂SO₄, and concentrated under vacuum. The crude product was washed with EtOAc to afford the desired product as white powder (60 mg, 43%). $^1$H NMR (400 MHz, DMSO-d₆) δ 8.68 (t, J=5.5 Hz, 1H), 7.81 (d, J=7.1 Hz, 2H), 7.53 (t, J=7.3 Hz, 1H), 7.46 (t, J=7.3 Hz, 2H), 6.63 (s, 1H), 3.60 (q, J=6.6 Hz, 2H), 3.09 (t, J=6.7 Hz, 2H). $^{13}$C NMR (100 MHz, DMSO-d₆) δ 172.44, 166.42, 157.44, 156.17, 134.28, 131.25, 128.31 (2C), 127.12 (2C), 101.13, 37.22, 26.29. ESI HRMS calc. for $C_{13}H_{14}N_3O_4$: [M+H]⁺, m/z 276.0979; found: 276.0984.

Example 2

Synthesis of 5-(2-(3,4-dichlorobenzamido)ethyl)-N-hydroxyisoxazole-3-carboxamide

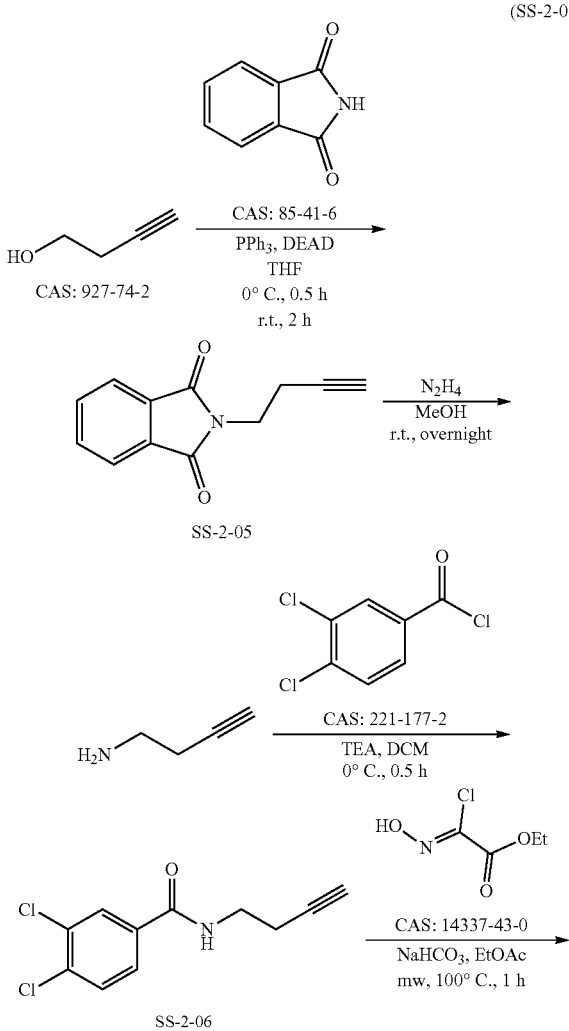

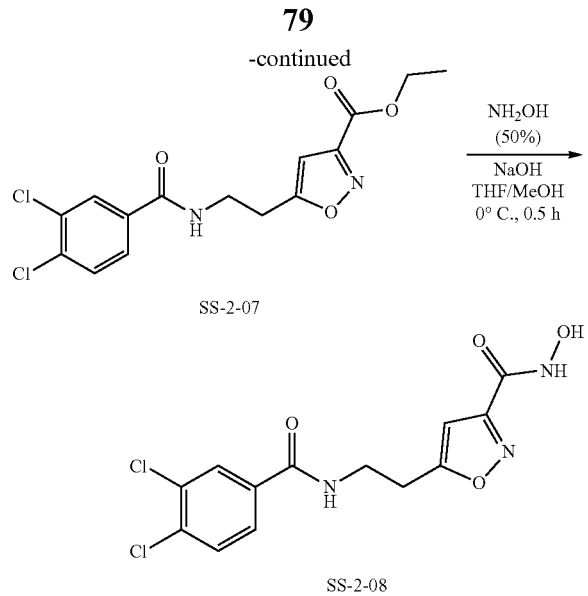

SS-2-05: To a stirred solution of 3-butyn-1-ol (140 mg, 2.0 mmol), phthalimide (382 mg, 2.6 mmol), and PPh₃ (682 mg, 2.6 mmol) was added DEAD (525 mg, 2.6 mmol) at 0° C. under Ar protection. The resulting mixture was slowly warmed up to room temperature and stirred at the same temperature for 2.5 h. Then the reaction was quenched with H₂O, and extracted with EtOAc (3×20 mL). The combined organic extracts were washed with brine (40 mL), dried over sodium sulfate, and concentrated under vacuum. The crude product was purified by flash chromatography (0-50% EtOAc/Hexene), and the title compound was obtained as white powder (260 mg, 65%).

SS-2-06: To a stirred solution of SS-2-05 (260 mg, 1.3 mmol) in MeOH (5 mL) was added N2H4 (0.1 mL, 3.2 mmol). The resulting mixture was stirred at room temperature for 16 h. Then participate was filtered off, and the filtrate was quenched with water (5 mL), acidified to pH 2 with 2 N HCl. The solution was concentrated under vacuum to afford the desired product as white powder. The crude product was used directly in the next step. To a stirred solution of the intermediate in DCM (5 mL) was added TEA (0.54 mL, 3.9 mmol) and 3,4-Dichlorobenzoyl chloride (543 mg, 2.6 mmol) at 0° C. Then the resulting mixture was stirred at the same temperature for 30 min. The reaction was quenched with water (5 mL), and extracted with DCM (3×10 mL). The combined organic extracts were washed with brine (40 mL), dried over sodium sulfate, and concentrated under vacuum. The crude product was purified by flash chromatography (0-50% EtOAc/Hexene), and the title compound was obtained as colorless solid (220 mg, 70%). $^1$H NMR (400 MHz, CDCl₃) δ 7.88 (d, J=2.0 Hz, 1H), 7.60 (dd, J=8.3, 2.1 Hz, 1H), 7.52 (d, J=8.3 Hz, 1H), 6.41 (s, 1H), 3.61 (q, J=6.2 Hz, 2H), 2.53 (td, J=6.3, 2.6 Hz, 2H), 2.07 (t, J=2.6 Hz, 1H).

SS-2-07: To a solution of SS-2-06 (220 mg, 0.9 mmol) in EtOAc (2 mL) were added NaHCO₃ (227 mg, 2.7 mmol) and Ethyl 2-chloro-2-(hydroxyimino)acetate (408 mg, 2.7 mmol) in a microwave reaction tube. The mixture was heated at 100° C. for 1 h in a microwave reactor. After completion of the reaction, precipitate solid was filtered off and the filtrate was concentrated under reduced pressure. The crude product was purified by flash chromatography (0-80% EtOAc/Hexene), and the title compound was obtained as white solid (250 mg, 78%). $^1$H NMR (400 MHz, DMSO-d₆) δ 8.85 (t, J=5.5 Hz, 1H), 8.03 (d, J=1.4 Hz, 1H), 7.82-7.71 (m, 2H), 6.76 (s, 1H), 4.34 (q, J=7.1 Hz, 2H), 3.60 (q, J=6.5 Hz, 2H), 3.11 (t, J=6.7 Hz, 2H), 1.30 (t, J=7.1 Hz, 3H). $^{13}$C NMR (100 MHz, DMSO-d₆) δ 173.53, 164.23, 159.60, 156.10, 134.60, 134.17, 131.34, 130.84, 129.16, 127.54, 102.46, 61.80, 37.40, 26.31, 14.01.

SS-2-08: In a round bottom flask, NaOH (224 mg, 5.6 mmol) was dissolved in 50% aqueous NH₂OH (2.0 mL, approx. 50 equiv) at 0° C. A solution of SS-1-99 (250 mg, 0.7 mmol) in 1:1 THF/MeOH (10 mL) was added dropwise, and stirring was continued for 30 min while warming to room temperature. The solution was neutralized with 6N HCl and extracted with EtOAc (3×15 mL). The organic layers were separated, washed with brine, dried over Na₂SO₄, and concentrated under vacuum. The crude product was washed with Et₂O/EtOAc (10:1) to afford the desired product as white powder (70 mg, 29%). $^1$H NMR (400 MHz, DMSO-d₆) δ 11.46 (s, 1H), 9.33 (s, 1H), 8.87 (t, J=5.3 Hz, 1H), 8.04 (d, J=1.6 Hz, 1H), 7.83-7.72 (m, 2H), 6.63 (s, 1H), 3.59 (q, J=6.4 Hz, 2H), 3.09 (t, J=6.8 Hz, 2H). $^{13}$C NMR (100 MHz, DMSO-d₆) δ 172.27, 164.14, 157.44, 156.18, 134.53, 134.10, 131.28, 130.76, 129.11, 127.48, 101.20, 37.40, 26.13. ESI HRMS calc. for $C_{13}H_{12}C_{12}N_3O_4$: [M+H]⁺, m/z 344.0205; found: 344.0198.

Example 3

Synthesis of 5-(2-(2-naphthamido)ethyl)-N-hydroxyisoxazole-3-carboxamide

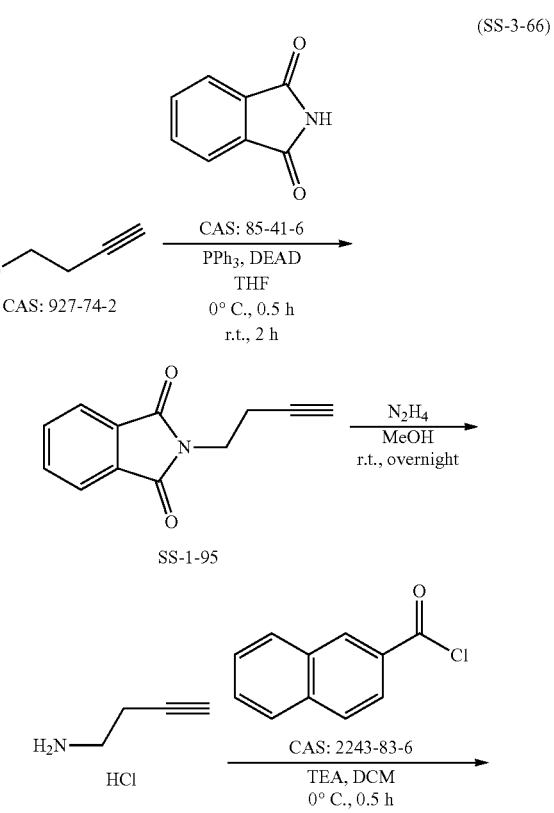

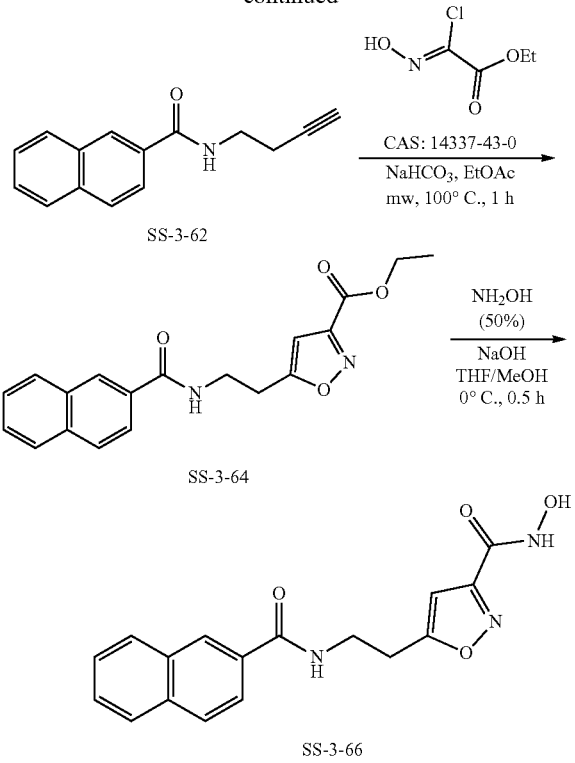

Synthesis of 2-(but-3-yn-1-yl)isoindoline-1,3-dione (SS-1-95): To a stirred solution of 3-butyn-1-ol (140 mg, 2.0 mmol), phthalimide (382 mg, 2.6 mmol), and PPh₃ (682 mg, 2.6 mmol) was added DEAD (525 mg, 2.6 mmol) at 0° C. under Ar protection. The resulting mixture was slowly warmed up to room temperature and stirred at the same temperature for 2.5 h. Then the reaction was quenched with H₂O, and extracted with EtOAc (3×20 mL). The combined organic extracts were washed with brine (40 mL), dried over sodium sulfate, and concentrated under vacuum. The crude product was purified by flash chromatography (0-50% EtOAc/hexane), and the title compound was obtained as white powder (370 mg, 93%). $^1$H NMR (400 MHz, CDCl₃) δ 7.86 (dd, J=5.5, 3.0 Hz, 2H), 7.73 (dd, J=5.5, 3.0 Hz, 2H), 3.89 (t, J=7.1 Hz, 2H), 2.62 (td, J=7.1, 2.7 Hz, 2H), 1.96 (t, J=2.7 Hz, 1H). $^{13}$C NMR (100 MHz, CDCl₃) δ 168.0, 134.1, 132.0, 123.4, 80.3, 70.3, 36.6, 18.4.

Synthesis of N-(but-3-yn-1-yl)-2-naphthamide (SS-3-62): To a stirred solution of SS-1-95 (215 mg, 1.08 mmol) in MeOH (5 mL) was added N₂H₄ (0.1 mL, 2.7 mmol). The resulting mixture was stirred at room temperature for 16 h. Then participate was filtered off, and the filtrate was quenched with water (5 mL), acidified to pH 2 with 2 N HCl. The solution was concentrated under vacuum to afford SS-1-97A as white powder. The crude product was used directly into the next step. To a stirred solution of SS-1-97A in DCM (5 mL) was added TEA (0.25 mL, 1.6 mmol) and 2-naphthoyl chloride (246 mg, 1.3 mmol) at 0° C. Then the resulting mixture was stirred at the same temperature for 30 min. The reaction was quenched with water (5 mL), and extracted with DCM (3×10 mL). The combined organic extracts were washed with brine (40 mL), dried over sodium sulfate, and concentrated under vacuum. The crude product was purified by flash chromatography (0-30% EtOAc/hexane), and the title compound was obtained as white powder (170 mg, 70%, crude).

Synthesis of ethyl 5-(2-(2-naphthamido)ethyl)isoxazole-3-carboxylate (SS-2-64): To a solution of SS-2-62 (170 mg, 0.76 mmol) in EtOAc (2 mL) were added NaHCO₃ (191 mg, 2.28 mmol) and ethyl 2-chloro-2-(hydroxyimino)acetate (344 mg, 2.28 mmol) in a microwave reaction tube. The mixture was heated at 100° C. for 1 h in a microwave reactor. After completion of the reaction, precipitate solid was filtered off and the filtrate was concentrated under reduced pressure. The crude product was purified by flash chromatography (0-50% EtOAc/hexane), and the title compound was obtained as white solid (150 mg, 58%). $^1$H NMR (400 MHz, CDCl₃) δ 8.25 (s, 1H), 7.86-7.77 (m, 4H), 7.57-7.45 (m, 2H), 6.90 (t, J=5.7 Hz, 1H), 6.50 (s, 1H), 4.38 (q, J=7.1 Hz, 2H), 3.85 (q, J=6.5 Hz, 2H), 3.20 (t, J=6.6 Hz, 2H), 1.36 (t, J=7.1 Hz, 3H). $^{13}$C NMR (100 MHz, CDCl₃) δ 172.8, 168.0, 160.02, 156.7, 134.9, 132.7, 131.3, 129.0, 128.6, 127.9, 127.8, 127.6, 126.9, 123.6, 102.8, 62.3, 38.1, 27.3, 14.2.

Synthesis of 5-(2-(2-naphthamido)ethyl)-N-hydroxy-isoxazole-3-carboxamide (SS-3-66): In a round bottom flask, NaOH (142 mg, 3.55 mmol) was dissolved in 50% aqueous NH₂OH (1.4 mL, approx. 50 equiv) at 0° C. A solution of SS-3-64 (150 mg, 0.44 mmol) in 1:1 THF/MeOH (5 mL) was added dropwise, and stirring was continued for 30 min while warming to room temperature. The solution was neutralized with 6N HCl and extracted with EtOAc (3×10 mL). The organic layers were separated, washed with brine, dried over Na₂SO₄, and concentrated under vacuum. The crude product was purified by flash chromatography (0-10% MeOH/DCM) and prep-HPLC (Method 2) and lyophilized to afford the desired product as white powder (15 mg, 10%). $^1$H NMR (400 MHz, DMSO-d₆) δ 11.45 (br s, 1H), 9.33 (br s, 1H), 8.85 (t, J=5.2 Hz, 1H), 8.41 (s, 1H), 8.03-7.88 (m, 3H), 7.90 (d, J=8.6 Hz, 1H), 7.63-7.57 (m, 2H), 6.66 (s, 1H), 3.66 (q, J=6.5 Hz, 2H), 3.14 (t, J=6.7 Hz, 2H). ESI HRMS calc. for C₁₇H₁₆N₃O₄: [M+H]⁺, m/z 326.1135; found: 326.1137.

Example 4

Synthesis of 5-(2-([1,1'-biphenyl]-3-carboxamido)ethyl)-N-hydroxyisoxazole-3-carboxamide

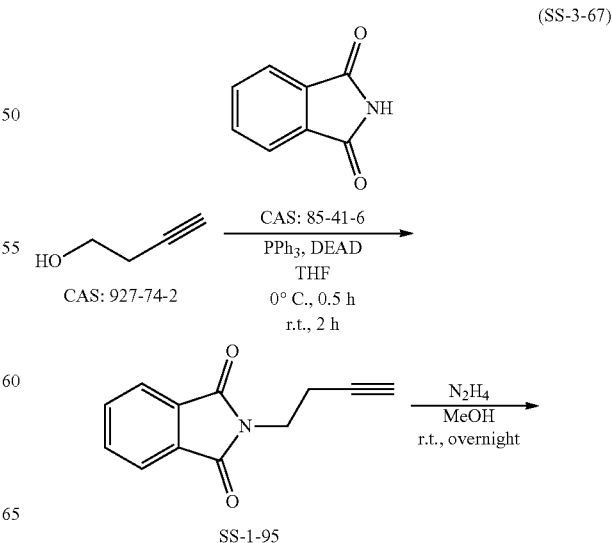

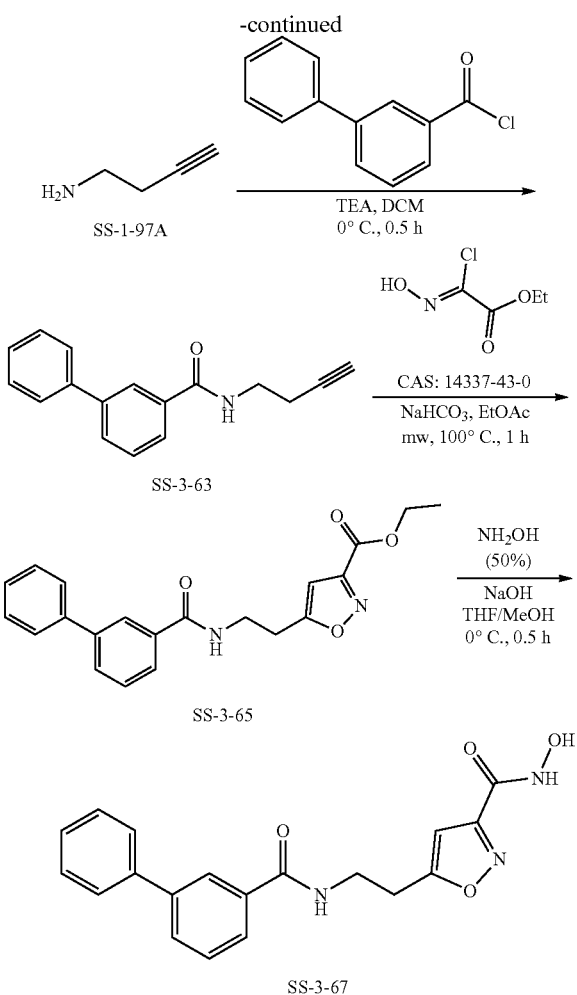

Synthesis of 2-(but-3-yn-1-yl)isoindoline-1,3-dione (SS-1-95): To a stirred solution of 3-butyn-1-ol (140 mg, 2.0 mmol), phthalimide (382 mg, 2.6 mmol), and PPh$_3$ (682 mg, 2.6 mmol) was added DEAD (525 mg, 2.6 mmol) at 0° C. under Ar protection. The resulting mixture was slowly warmed up to room temperature and stirred at the same temperature for 2.5 h. Then the reaction was quenched with H$_2$O, and extracted with EtOAc (3×20 mL). The combined organic extracts were washed with brine (40 mL), dried over sodium sulfate, and concentrated under vacuum. The crude product was purified by flash chromatography (0-50% EtOAc/hexane), and the title compound was obtained as white powder (370 mg, 93%). $^1$H NMR (400 MHz, CDCl$_3$) δ 7.86 (dd, J=5.5, 3.0 Hz, 2H), 7.73 (dd, J=5.5, 3.0 Hz, 2H), 3.89 (t, J=7.1 Hz, 2H), 2.62 (td, J=7.1, 2.7 Hz, 2H), 1.96 (t, J=2.7 Hz, 1H). $^{13}$C NMR (100 MHz, CDCl$_3$) δ 168.0, 134.1, 132.0, 123.4, 80.3, 70.3, 36.6, 18.4.

Synthesis of N-(but-3-yn-1-yl)-[1,1'-biphenyl]-3-carboxamide (SS-3-63): To a stirred solution of SS-1-95 (215 mg, 1.08 mmol) in MeOH (5 mL) was added N2H4 (0.1 mL, 2.7 mmol). The resulting mixture was stirred at room temperature for 16 h. Then participate was filtered off, and the filtrate was quenched with water (5 mL), acidified to pH 2 with 2 N HCl. The solution was concentrated under vacuum to afford SS-1-97A as white powder. The crude product was used directly into next step. The a stirred solution of SS-1-97A in DCM (5 mL) was added TEA (0.25 mL, 1.6 mmol) and [1,1'-biphenyl]-3-carbonyl chloride (280 mg, 1.3 mmol) at 0° C. Then the resulting mixture was stirred at same temperature for 30 min. The reaction was quenched with water (5 mL), extracted with DCM (3×10 mL) The combined organic extracts were washed with brine (40 mL), dried over sodium sulfate, and concentrated under vacuum. The crude product was purified by flash chromatography (0-30% EtOAc/Hexane), and the title compound was obtained as white powder (140 mg, 52%, crude).

Synthesis of ethyl 5-(2-([1,1'-biphenyl]-3-ylcarboxamido)ethyl)isoxazole-3-carboxylate (SS-3-65): To a solution of SS-3-63 (170 mg, 0.56 mmol) in EtOAc (2 mL) were added NaHCO$_3$ (144 mg, 1.69 mmol) and ethyl 2-chloro-2-(hydroxyimino)acetate (255 mg, 1.69 mmol) in a microwave reaction tube. The mixture was heated at 100° C. for 1 h in a microwave reactor. After completion of the reaction, precipitate solid was filtered off and the filtrate was concentrated under reduced pressure. The crude product was purified by flash chromatography (0-50% EtOAc/hexane), and the title compound was obtained as colorless oil (100 mg, 49%). $^1$H NMR (400 MHz, CDCl$_3$) δ 7.98 (s, 1H), 7.76-7.65 (m, 2H), 7.58-7.51 (m, 2H), 7.45-7.38 (m, 3H), 7.36-7.30 (m, 1H), 7.06 (t, J=5.4 Hz, 1H), 6.47 (s, 1H), 4.35 (q, J=7.1 Hz, 2H), 3.78 (q, J=6.5 Hz, 2H), 3.14 (t, J=6.6 Hz, 2H), 1.33 (t, J=7.1 Hz, 3H). $^{13}$C NMR (100 MHz, CDCl$_3$) δ 172.8, 168.0, 160.0, 156.6, 141.7, 140.1, 134.7, 130.3, 129.1, 128.9 (2C), 127.8, 127.2 (2C), 125.9, 125.8, 102.7, 62.2, 38.0, 27.1, 14.1.

Synthesis of 5-(2-([1,1'-biphenyl]-3-ylcarboxamido)ethyl)-N-hydroxyisoxazole-3-carboxamide (SS-3-67): In a round bottom flask, NaOH (90 mg, 2.2 mmol) was dissolved in 50% aqueous NH$_2$OH (0.9 mL, approx. 50 equiv) at 0° C. A solution of SS-3-65 (100 mg, 0.27 mmol) in 1:1 THF/MeOH (4 mL) was added dropwise, and stirring was continued for 30 min while warming to room temperature. The solution was neutralized with 6N HCl and extracted with EtOAc (3×10 mL). The organic layers were separated, washed with brine, dried over Na2SO$_4$, concentrated under vacuum. The crude product was purified by flash chromatography (0-10% MeOH/DCM) and prep-HPLC (Method 2) and lyophilized to afford the desired product as off-white powder (30 mg, 32%). $^1$H NMR (400 MHz, DMSO-d$_6$) δ 11.47 (br s, 1H), 9.33 (br s, 1H), 8.81 (t, J=5.6 Hz, 1H), 8.08 (s, 1H), 7.82 (t, J=7.4 Hz, 2H), 7.72 (d, J=7.4 Hz, 2H), 7.56 (t, J=7.7 Hz, 1H), 7.50 (t, J=7.6 Hz, 2H), 7.41 (t, J=7.1 Hz, 1H), 6.64 (s, 1H), 3.63 (q, J=6.5 Hz, 2H), 3.12 (t, J=6.8 Hz, 3H). ESI HRMS calc. for C$_{19}$H$_{16}$N$_3$O$_4$: m/z 350.1146; found: 350.1132.

Example 5

Synthesis of 5-(3-(3,4-dichlorophenoxy)propyl)-N-hydroxyisoxazole-3-carboxamide

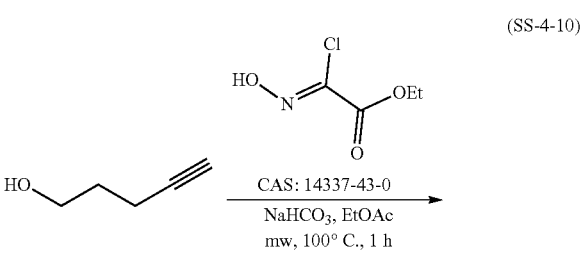

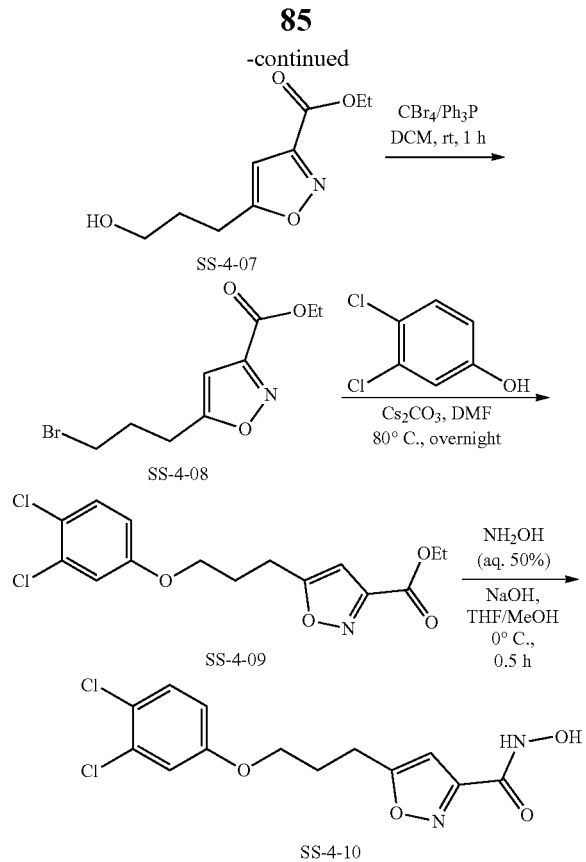

Synthesis of ethyl 5-(3-hydroxypropyl)isoxazole-3-carboxylate (SS-4-07): To a solution of 5-hexyn-1-ol (300 mg, 3.57 mmol) in EtOAc (5 mL) were added NaHCO$_3$ (900 mg, 10.7 mmol) and ethyl 2-chloro-2-(hydroxyimino)acetate (1.6 g, 10.7 mmol) in a microwave reaction tube. The mixture was heated at 100° C. for 1 h in a microwave reactor. After completion of the reaction, precipitate solid was filtered off and the filtrate was concentrated under reduced pressure. The crude product was purified by flash chromatography (0-80% EtOAc/hexane), and the title compound was obtained as colorless oil (680 mg, 96%). $^1$H NMR (400 MHz, CDCl$_3$) δ 6.42 (s, 1H), 4.40 (q, J=7.1 Hz, 2H), 3.70 (t, J=6.1 Hz, 2H), 2.92 (t, J=7.6 Hz, 2H), 1.97-1.88 (m, 2H), 1.38 (t, J=7.1 Hz, 3H). $^{13}$C NMR (100 MHz, CDCl$_3$) δ 175.2, 160.3, 156.5, 101.8, 62.2, 61.3, 30.2, 23.3, 14.2.

Synthesis of ethyl ethyl 5-(3-bromopropyl)isoxazole-3-carboxylate (SS-4-08): To a stirred solution of SS-4-07 (680 mg, 3.42 mmol) in DCM (30 mL) were added CBr$_4$ (1.70 g, 5.13 mmol) and Ph$_3$P (1.35 g, 5.13 mmol) at 0° C. Then the resulting mixture was stirred at room temperature for 1 h. The reaction was quenched with water (5 mL), extracted with DCM (3×10 mL). The combined organic extracts were washed with brine (30 mL), dried over sodium sulfate, and concentrated under vacuum. The crude product was purified by flash chromatography (0-40% EtOAc/hexane), and the title compound was obtained as colorless oil (850 mg, 83%). $^1$H NMR (400 MHz, CDCl$_3$) δ 6.46 (s, 1H), 4.42 (q, J=7.1 Hz, 2H), 3.43 (t, J=6.3 Hz, 2H), 3.01 (t, J=7.3 Hz, 2H), 2.33-2.18 (m, 2H), 1.40 (t, J=7.1 Hz, 3H). $^{13}$C NMR (100 MHz, CDCl$_3$) δ 173.6, 160.1, 156.6, 102.3, 62.3, 31.9, 30.2, 25.3, 14.3.

Synthesis of ethyl 5-(3-((3,4-dichlorophenyl)amino)propyl)isoxazole-3-carboxylate (SS-4-09): To a stirred solution of SS-4-08 (464 mg, 2.85 mmol) in DMF (15 mL) were added 3,4-dichlorophenol (850 mg, 3.41 mmol) and Cs$_2$CO$_3$ (1.87 g, 5.70 mmol) at room temperature. The resulting mixture was heated at 80° C. 2 h. The reaction was quenched with sat. aqueous NH$_4$Cl (5 mL), extracted with EtOAc (3×10 mL). The combined organic extracts were washed with brine (30 mL), dried over sodium sulfate, and concentrated under vacuum. The crude product was purified by flash chromatography (0-30% EtOAc/hexane), and the title compound was obtained as colorless oil (490 mg, 80%). $^1$H NMR (400 MHz, CDCl$_3$) δ 7.28 (d, J=8.9 Hz, 1H), 6.94 (d, J=2.8 Hz, 1H), 6.71 (dd, J=8.9, 2.9 Hz, 1H), 6.43 (s, 1H), 4.41 (q, J=7.1 Hz, 2H), 3.96 (t, J=5.9 Hz, 2H), 3.00 (t, J=7.5 Hz, 2H), 2.26-2.08 (m, 2H), 1.38 (t, J=7.1 Hz, 3H). $^{13}$C NMR (100 MHz, CDCl$_3$) δ 174.3, 160.1, 157.7, 156.5, 132.9, 130.8, 124.2, 116.4, 114.5, 102.0, 66.9, 62.2, 27.0, 23.4, 14.2.

Synthesis of 5-(3-((3,4-dichlorophenyl)amino)propyl)-N-hydroxyisoxazole-3-carboxamide (SS-4-10): In a round bottom flask, NaOH (150 mg, 3.72 mmol) was dissolved in 50% aqueous NH$_2$OH (1.5 mL, approx. 50 equiv) at 0° C. A solution of SS-4-09 (160 mg, 0.47 mmol) in 1:1 THF/MeOH (6 mL) was added dropwise, and stirring was continued for 30 min while warming to room temperature. The solution was neutralized with 2N HCl and extracted with EtOAc (3×10 mL). The organic layers were separated, washed with brine, dried over Na$_2$SO$_4$, concentrated under vacuum. The crude product was purified by HPLC (Method 2) and lyophilized to afford the desired product as white powder (65 mg, 40%). $^1$H NMR (400 MHz, DMSO-d$_6$) δ 11.45 (s, 1H), 9.33 (s, 1H), 7.51 (d, J=8.9 Hz, 1H), 7.23 (d, J=2.9 Hz, 1H), 6.96 (dd, J=8.9, 2.9 Hz, 1H), 6.60 (s, 1H), 4.06 (t, J=6.1 Hz, 2H), 2.96 (t, J=7.5 Hz, 2H), 2.15-2.03 (m, 2H). $^{13}$C NMR (100 MHz, DMSO-d$_6$) δ 173.8, 157.9, 157.5, 156.3, 131.6, 131.0, 122.4, 116.4, 115.5, 100.7, 67.2, 40.2, 39.9, 39.7, 39.5, 39.3, 39.1, 38.9, 26.4, 22.6. ESI HRMS calc. for C$_{13}$H$_{13}$C$_{12}$N$_2$O$_4$: [M+H]$^+$, m/z 331.0247; found: 331.0264.

Example 6

Synthesis of 5-(4-(5,6-dichloro-1H-indol-1-yl)butyl)-N-hydroxyisoxazole-3-carboxamide

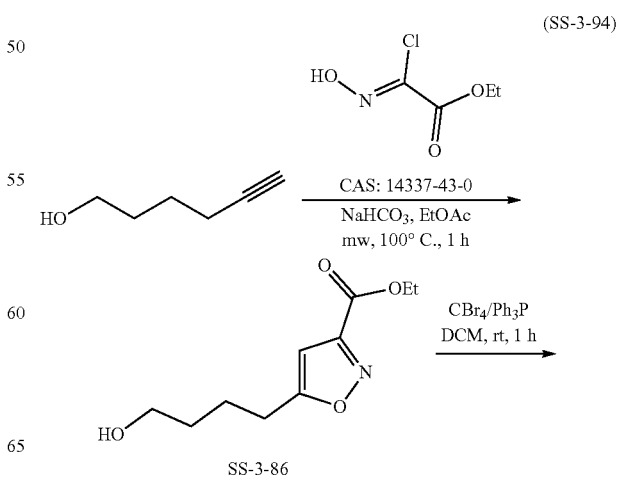

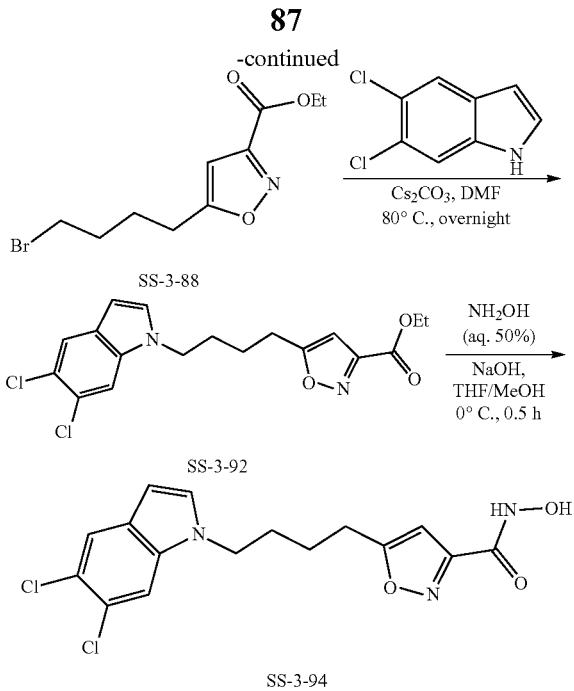

Synthesis of ethyl 5-(4-hydroxybutyl)isoxazole-3-carboxylate (SS-3-86): To a solution of 5-hexyn-1-ol (200 mg, 2.0 mmol) in EtOAc (3 mL) were added NaHCO$_3$ (504 mg, 6.0 mmol) and ethyl 2-chloro-2-(hydroxyimino)acetate (906 mg, 6.0 mmol) in a microwave reaction tube. The mixture was heated at 100° C. for 1 h in a microwave reactor. After completion of the reaction, precipitate solid was filtered off and the filtrate was concentrated under reduced pressure. The crude product was purified by flash chromatography (0-80% EtOAc/hexane), and the title compound was obtained as colorless oil (370 mg, 87%). $^1$H NMR (400 MHz, CDCl$_3$) δ 6.41 (s, 1H), 4.42 (qd, J=7.1, 1.3 Hz, 2H), 3.68 (td, J=6.3, 1.3 Hz, 2H), 2.84 (t, J=7.5 Hz, 2H), 1.90-1.76 (m, 2H), 1.67-1.60 (m, 2H), 1.40 (td, J=7.1, 1.3 Hz, 3H). $^{13}$C NMR (100 MHz, CDCl$_3$) δ 175.4, 160.3, 156.5, 101.7, 62.3, 62.2, 31.9, 26.6, 23.9, 14.3.

Synthesis of ethyl 5-(4-bromobutyl)isoxazole-3-carboxylate (SS-3-88): To a stirred solution of SS-3-86 (100 mg, 0.47 mmol) in DCM (5 mL) were added CBr$_4$ (232 mg, 0.47 mmol) and Ph$_3$P (184 mg, 0.47 mmol) at 0° C. Then the resulting mixture was stirred at room temperature for 1 h. The reaction was quenched with water (5 mL), extracted with DCM (3×10 mL). The combined organic extracts were washed with brine (30 mL), dried over sodium sulfate, and concentrated under vacuum. The crude product was purified by flash chromatography (0-40% EtOAc/hexane), and the title compound was obtained as colorless oil (90 mg, 89%). $^1$H NMR (400 MHz, CDCl$_3$) δ 6.41 (s, 1H), 4.40 (q, J=7.1 Hz, 2H), 3.40 (t, J=6.2 Hz, 2H), 2.83 (t, J=6.9 Hz, 2H), 1.89-1.87 (m, 4H), 1.38 (t, J=7.1 Hz, 3H). $^{13}$C NMR (100 MHz, CDCl$_3$) δ 174.7, 160.2, 156.5, 101.8, 62.1, 32.8, 31.8, 26.0, 25.9, 14.2.

Synthesis of ethyl 5-(4-(5,6-dichloro-1H-indol-1-yl)butyl)isoxazole-3-carboxylate (SS-3-92): To a stirred solution of SS-3-88 (90 mg, 0.33 mmol) in DMF (3 mL) were added 5,6-dichloro-1H-indole (56 mg, 0.30 mmol) and Cs$_2$CO$_3$ (217 mg, 0.66 mmol) at room temperature. The resulting mixture was heated at 80° C. overnight. The reaction was quenched with sat. aqueous NH$_4$Cl (5 mL), extracted with EtOAc (3×10 mL). The combined organic extracts were washed with brine (30 mL), dried over sodium sulfate, and concentrated under vacuum. The crude product was purified by flash chromatography (0-30% EtOAc/hexane), and the title compound was obtained as colorless oil (90 mg, 80%). $^1$H NMR (400 MHz, CDCl$_3$) δ 7.68 (s, 1H), 7.39 (s, 1H), 7.08 (d, J=3.2 Hz, 1H), 6.42 (dd, J=3.1, 0.7 Hz, 1H), 6.35 (s, 1H), 4.42 (q, J=7.1 Hz, 2H), 4.09 (t, J=6.9 Hz, 2H), 2.80 (t, J=7.4 Hz, 2H), 1.92-1.85 (m, 2H), 1.77-1.65 (m, 2H), 1.41 (t, J=7.1 Hz, 3H). $^{13}$C NMR (100 MHz, CDCl$_3$) δ 174.5, 160.2, 156.6, 134.9, 129.7, 128.3, 125.7, 123.6, 122.1, 110.9, 101.9, 101.3, 62.3, 46.3, 29.5, 26.4, 25.0, 14.3.

Synthesis of 5-(4-(5,6-dichloro-1H-indol-1-yl)butyl)-N-hydroxyisoxazole-3-carboxamide (SS-3-94): In a round bottom flask, NaOH (76 mg, 1.9 mmol) was dissolved in 50% aqueous NH$_2$OH (0.9 mL, approx. 50 equiv) at 0° C. A solution of SS-3-92 (90 mg, 0.24 mmol) in 1:1 THF/MeOH (4 mL) was added dropwise, and stirring was continued for 30 min while warming to room temperature. The solution was neutralized with 2N HCl and extracted with EtOAc (3×10 mL). The organic layers were separated, washed with brine, dried over Na$_2$SO$_4$, concentrated under vacuum. The crude product was purified by HPLC (Method 2) and lyophilized to afford the desired product as off-white powder (35 mg, 39%). $^1$H NMR (400 MHz, DMSO-d$_6$) δ 11.43 (s, 1H), 9.32 (d, J=1.6 Hz, 1H), 7.89 (s, 1H), 7.79 (s, 1H), 7.51 (d, J=3.1 Hz, 1H), 6.51 (s, 1H), 6.46 (d, J=3.1 Hz, 1H), 4.22 (t, J=7.0 Hz, 2H), 2.82 (t, J=7.5 Hz, 2H), 1.65-1.75 (m, 2H), 1.65-1.54 (m, 2H). $^{13}$C NMR (100 MHz, DMSO-d$_6$) δ 174.3, 157.4, 156.3, 134.7, 131.3, 127.9, 123.5, 121.5, 121.4, 111.7, 100.6, 100.5, 45.2, 29.14, 25.27, 24.12. ESI HRMS calc. for C$_{16}$H$_{16}$N$_3$O$_3$C$_{12}$: [M+H]$^+$, m/z 368.0563; found: 368.0545.

Example 7

Synthesis of 5-(4-(6-chloro-3,4-dihydroquinolin-1(2H)-yl)butyl)-N-hydroxyisoxazole-3-carboxamide

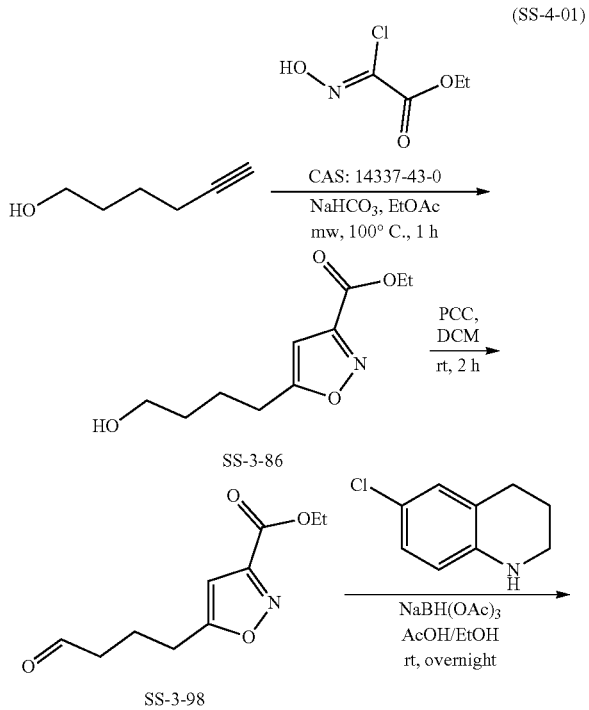

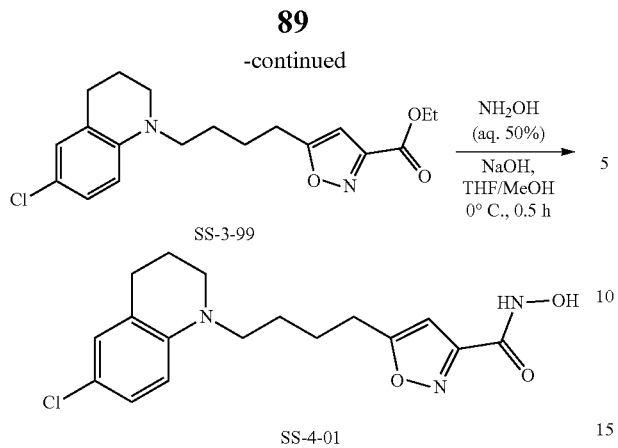

Synthesis of ethyl 5-(4-hydroxybutyl)isoxazole-3-carboxylate (SS-3-86): To a solution of 5-hexyn-1-ol (200 mg, 2.0 mmol) in EtOAc (3 mL) were added NaHCO$_3$ (504 mg, 6.0 mmol) and ethyl 2-chloro-2-(hydroxyimino)acetate (906 mg, 6.0 mmol) in a microwave reaction tube. The mixture was heated at 100° C. for 1 h in a microwave reactor. After completion of the reaction, precipitate solid was filtered off and the filtrate was concentrated under vacuum. The crude product was purified by flash chromatography (0-80% EtOAc/hexane), and the title compound was obtained as colorless oil (370 mg, 87%). $^1$H NMR (400 MHz, CDCl$_3$) δ 6.41 (s, 1H), 4.42 (qd, J=7.1, 1.3 Hz, 2H), 3.68 (td, J=6.3, 1.3 Hz, 2H), 2.84 (t, J=7.5 Hz, 2H), 1.90-1.76 (m, 2H), 1.67-1.60 (m, 2H), 1.40 (td, J=7.1, 1.3 Hz, 3H). $^{13}$C NMR (100 MHz, CDCl$_3$) δ 175.4, 160.3, 156.5, 101.7, 62.3, 62.2, 31.9, 26.6, 23.9, 14.3.

Synthesis of ethyl 5-(4-oxobutyl)isoxazole-3-carboxylate (SS-3-98): To a stirred solution of SS-3-86 (150 mg, 0.70 mmol) in DCM (5 mL) was added pyridinium chlorochromate (300 mg, 1.4 mmol) at room temperature. The resulting mixture was stirred at same temperature for 2 h. Then the excess solid was filtered off, and the filtrate was concentrated under vacuum. The crude product was purified by flash chromatography (0-60% EtOAc/hexane), and the title compound was obtained as colorless oil (130 mg, 88%). $^1$H NMR (400 MHz, CDCl$_3$) δ 9.75 (t, J=1.1 Hz, 1H), 6.40 (s, 1H), 4.38 (q, J=7.1 Hz, 2H), 2.83 (t, J=7.3 Hz, 2H), 2.53 (td, J=7.1, 1.0 Hz, 2H), 2.11-1.94 (m, 2H), 1.36 (t, J=7.1 Hz, 3H). $^{13}$C NMR (101 MHz, CDCl$_3$) δ 200.91, 174.33, 160.07, 156.47, 101.93, 77.48, 77.16, 76.84, 62.13, 42.60, 25.84, 19.83, 14.15. $^{13}$C NMR (100 MHz, CDCl$_3$) δ 200.9, 174.3, 160.1, 156.5, 101.9, 62.1, 42.6, 25.8, 19.8, 14.1.

Synthesis of ethyl 5-(4-(6-chloro-3,4-dihydroquinolin-1(2H)-yl)butyl)isoxazole-3-carboxylate (SS-3-99): To a stirred solution of SS-3-98 (130 mg, 0.62 mmol) and 6-chloro-1,2,3,4-tetrahydroquinoline (104 mg, 0.62 mmol) in EtOH/AcOH (5 mL/0.5 mL) was added NaBH(OAc)$_3$ (262.8 mg, 1.24 mmol) at room temperature. Then resulting mixture was stirred at same temperature overnight. Then the reaction was quenched with sat aqueous NaHCO$_3$ solution (5 mL), and extracted with DCM (3×10 mL). The organic layers were separated, washed with brine, dried over Na$_2$SO$_4$, concentrated under vacuum. The crude product was purified by flash chromatography (0-20% EtOAc/hexane), and the title compound was obtained as colorless oil (130 mg, 58%). $^1$H NMR (400 MHz, CDCl$_3$) δ 6.95 (dd, J=8.7, 2.6 Hz, 1H), 6.88 (d, J=2.6 Hz, 1H), 6.42 (d, J=8.0 Hz, 1H), 6.41 (s, 1H), 4.43 (q, J=7.1 Hz, 2H), 3.29-3.12 (m, 4H), 2.84 (t, J=7.3 Hz, 2H), 2.69 (t, J=6.3 Hz, 2H), 1.94-1.88 (m, 2H), 1.80-1.72 (m, 2H), 1.67-1.60 (m, 2H), 1.41 (t, J=7.1 Hz, 3H). $^{13}$C NMR (100 MHz, CDCl$_3$) δ 175.1, 160.2, 156.5, 143.8, 128.8, 126.8, 124.1, 120.1, 111.5, 101.7, 62.2, 51.1, 49.5, 28.1, 26.7, 25.7, 25.2, 22.1, 14.2.

Synthesis of 5-(4-(6-chloro-3,4-dihydroquinolin-1(2H)-yl)butyl)-N-hydroxyisoxazole-3-carboxamide (SS-4-01): In a round bottom flask, NaOH (116 mg, 2.9 mmol) was dissolved in 50% aqueous NH$_2$OH (1.0 mL, approx. 50 equiv) at 0° C. A solution of SS-3-99 (130 mg, 0.36 mmol) in 1:1 THF/MeOH (6 mL) was added dropwise, and stirring was continued for 30 min while warming to room temperature. The solution was neutralized with 2N HCl and extracted with EtOAc (3×10 mL). The organic layers were separated, washed with brine, dried over Na$_2$SO$_4$, concentrated under vacuum. The crude product was purified by HPLC (Method 2) and lyophilized to afford the desired product as off-white powder (100 mg, 62%, TFA salt). $^1$H NMR (400 MHz, DMSO-d$_6$) δ 11.43 (s, 1H), 6.93 (dd, J=8.7, 2.6 Hz, 1H), 6.88 (d, J=2.7 Hz, 1H), 6.55 (s, 1H), 6.52 (s, 1H), 3.29-3.16 (m, 4H), 2.84 (t, J=7.4 Hz, 2H), 2.65 (t, J=6.3 Hz, 2H), 1.86-1.77 (m, 2H), 1.69-1.64 (m, 2H), 1.57-1.50 (m, 2H). $^{13}$C NMR (100 MHz, DMSO-d$_6$) δ 174.5, 157.4, 156.3, 143.8, 128.1, 126.3, 123.8, 118.1, 111.6, 100.5, 50.0, 48.5, 27.4, 25.7, 24.7, 24.4, 21.3. ESI HRMS calc. for $C_{17}H_{21}N_3O_3C_1$: [M+H]$^+$, m/z 350.1266; found: 350.1251.

Example 8

Synthesis of 5-(4-(6-chloro-4,4-dimethyl-3,4-dihydroquinolin-1(2H)-yl)butyl)-N-hydroxyisoxazole-3-carboxamide

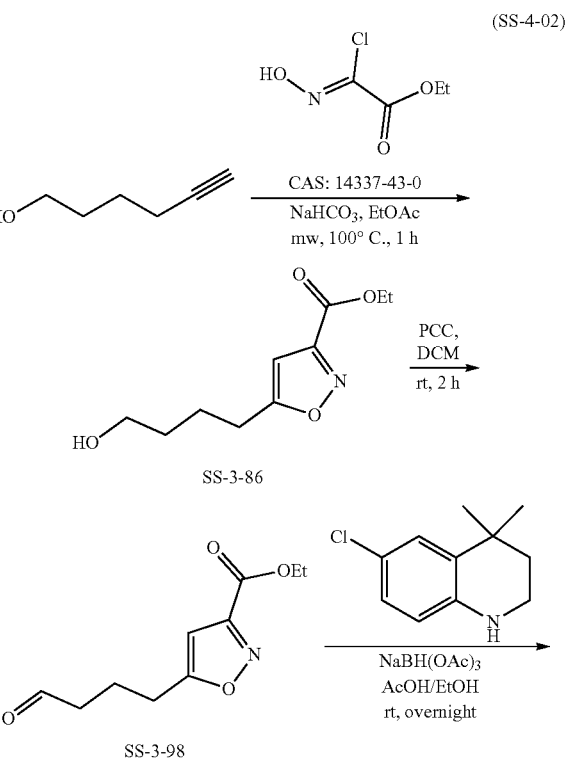

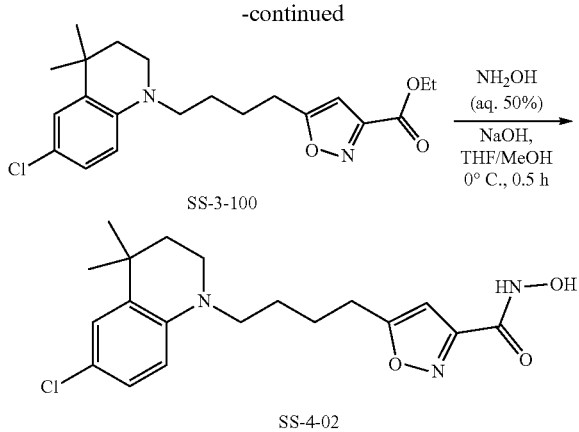

Synthesis of ethyl 5-(4-hydroxybutyl)isoxazole-3-carboxylate (SS-3-86): To a solution of 5-hexyn-1-ol (200 mg, 2.0 mmol) in EtOAc (3 mL) were added NaHCO$_3$ (504 mg, 6.0 mmol) and ethyl 2-chloro-2-(hydroxyimino)acetate (906 mg, 6.0 mmol) in a microwave reaction tube. The mixture was heated at 100° C. for 1 h in a microwave reactor. After completion of the reaction, precipitate solid was filtered off and the filtrate was concentrated under vacuum. The crude product was purified by flash chromatography (0-80% EtOAc/hexane), and the title compound was obtained as colorless oil (370 mg, 87%). $^1$H NMR (400 MHz, CDCl$_3$) δ 6.41 (s, 1H), 4.42 (qd, J=7.1, 1.3 Hz, 2H), 3.68 (td, J=6.3, 1.3 Hz, 2H), 2.84 (t, J=7.5 Hz, 2H), 1.90-1.76 (m, 2H), 1.67-1.60 (m, 2H), 1.40 (td, J=7.1, 1.3 Hz, 3H). $^{13}$C NMR (100 MHz, CDCl$_3$) δ 175.4, 160.3, 156.5, 101.7, 62.3, 62.2, 31.9, 26.6, 23.9, 14.3.

Synthesis of ethyl 5-(4-oxobutyl)isoxazole-3-carboxylate (SS-3-98): To a stirred solution of SS-3-86 (150 mg, 0.70 mmol) in DCM (5 mL) was added pyridinium chlorochromate (300 mg, 1.4 mmol) at room temperature. The resulting mixture was stirred at same temperature for 2 h. Then the excess solid was filtered off, and the filtrate was concentrated under vacuum. The crude product was purified by flash chromatography (0-60% EtOAc/hexane), and the title compound was obtained as colorless oil (130 mg, 88%). $^1$H NMR (400 MHz, CDCl$_3$) δ 9.75 (t, J=1.1 Hz, 1H), 6.40 (s, 1H), 4.38 (q, J=7.1 Hz, 2H), 2.83 (t, J=7.3 Hz, 2H), 2.53 (td, J=7.1, 1.0 Hz, 2H), 2.11-1.94 (m, 2H), 1.36 (t, J=7.1 Hz, 3H). $^{13}$C NMR (101 MHz, CDCl$_3$) δ 200.91, 174.33, 160.07, 156.47, 101.93, 77.48, 77.16, 76.84, 62.13, 42.60, 25.84, 19.83, 14.15. $^{13}$C NMR (100 MHz, CDCl$_3$) δ 200.9, 174.3, 160.1, 156.5, 101.9, 62.1, 42.6, 25.8, 19.8, 14.1.

Synthesis of ethyl 5-(4-(6-chloro-4,4-dimethyl-3,4-dihydroquinolin-1(2H)-yl)butyl)isoxazole-3-carboxylate (SS-3-100): To a stirred solution of SS-3-98 (130 mg, 0.62 mmol) and 6-chloro-4,4-dimethyl-1,2,3,4-tetrahydroquinoline (121 mg, 0.62 mmol) in EtOH/AcOH (5 mL/0.5 mL) was added NaBH(OAc)$_3$ (262.8 mg, 1.24 mmol) at room temperature. Then resulting mixture was stirred at same temperature overnight. Then the reaction was quenched with sat aqueous NaHCO$_3$ solution (5 mL), and extracted with DCM (3×10 mL). The organic layers were separated, washed with brine, dried over Na$_2$SO$_4$, concentrated under vacuum. The crude product was purified by flash chromatography (0-20% EtOAc/hexane), and the title compound was obtained as colorless oil (100 mg, 42%). $^1$H NMR (400 MHz, CDCl$_3$) δ 7.10 (d, J=2.6 Hz, 1H), 6.96 (dd, J=8.8, 2.6 Hz, 1H), 6.42 (d, J=9.5 Hz, 1H), 6.41 (s, 1H), 4.43 (q, J=7.1 Hz, 2H), 3.32-3.19 (m, 4H), 2.85 (t, J=7.4 Hz, 2H), 1.80-1.64 (m, 6H), 1.41 (t, J=7.1 Hz, 3H), 1.25 (s, 6H). $^{13}$C NMR (100 MHz, CDCl$_3$) δ 175.1, 160.3, 156.5, 142.5, 132.9, 126.6, 126.1, 120.3, 111.7, 101.8, 62.2, 51.3, 45.9, 36.8, 32.3, 30.6 (2C), 26.8, 25.6, 25.3, 14.3.

Synthesis of 5-(4-(6-chloro-4,4-dimethyl-3,4-dihydroquinolin-1(2H)-yl)butyl)-N-hydroxyisoxazole-3-carboxamide (SS-4-02): In a round bottom flask, NaOH (89 mg, 2.2 mmol) was dissolved in 50% aqueous NH$_2$OH (0.9 mL, approx. 50 equiv) at 0° C. A solution of SS-3-99 (100 mg, 0.28 mmol) in 1:1 THF/MeOH (4 mL) was added dropwise, and stirring was continued for 30 min while warming to room temperature. The solution was neutralized with 2N HCl and extracted with EtOAc (3×10 mL). The organic layers were separated, washed with brine, dried over Na$_2$SO$_4$, concentrated under vacuum. The crude product was purified by HPLC (Method 2) and lyophilized to afford the desired product as off-white powder (100 mg, 75%, TFA salt). $^1$H NMR (400 MHz, DMSO-d$_6$) δ 11.43 (s, 1H), 7.07 (d, J=2.7 Hz, 1H), 6.94 (dd, J=8.7, 2.6 Hz, 1H), 6.55 (s, 1H), 6.54 (s, 1H), 3.28-3.21 (m, 4H), 2.84 (t, J=7.3 Hz, 2H), 1.71-1.46 (m, 6H), 1.19 (s, 6H). $^{13}$C NMR (100 MHz, DMSO-d$_6$) δ 174.5, 163.0, 157.4, 142.5, 132.5, 126.2, 125.3, 118.4, 111.9, 100.5, 50.2, 44.7, 40.2, 39.9, 39.7, 39.5, 39.3, 39.1, 38.9, 36.0, 31.8, 30.2 (2C), 25.6, 24.6, 24.5. ESI HRMS calc. for C$_{19}$H$_{24}$N$_3$O$_3$Cl: [M+H]$^+$, m/z 378.1579; found: 378.1566.

Example 9

Synthesis of 5-(4-(2,8-dichloro-10,11-dihydro-5H-dibenzo[b,f]azepin-5-yl)butyl)-N-hydroxyisoxazole-3-carboxamide

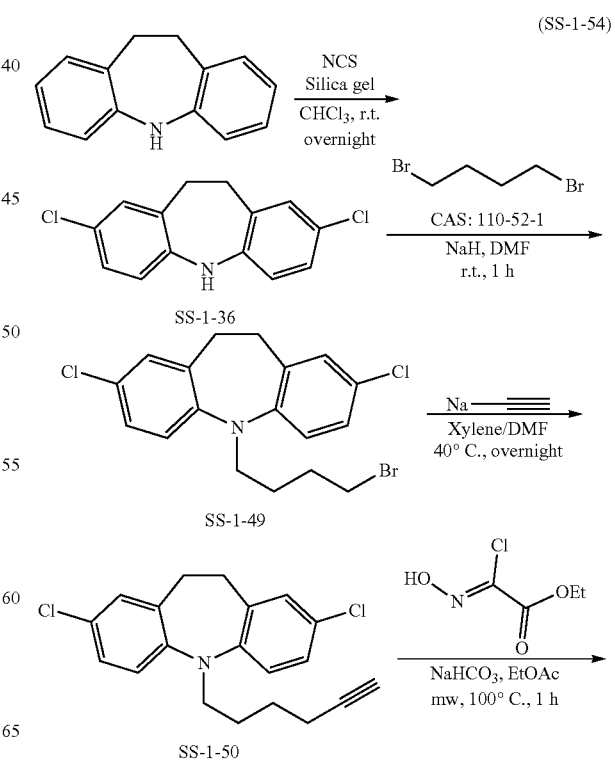

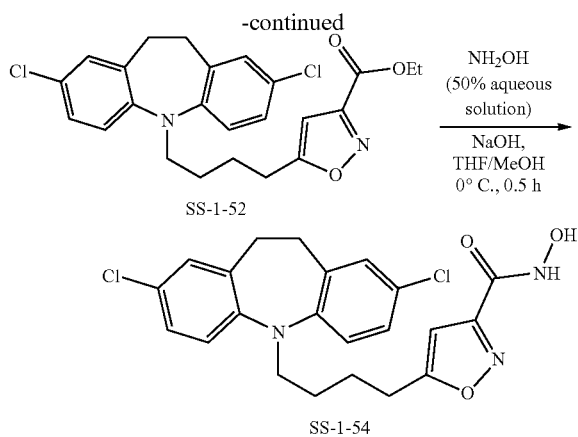

SS-1-52

SS-1-54

Synthesis of 5-(4-bromobutyl)-2,8-dichloro-10,11-dihydro-5H-dibenzo[b,f]azepine (SS-1-49): To a stirred solution of SS-1-36 (300 mg, 1.15 mmol) in DMF (5 mL) was added NaH (60%, 140 mg, 3.45 mmol) slowly. The mixture was stirred at room temperature for 15 min, followed with dropwise addition of 1,6-dibromobutane (364 mg, 1.7 mmol). The mixture was stirred at room temperature for 1 h. After completion of the reaction, 1 N HCl aqueous solution was added to neutralize pH to 6-7. Then the reaction solution was extracted with EtOAc and water for three times. The combined organic layers were separated, washed with water and brine, dried over $Na_2SO_4$, concentrated under reduced pressure. The crude product was purified by by column chromatography using EtOAc/hexane gradients (1-3%) to deliver the desired product SS-1-49 as colorless oil. The product was used directly into next step.

Synthesis of 2,8-dichloro-5-(hex-5-yn-1-yl)-10,11-dihydro-5H-dibenzo[b,f]azepine (SS-1-50): To a stirred solution of SS-1-49 (200 mg, 0.5 mmol) in xylene/DMF (2/2 mL) was added sodium acetylide syspension (0.2 mL, 18 wt. % slurry in xylene) under Ar protection at room temperature. Then the mixture was stirred at 40° C. overnight. After completion of the reaction, the reaction solution was extracted with EtOAc and water for three times. The combined organic layers were separated, washed with water and brine, dried over $Na_2SO_4$, concentrated under reduced pressure. The crude product was purified by column chromatography using EtOAc/hexane gradients (1-3%) to deliver the desired product SS-1-50 as colorless oil. $^1$H NMR (400 MHz, CDCl$_3$) δ 7.09-7.07 (m, 4H), 6.97 (d, J=9.0 Hz, 2H), 3.67 (t, J=6.8 Hz, 2H), 3.10 (s, 4H), 2.14 (td, J=7.0, 2.6 Hz, 2H), 1.89 (t, J=2.6 Hz, 1H), 1.67-1.64 (m, 2H), 1.55-1.51 (m, 2H).

Synthesis of ethyl 5-(4-(2,8-dichloro-10,11-dihydro-5H-dibenzo[b,f]azepin-5-yl)butyl)isoxazole-3-carboxylate (SS-1-52): To a solution of SS-1-50 (100 mg, 0.30 mmol) in EtOAc (3 mL) were added NaHCO$_3$ (75 mg, 0.90 mmol) and Ethyl 2-chloro-2-(hydroxyimino)acetate (135 mg, 0.90 mmol) in a microwave reaction tube. The mixture was heated at 100° C. for 1 h in a microwave reactor. After completion of the reaction, precipitate solid was filtered and the filtrate was concentrated under reduced pressure. The crude product was purified by column chromatography using EtOAc/hexane gradients (1-20%) to deliver the desired product SS-1-52 as light yellow oil. $^1$H NMR (400 MHz, CDCl$_3$) δ 7.09-7.08 (m, 4H), 6.96-6.93 (m, 2H), 6.31 (s, 1H), 4.43 (q, J=7.1 Hz, 2H), 3.67 (t, J=6.6 Hz, 2H), 3.10 (s, 4H), 2.74 (t, J=7.4 Hz, 2H), 1.76-1.59 (m, 4H), 1.41 (t, J=7.1 Hz, 3H).

Synthesis of 5-(4-(2,8-dichloro-10,11-dihydro-5H-dibenzo[b,f]azepin-5-yl)butyl)-N-hydroxyisoxazole-3-carboxamide (SS-1-54): Solid NaOH (80 mg, 2.0 mmol) was dissolved in a 50% aq. solution of NH$_2$OH (0.5 mL) at 0° C. Then, a solution of SS-1-52 (100 mg, 0.20 mmol) in 1:1 THF/MeOH (2/2 mL) was added dropwise to the aforementioned, vigorously stirred hydroxylamine solution for 30 min at the 0° C. After completion of the reaction, 1 N HCl aqueous solution was added to neutralize PH to 6-7. Then the mixture solution was extracted with EtOAc and water for three times. The combined organic layers were separated, washed with water and brine, dried over $Na_2SO_4$, concentrated under reduced pressure. The crude product was purified by prep-HPLC using MeOH (0.05% TFA)/H$_2$O (0.05% TFA) gradients (5-100%, Method 2) to deliver the desired product SS-1-54 as white powder. $^1$H NMR (400 MHz, CDCl$_3$) δ 7.09-7.07 (m, 4H), 6.95-6.92 (m, 2H), 6.37 (s, 1H), 3.66 (t, J=6.5 Hz, 2H), 3.09 (s, 4H), 2.72 (t, J=7.4 Hz, 2H), 1.76-1.68 (m, 2H), 1.63-1.57 (m, 2H); ESI HRMS calc. for $C_{22}H_{22}C_{12}N_3O_3$: [M+H]$^+$, m/z 446.1033; found: 446.1020.

Example 10

HDAC Isoform Inhibition

The IC$_{50}$ values for the compounds of Examples 1-9 versus HDAC1 and HDAC6 were determined as follows:

The HDAC1, 2, 4, 5, 6, 7, 8, 9, 10, and 11 assays used isolated recombinant human protein; HDAC3/NcoR2 complex was used for the HDAC3 assay. Substrate for HDAC1, 2, 3, 6, 10, and 11 assays is a fluorogenic peptide from p53 residues 379-382 (RHKKAc); substrate for HDAC8 is fluorogenic diacyl peptide based on residues 379-382 of p53 (RHKAcKAc). Acetyl-Lys(trifluoroacetyl)-AMC substrate was used for HDAC4, 5, 7, and 9 assays. Compounds were dissolved in DMSO and tested in 10-dose IC50 mode with 3-fold serial dilution starting at 30 μM. Control Compound Trichostatin A (TSA) was tested in a 10-dose IC$_{50}$ with 3-fold serial dilution starting at 5 μM. IC$_{50}$ values were extracted by curve-fitting the dose/response slopes. Assays were performed in duplicate and IC$_{50}$ values are an average of data from both experiments.

Materials

Human HDAC1 (GenBank Accession No. NM_004964): Full length with C-terminal GST tag, MW=79.9 kDa, expressed by baculovirus expression system in 519 cells. Enzyme is in 50 mM Tris-HCl, pH 8.0, 138 mM NaCl, 20 mM glutathione, and 10% glycerol, and stable for >6 months at −80° C. Purity is >10% by SDS-PAGE. Specific Activity is 20 U/μg, where one U=1 pmol/min under assay condition of 25 mM Tris/C$_1$, pH 8.0, 137 mM NaCl, 2.7 mM KCl, 1 mM MgCl$_2$, 0.1 mg/ml BSA, 100 μM HDAC substrate, and 13.2 ng/μl HDACl, incubation for 30 min at 30° C.

Human HDAC6 (GenBank Accession No. BC069243): Full length with N-terminal GST tag, MW=159 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >90% by SDS-PAGE. Specific Activity is 50 U/μg, where one U=1 pmol/min under assay condition of 25 mM Tris/Cl, pH8.0, 137 mM NaCl, 2.7 mM KCl, 1 mM MgCl$_2$, and 0.1 mg/ml BSA, 30 μM HDAC substrate, and 5 ng/μl HDAC6, incubation for 60 min at 30° C.

Substrate for HDAC1 and HDAC6: Acetylated peptide substrate for HDAC, based on residues 379-382 of p53 (Arg-His-Lys-Lys(Ac)), a site of regulatory acetylation by the p300 and CBP acetyltransferases (lysines 381, 382)1-6, is the best for HDAC from among a panel of substrates patterned on p53, histone H3 and histone H4 acetylation sites.

References: W. Gu et al., *Cell* (1997) 90 595; K. Sakaguchi et al., *Genes Dev.*, (1998) 12 2831; L. Liu et al., *Mal. Cell. Biol.*, (1999) 19 1202; A. Ito et al., *EMBO* (2001) 20 1331; N. A. Barley et al., *Mal. Cell*, (2001) 8 1243; and A. Ito et al., *EMBO* (2002) 21, 6236.

Reaction Buffer: 50 mM Tris-HCl, pH 8.0, 137 mM NaCl, 2.7 mM KCl, 1 mM $MgCl_2$, 1 mg/ml BSA.

Assay Conditions

HDAC1: 75 nM HDAC1 and 50 µM HDAC substrate are in the reaction buffer and 1% DMSO final. Incubate for 2 hours at 30° C. HDAC6: 12.6 nM HDAC6 and 50 µM HDAC substrate are in the reaction buffer and 1% DMSO final. Incubate for 2 hours at 30° C.

$IC_{50}$ Calculations

All $IC_{50}$ values are automatically calculated using the GraphPad Prism version 5 and Equation of Sigmoidal dose-response (variable slope): Y=Bottom+(Top-Bottom)/(1+10^((Log EC50-X)*HillSlope)), where X is the logarithm of concentration, Y is the response, Y starts at Bottom and goes to Top with a sigmoid shape. In most cases, "Bottom" is set 0, and "Top" is set "less than 120%". This is identical to the four parameter logistic equation. $IC_{50}$ curves also are drawn using the GraphPad Prism. The results are shown in Table 1B.

TABLE 1B[a]

| Compound | Structure | $IC_{50}$ (nM) HDAC1 | $IC_{50}$ (nM) HDAC6 | Selectivity HDAC1/HDAC6 |
|---|---|---|---|---|
| SS-1-100 | 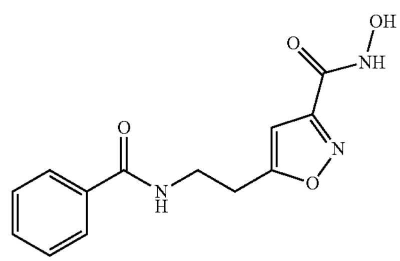 [SMILES: O=C(NCCc1cc(C(=O)NO)no1)c1ccccc1] | No inhibition | 194 | N/A |
| SS-2-08 | 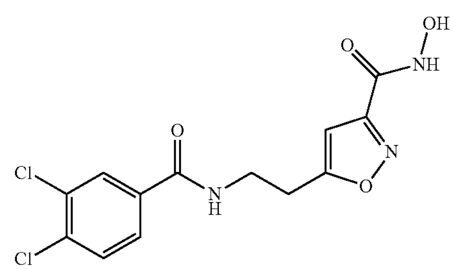 [SMILES: O=C(NCCc1cc(C(=O)NO)no1)c1ccc(Cl)c(Cl)c1] | 31500 | 75.2 | 419 |
| SS-3-66 | 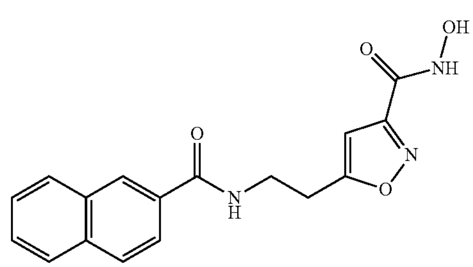 [SMILES: O=C(NCCc1cc(C(=O)NO)no1)c1ccc2ccccc2c1] | 3030 | 10.3 | 294 |
| SS-3-67 | 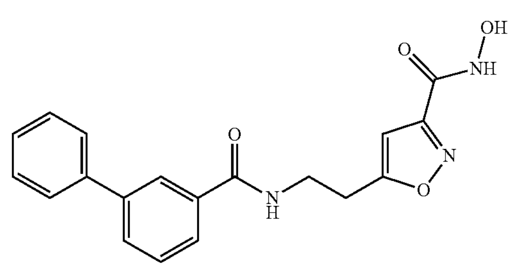 [SMILES: O=C(NCCc1cc(C(=O)NO)no1)c1cccc(-c2ccccc2)c1] | 2040 | 24.1 | 85 |

TABLE 1B[a]-continued

| Compound | Structure | IC$_{50}$ (nM) HDAC1 | IC$_{50}$ (nM) HDAC6 | Selectivity HDAC1/HDAC6 |
|---|---|---|---|---|
| SS-3-94 | 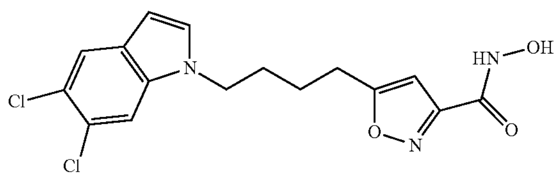 [SMILES: O=C(NO)c1cc(CCCCn2ccc3cc(Cl)c(Cl)cc32)on1] | 11205 | 693 | 16 |
| SS-4-01 | 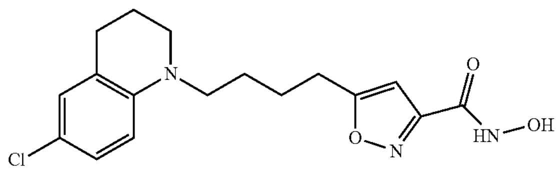 [SMILES: O=C(NO)c1cc(CCCCN2CCCc3cc(Cl)ccc32)on1] | 44000 | 1990 | 22 |
| SS-4-02 | 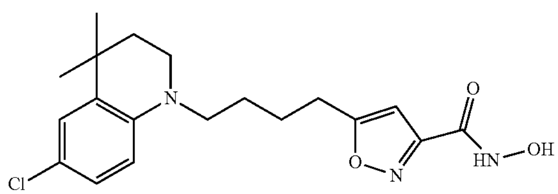 [SMILES: CC1(C)CCN(CCCCc2cc(C(=O)NO)no2)c2ccc(Cl)cc21] | 173500 | 4360 | 40 |
| SS-4-10 | 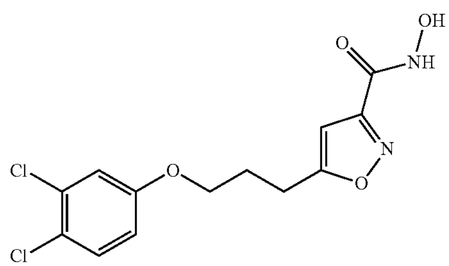 [SMILES: O=C(NO)c1cc(CCCOc2ccc(Cl)c(Cl)c2)on1] | N/A | 195 | |
| SS-1-54 | 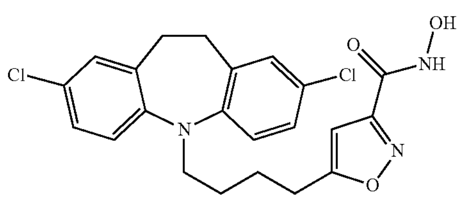 [SMILES: O=C(NO)c1cc(CCCCN2c3ccc(Cl)cc3CCc3cc(Cl)ccc32)on1] | No inhibition | 1345 | |
| Tubastatin A | 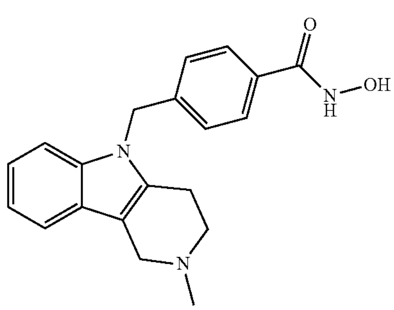 [SMILES: CN1CCc2c(c3ccccc3n2Cc2ccc(C(=O)NO)cc2)C1] | 12200 | 11 | 1109 |
| Trichostatin A | | 9.89 | 1.87 | 5 |

[a]Compounds were tested in duplicate 10-dose IC$_{50}$ mode with 3-fold serial dilution starting at 30 μM HDACs. HDAC reference compound Trichostatin A (TSA) was tested starting at 30 μM HDACs. HDAC reference compound Trichostatin A (TSA) was tested in a 10-dose IC$_{50}$ with 3-fold serial dilution starting at 10 μM. (Reaction Biology Corp, Malvern, PA).

Example 11

Screening of SS-2-08

The activity of SS-2-08 in several preclinical screening assays is provided in Table 2. SS-2-08 lacks Ames activity and shows good potency against HDAC6 and selectivity against HDAC1 and HDAC11. SS-2-08 was incubated with two strains of *Salmonella typhimurium* (TA98 and TA1537) in the presence and absence of mammalian microsomal enzymes (S9 mix) to investigate the possible mutagenicity of this compound. No significant number of revertant colonies was found for either strain, thus supporting the lack of mutagenicity of SS-2-08 under the conditions of the mini-Ames assay. SS-2-08 has an $IC_{50}$ of >30 µM against hERG.

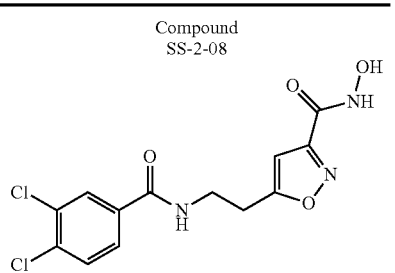

| | Compound SS-2-08 | |
|---|---|---|
| Structure | | SS-2-08<br>MW: 344.14<br>CLogP: 1.201<br>tPSA: 104.46 |
| HDAC isoform activities ($IC_{50}$, nM)[a] | HDAC6 | 75.2 |
| | HDAC1 | 31500 |
| | HDAC11 | 24600 |
| Liver microsomal stability ($t_{1/2}$ min, with NADPH)[b] | Mouse | 37 |
| | Human | 135 |
| Hepatocyte stability ($t_{1/2}$ min)[b] | Mouse | 22 |
| | Human | 108 |
| hERG test ($IC_{50}$, µM)[b] | HEK293 cells | >30 µM |
| Mini-Ames test[b] | TA97, TA1537 | Negative |

[a]Compounds were tested in duplicate in a 10-dose $IC_{50}$ mode with 3-fold serial dilution starting at 30 µM against 3 HDACs. HDAC reference compound Trichostain A (TSA) was tested in a 10-dose $IC_{50}$ with 3-fold serial dilution starting at 10 µM. (Reaction Biology Corp, Malvern, PA);
[b]The ADMET assays were conducted by Pharmaron, Inc., Irvine, CA.

Example 12

Cell Culture

Mouse neuroblastoma (N2a) cells were grown in a 1:1 mixture of DMEM (Dulbecco's Modified Eagle Medium) and F12 medium supplemented with glutamax (Invitrogen), 100 µg/mL streptomycin, 100 U/mL penicillin (Invitrogen), 10% fetal calf serum (Greiner Bio-one), 1% non-essential amino acids (Invitrogen), and 1.6% $NaHCO_3$ (Invitrogen) at 37° C. and 7.5% $CO_2$. To split the cells, cells were washed with Versene (Invitrogen) and dissociated with 0.05% Trypsine-EDTA (Invitrogen). DRG neurons were cultured from adult 12 month old Thy1.2-HSPB1 S135F mice. The DRG neurons were dissected from the spinal cord and kept in cold HBSS (without $MgCl_2$ and $CaCl_2$, Invitrogen). To extract the DRG neurons, the dissected tissue was incubated with Collagenase D (1 mg/mL) during 45' at 37° C., followed by incubation with 0.05% Trypsine-EDTA (Invitrogen) during 30' at 37° C. The cell suspension was washed in DRG PREP medium containing DMEM:F12 medium supplemented with 10% fetal calf serum (Greiner-Bio), 1% non-essential amino acids (Invitrogen), 0.14% sodium bicarbonate (Invitrogen), and 200 nM L-glutamine (Invitrogen). The DRG neurons were seeded on poly-L-ornithine-(Sigma-Aldrich) and laminine-(Sigma-Aldrich) coated coverslips and grown in a 1:1 mixture of DMEM (and F12 medium supplemented with 4 mM L-glutamax (Invitrogen), 10% foetal calf serum (GreinerBio), 50 µg/mL streptomycin, 50 U/mL penicillin (Invitrogen), 0.045% $NaHCO_3$ (Invitrogen), and 1.6 µg nerve growth factor (Millipore). The N2a cells and DRG neurons were treated overnight at 37° C. with dosages ranging from 10 nM up to 1 µM of the compounds or an equivalent dose of DMSO (Sigma-Aldrich).

Western Blot Analysis

Figure 18:
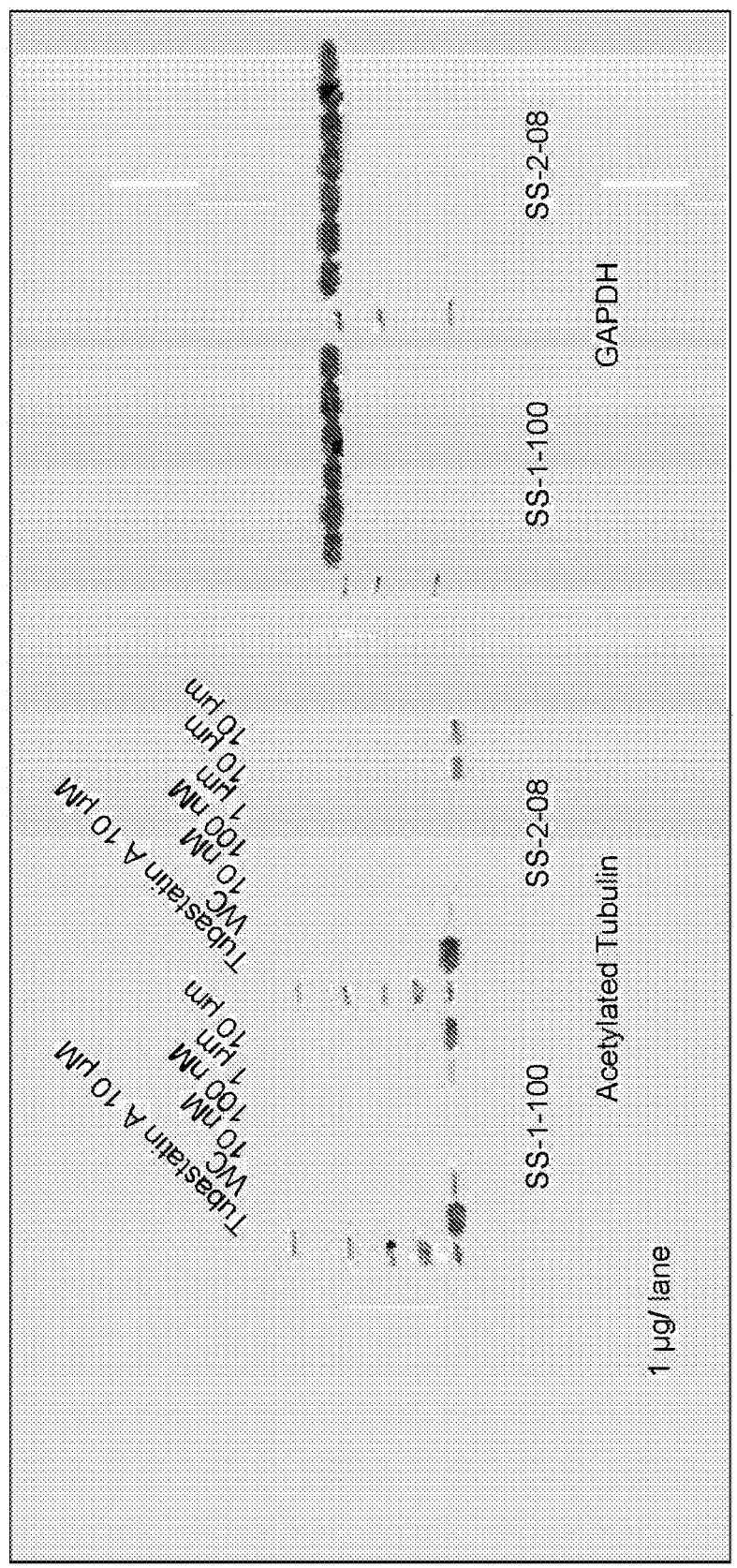
FIG. 18 is an illustration showing the results of a tubulin acetylation test in HEK293 cell lines; Left blots are acetyl-tubulin, Right blots (upside down) are GAPDH. The first lane of each blot is HEK-293 cells treated with Tubastatin A (10 μM) for 24 hours. The second lane of each blot is the same cells treated with vehicle. The next lanes are ascending concentrations of SS-1-100 and SS-2-08 from 10 nM to 10 μM. In the SS-2-08 blot, the 10 μM dose is done in duplicate.

The treated cells were washed with phosphate-buffered saline (PBS) and collected using the EpiQuik Total Histone Extraction Kit (EpiGentek) according to manufacturer's instructions. Tissues were dissected from the mice and snap-frozen in liquid nitrogen. Dissociation of the tissue was achieved by using tubes containing LysisMatrix D beads. Protein concentrations were determined using the microBCA kit (Thermo Fisher Scientific Inc., Pittsburgh, PA, USA) according to manufacturer's instructions. Before resolving the samples on a 12% sodium dodecyl sulfate-polyacrylamide gel electrophoresis (SDS-PAGE) gel, samples containing equal amounts of protein were supplemented with reducing sample buffer (Thermo Scientific) and heated at 95° C. for 5 min. After electrophoresis, the proteins were transferred to a polyvinylidene difluoride (PVDF) membrane (Millipore Corp., Bedford, MA, USA). The non-specific binding was blocked by incubation of the membrane in 5% bovine serum albumin (BSA), diluted in Tris Buffered Saline Tween (TBST, 50 mM TRIS, 150 mM NaCl, 0.1% Tween-20 (Applichem, Darmstadt, Germany) for 1 h at room temperature followed by incubation with primary antibodies overnight. The antibodies, diluted in TBS-T, were directed against α-tubulin (1/5000, T6199, Sigma-Aldrich), acetylated α-tubulin (1/5000, T6793 monoclonal, Sigma-Aldrich), histone H3 acetyl k9+k14 (1/1000, 9677L, Cell Signaling), and histone 4 (1/1000, ab10158, Abcam). The secondary antibodies, coupled to alkaline phosphatase (anti-mouse or anti-rabbit, 1/5000, Sigma-Aldrich), were used to detect the signal of the primary antibodies. Blots were visualised by adding the ECF substrate (Enhanced Chemical Fluorescence, GE Healthcare, Uppsala, Sweden) and imaged with the ImageQuant LAS 4000. A mild reblotting buffer (Millipore) was applied to strip the blots. ImageQuant TL version 7.0 software was used to quantify the blots. See FIG. 18.

Example 13

Cell Culture

Human Melanoma cells WM164 were cultured in RPMI 1640 media, supplemented with 10% FBS, penicillin/streptomycin (50 U/ml), L-glutamine (2 mM), and 2-mercaptoethanol (5004) (complete media), and grown under humidified conditions at 37° C. and 5% $CO_2$.

Immunoblots

The cells were lysed in a buffer containing 280 mM NaCl, 50 mM Tris HCL PH 8.0, 0.5% Igepal, 5 mM $MgCl_2$, 10% glycerol and 1× protease inhibitor (Roche), phosphatase inhibitor (Santa Cruz Biotechnology). Lysates were sonicated on ice for 8 minutes (2 cycles of 30 s on, 30 s rest) and then mixed with 6× gel loading buffer and boiled for 5 minutes. Samples were then resolved on 10% or 4-15% gradient gels and transferred to nitrocellulose membranes. Membranes were blocked with 5% milk-PBS-Tween. Bands were detected by scanning blots with an LI-COR Odyssey imaging system using both 700 and 800 channels. The antibodies used for immunobloting included Anti-acetyl-α-Tubulin (SC-23950) and anti-α-Tubulin (SC-32293), which were purchased from Santa Cruz Biotechnology. Anti-HDAC6 (C0226) was from Assay Biotech. Anti-GAPDH (68795) was from Sigma Aldrich. Anti STAT3 (12640), anti P-STAT3 Y-705 (9138), anti P-STAT3 S727 (9136), and anti Acetil-STAT3 (2523) were purchased from Cell signaling. Anti PD-L1 (PAS-28115) was obtained from Thermo Scientific. Anti-FLAG (F1804) antibody was from Sigma.

Figure 2:
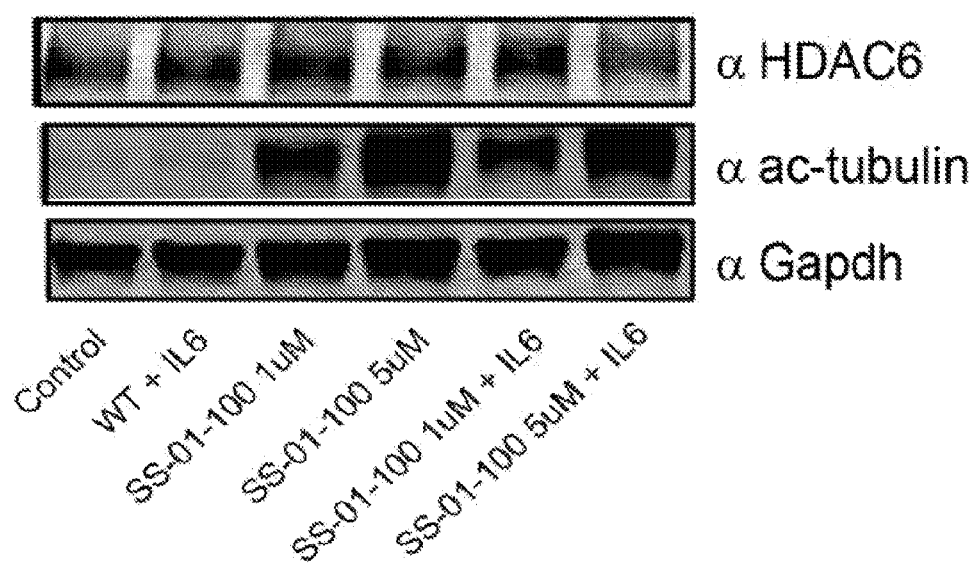
FIG. 2 is an immunoblot illustration showing the activity of SS-01-100 in WM164 human melanoma cell lines in the presence or absence of IL-6.
Figure 3:
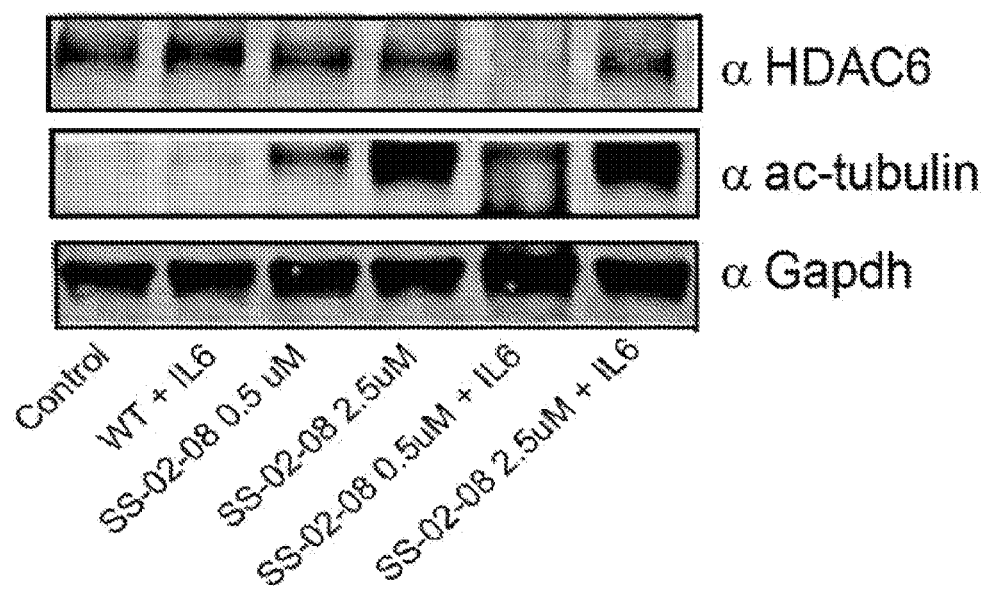
FIG. 3 is an immunoblot illustration showing the activity of SS-02-08 in WM164 human melanoma cell lines.
Figure 4:
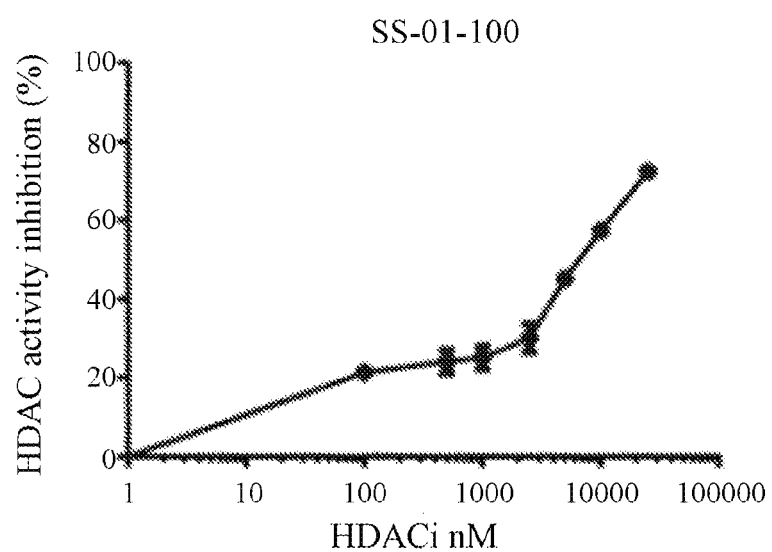
FIG. 4 is a line graph showing the HDAC activity of SS-1-100 in WM164 cancer cell lines.
Figure 5:
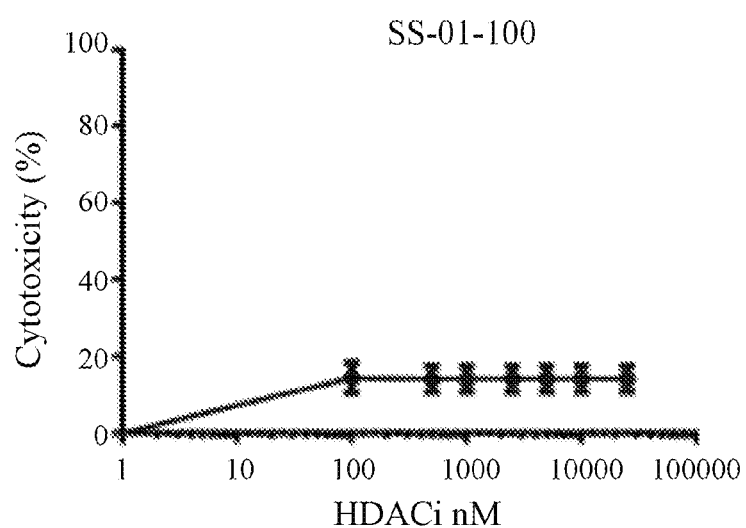
FIG. 5 is a line graph showing the cytotoxicity of SS-1-100 in WM164 cancer cell lines.
Figure 6:
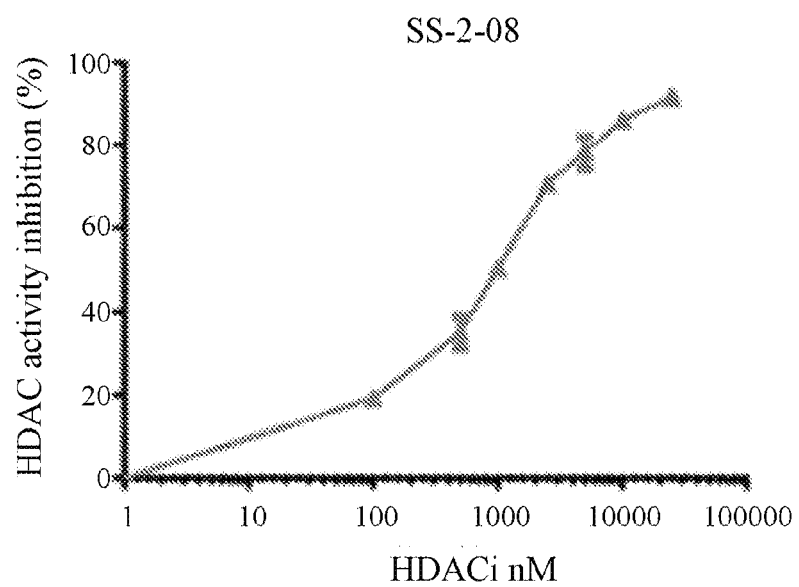
FIG. 6 is a line graph showing the HDAC activity of SS-2-08 in WM164 cancer cell lines.
Figure 7:
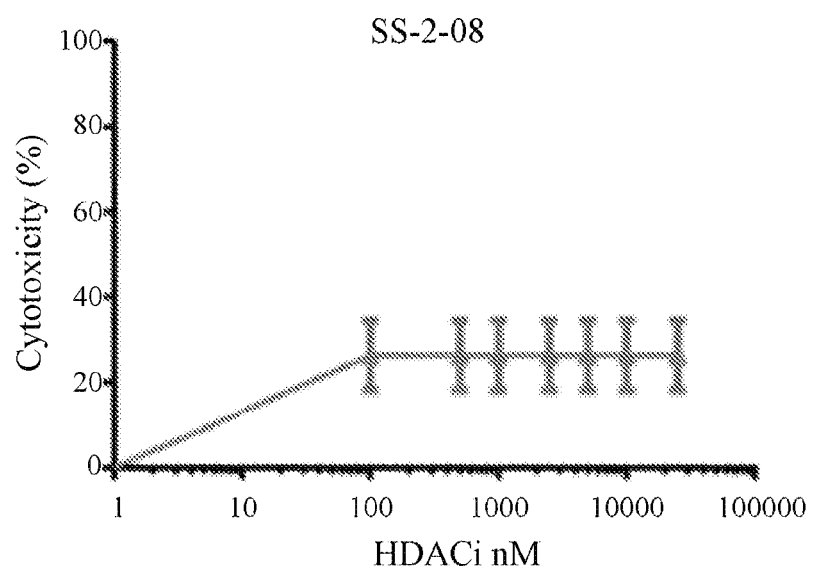
FIG. 7 is a line graph showing the cytotoxicity of SS-2-08 in WM164 cancer cell lines.
Figure 8:
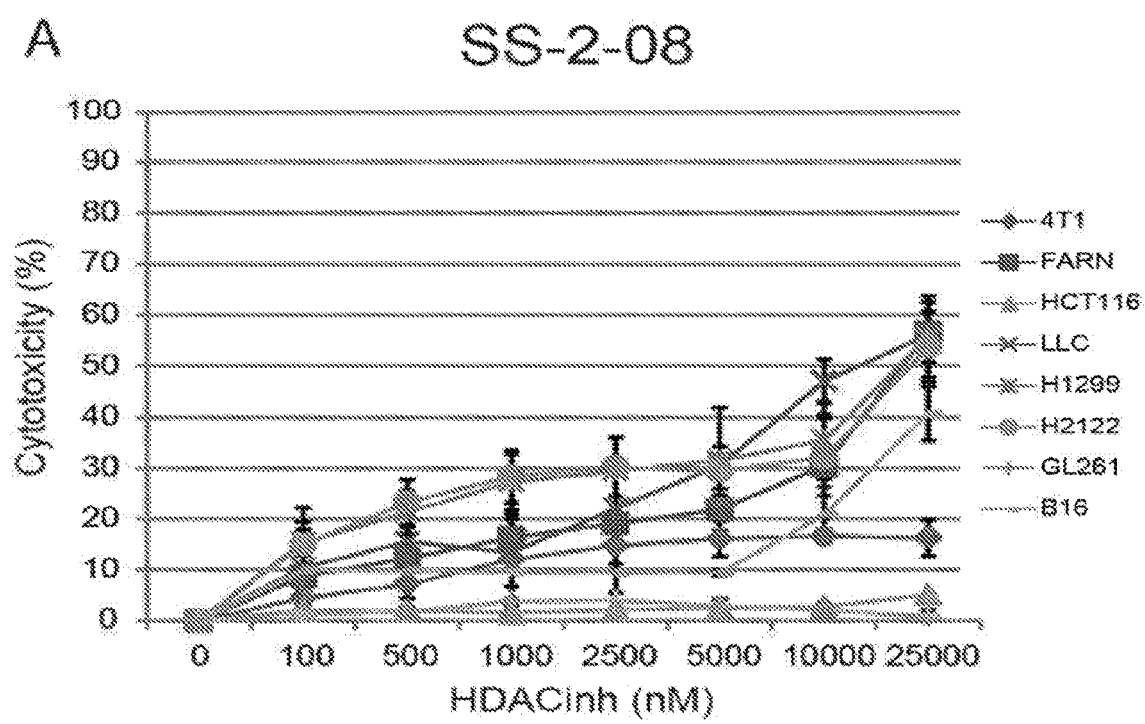
FIG. 8 is a line graph showing that SS-2-08 induces low cytotoxicity in a variety of cancer cell lines.

Human melanoma WM164 cells were treated with different concentrations SS-01-100 and SS-02-08 in the presence or absence of IL-6 (30 ng/uL) or IFNg (100 ng/uL). The levels of acetylated tubulin, a natural substrate for HDAC6, were increased in all the conditions tested. See FIGS. 1-3.

Example 14

Cell Culture

All cells were cultured in RPMI 1640 media, supplemented with 10% FBS, penicillin/streptomycin (50 U/ml), L-glutamine (2 mM), and 2-mercaptoethanol (50 μM) (complete media), and grown under humidified conditions at 37° C. and 5% $CO_2$.

Cytotoxicity Assay

Cells were plated at a desired density in a black, flat clear bottom, 96 well plate. After 24 hours of cell growth, the media was removed from all the wells, fresh media was added with the fluorescent CellTox dye, using the manufactured protocol. The plate was then treated with the compounds of interest at the various concentrations of the compound. Immediately after plating, a baseline reading was performed. The plate was then incubated for 24 hours before the next reading was done, which was considered the 24 hour reading. Assay measurements were collected using the SoftMax Pro Microplate Data Acquisition and Analysis Software paired with Molecular Devices spectrophotometer (SpectraMax).

HDAC Assay

Cells were plated at a density of 10,000 cells per/well overnight in a white, flat clear bottom 96 well plate. After 24 hours, the plate was then treated with the compounds of interest at the desired concentrations and incubated at 37° C. and 5% $CO_2$ for 1 hour. After incubation with the compounds, the developer is added to the substrate, mixed, and added directly to the plate, following the manufactured protocol.[6] Immediately after plating, the plate is read for an hour and 15 minutes with a reading done every 2 minutes, using the SpectraMax.

Human melanoma WM164 cells were treated with different concentrations SS-2-08 and SS-01-100 to evaluate the HDAC activity associated with the potential cytotoxic effect of these compounds. As shown in the FIGS. 4-7, both compounds reduced the HDAC activity in a dose-dependent manner while keeping minimal cytotoxicity effects in these cells.

Figure 9:
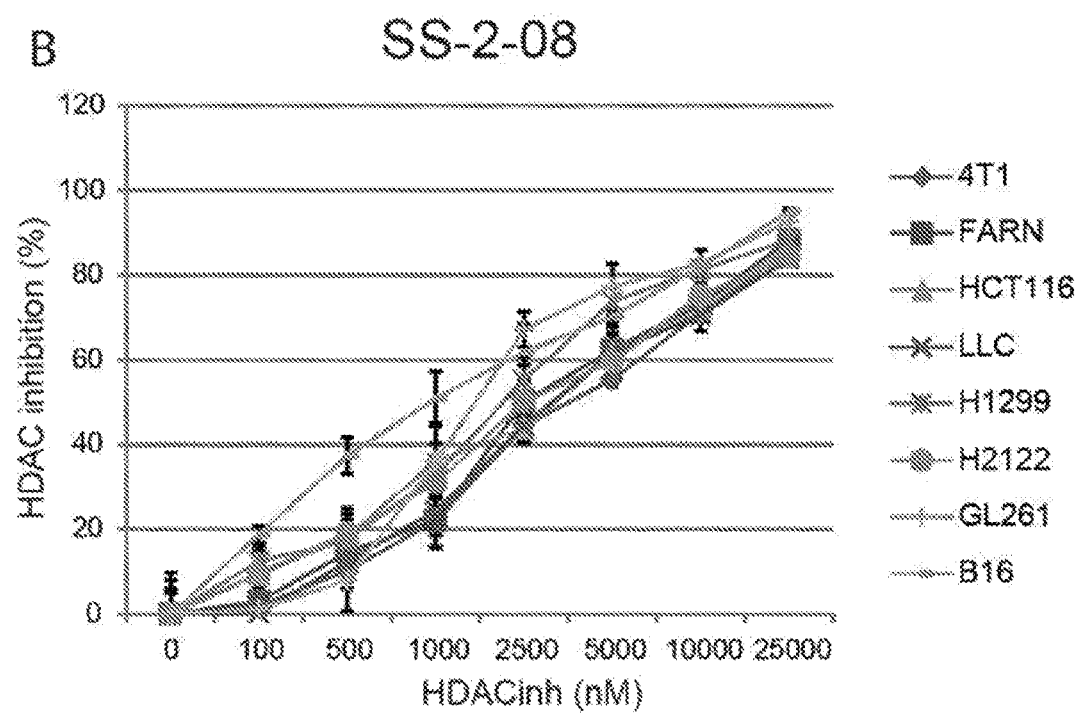
FIG. 9 is a line graph showing that SS-2-08 has HDAC activity in a variety of cancer cell lines.
Figure 10:
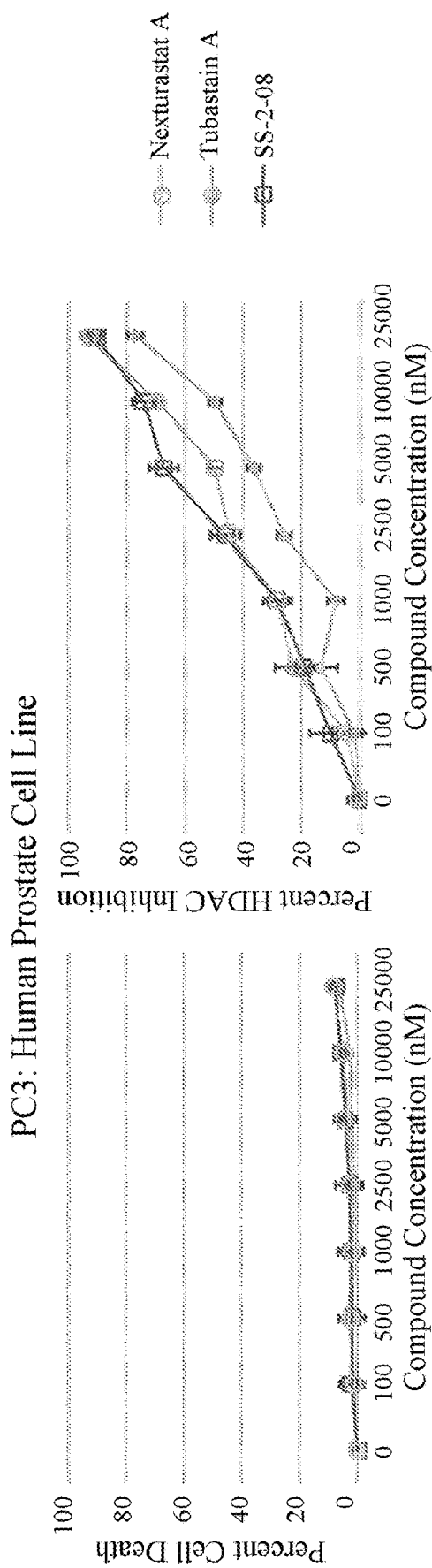
FIG. 10 contains two line graphs showing the activity (percent cell death and percent HDAC inhibition) of SS-2-08 in PC3 human prostate cell lines as compared to Nexturastat A and Tubastatin A.
Figure 11:
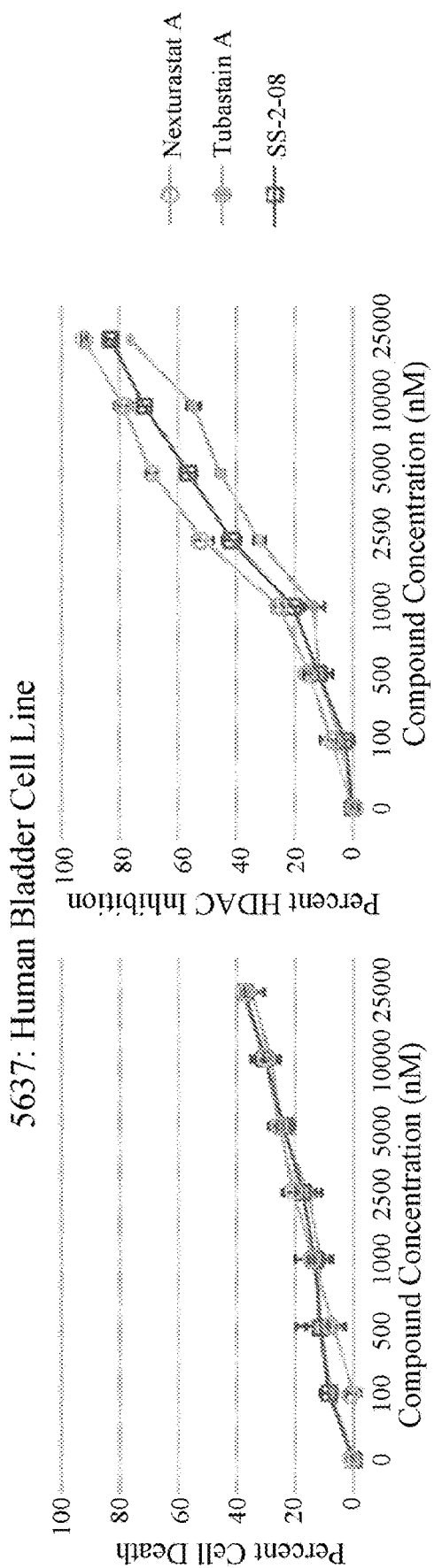
FIG. 11 contains two line graphs showing the activity (percent cell death and percent HDAC inhibition) of SS-2-08 in 5637 human bladder cells as compared to Nexturastat A and Tubastatin A.
Figure 12:
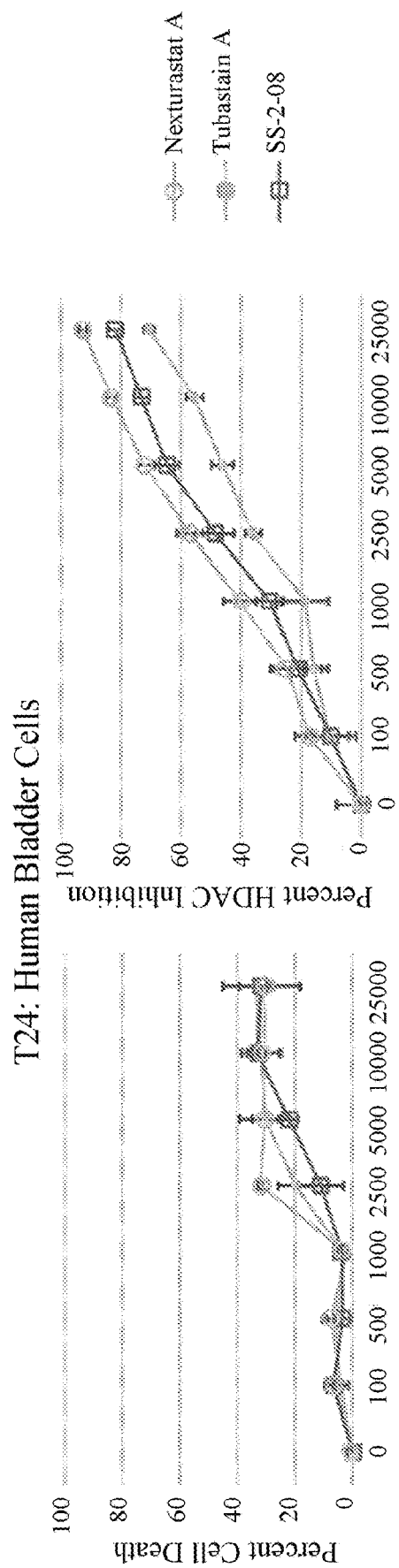
FIG. 12 contains two graphs showing the activity (percent cell death and percent HDAC inhibition) of SS-2-08 in T24 human bladder cells as compared to Nexturastat A and Tubastatin A.
Figure 13:
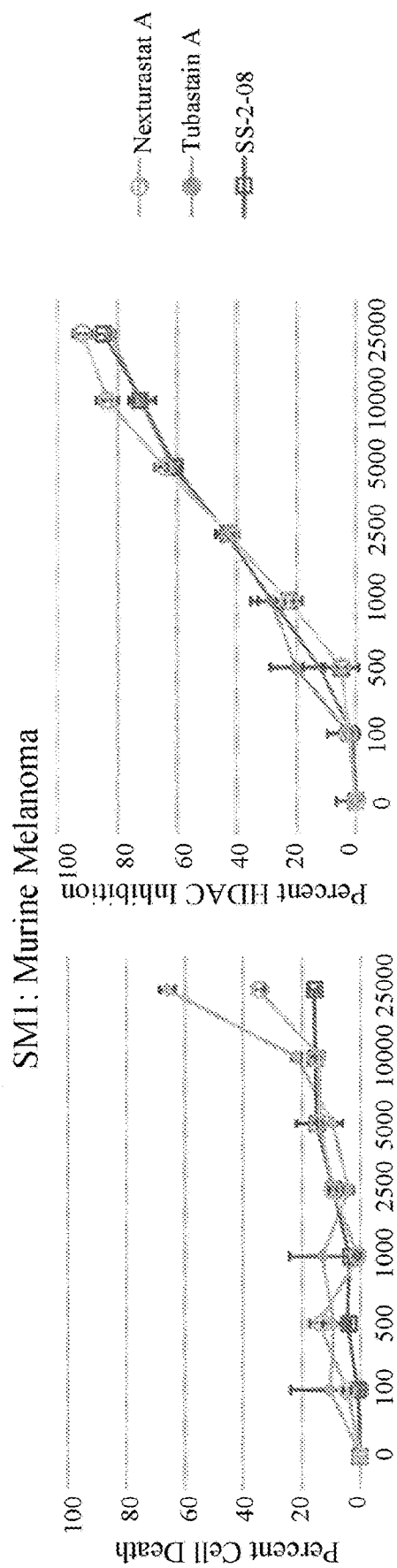
FIG. 13 contains two line graphs showing the activity (percent cell death and percent HDAC inhibition) of SS-2-08 in SM1 murine melanoma cells as compared to Nexturastat A and Tubastatin A.

Following the same experimental approach, the HDAC activity inhibition and cytotoxicity of SS-2-08 were evaluated in the human cells lines: HCT116, H1299, H2122 and murine: 4T1, FARN, LLC, GL261, B16. SS-2-08 reduced the HDAC activity in all tested cell lines. See FIG. 9. Additionally, the cytotoxicity of SS-2-08 was minimal up to 10 μM. See FIG. 9.

The cytotoxicity and HDAC activity inhibition of SS-2-08 was compared against the known HDAC6 inhibitors Nexturastat A and Tubastatin A in several cell lines. See FIGS. 10-13.

Example 15

Cell Culture

Murine melanoma SM1 cells were cultured in RPMI 1640 medium supplemented with: 1% minimum essential medium (MEM) non-essential amino acids solution, 10% fetal bovine serum (FBS), and 1% penicillin-streptomycin (P/S) then grown under humidified conditions at 37° C. and 5% $CO_2$.

ApoTox-Glo Triplex Assay® Controls

The assay controls—Digitonin (D141-100MG), Ionomycin (1064-1MG) and Mitomycin C (M4287-2MG)—were purchased from Sigma. Through a control plate evaluation, the optimal control concentration was selected for HDACi on the compound plates—30 μg/mL Digitonin, 100 μM Ionomycin, and 25 μg/mL Mitomycin.

ApoTox-Glo Triplex Assay®

Murine melanoma cells were treated with individual HDACi along with the protocol recommended assay controls. Following the manufacturers protocol, Viability/Cytotoxicity reagents were added—fluorescence was measured at one wavelength 400Ex/505Em (viability) and 485Ex/520Em (cytotoxicity). Next, the Caspase 3/7 reagent was added, after incubation, luminescence was measured at Lm578 (apoptosis). Assay measurements were collected using the SpectraMax. During analysis, LBH is used as the control compound.

Figure 14:
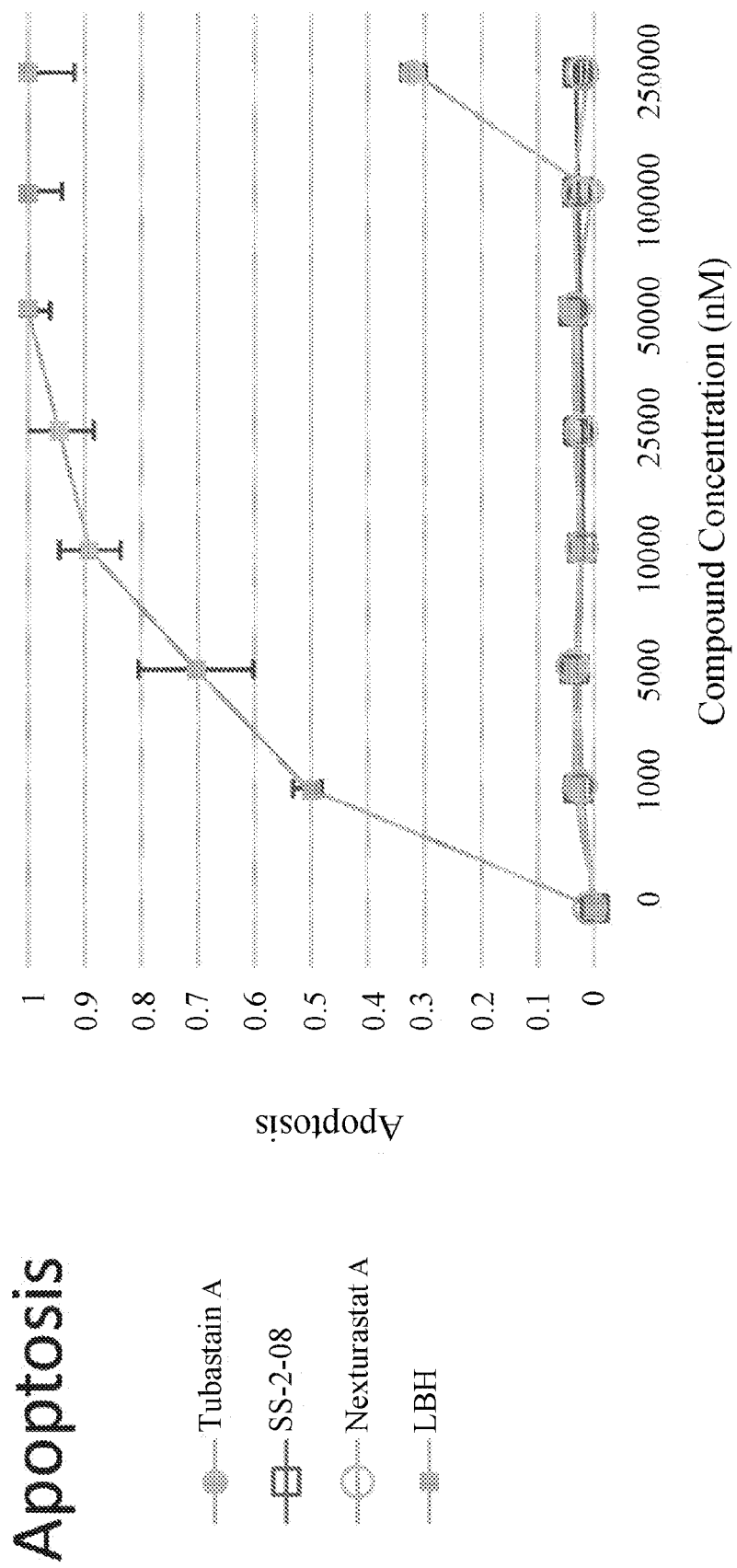
FIG. 14 is a line graph showing the apoptosis activity of SS-2-08, Nexturastat A, Tubastatin A, and LBH589 in melanoma cells.
Figure 15:
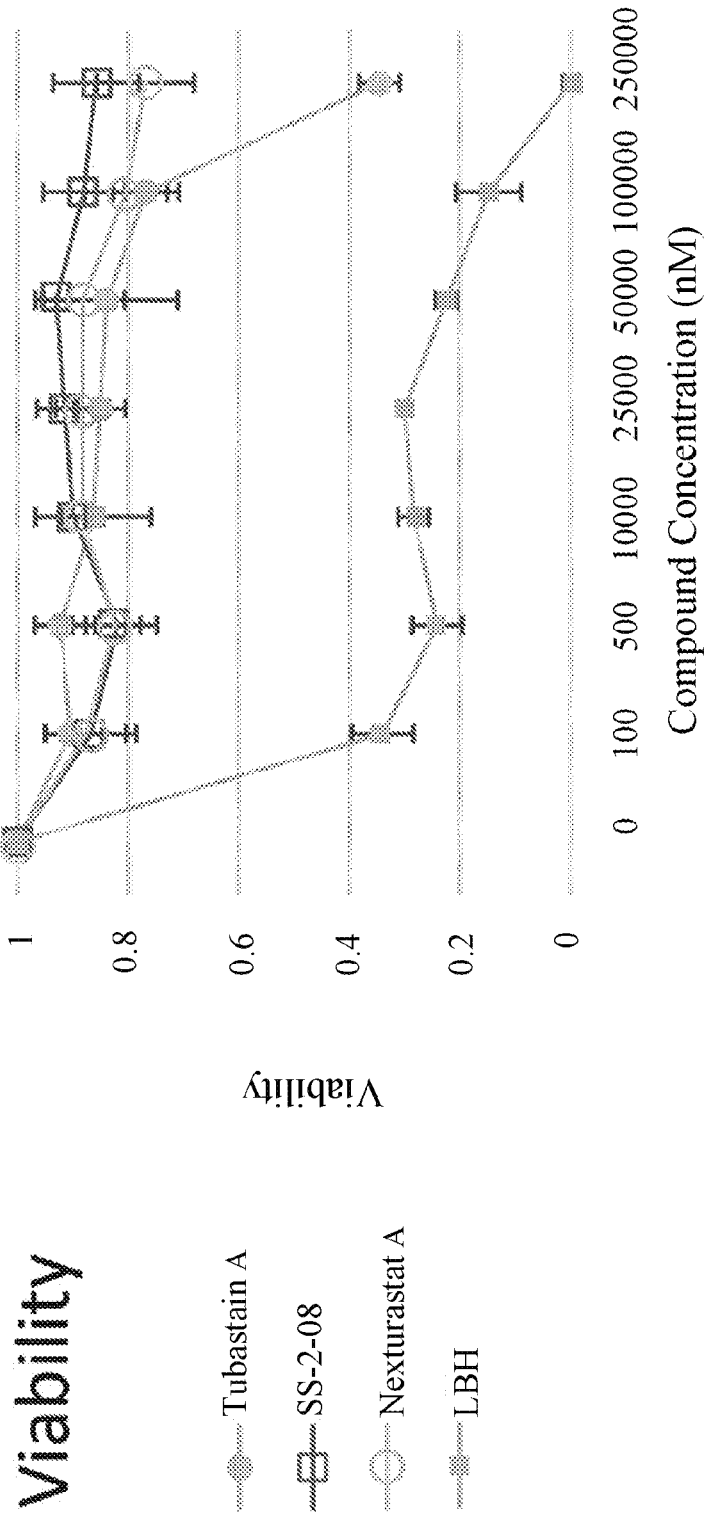
FIG. 15 is a line graph showing the viability of SS-2-08, Nexturastat A, Tubastatin A, and LBH589 in melanoma cells.
Figure 16:
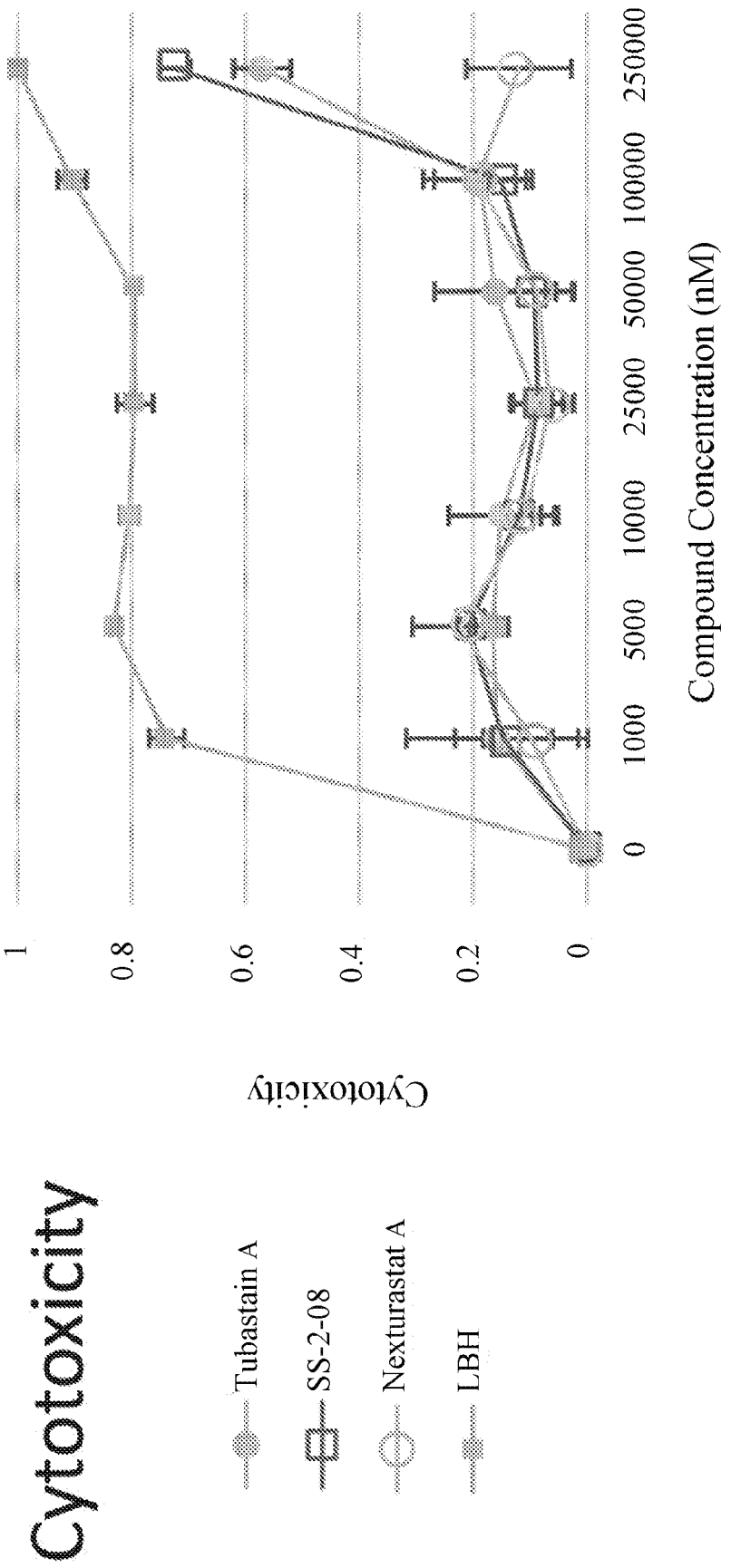
FIG. 16 is a line graph showing the cytotoxicity of SS-2-08, Nexturastat A, Tubastatin A, and LBH589 in melanoma cells.

SS-2-08 does not induce apoptosis in melanoma cells. Apoptosis, viability, and cytotoxicity were evaluated against the known HDAC6 inhibitors Nexturastat A and Tubastatin A, and the pan-HDAC inhibitor LBH589. See FIGS. 14-16.

Example 16

Study Design

Animal experiments involving mice were performed in accordance to all approved protocols by the IACUC at The George Washington University. C57/BL/6 mice were obtained from Charles River (Massachusetts-Wilmington, USA). Mice for the in vivo tumor studies were subcutaneously injected in the right flank with $1.0 \times 10^6$ SM1 melanoma cells suspended in 100 μL 1× Phosphate Buffer Saline (PBS). After subcutaneous injection, tumor growth was monitored until they became palpable. Once palpable (5-8 mm in diameter), the animals were then treated with a vehicle control, or SS-2-08 at a dose of 25 mg/kg and 50 mg/kg, intraperitoneally, three times a week. Tumor growth was recorded twice a week. When the tumors reached 4000 mm³, mice were euthanized. The values collected are represented as the mean tumor volume (mm³) and standard deviation for treatment groups.

Figure 17:
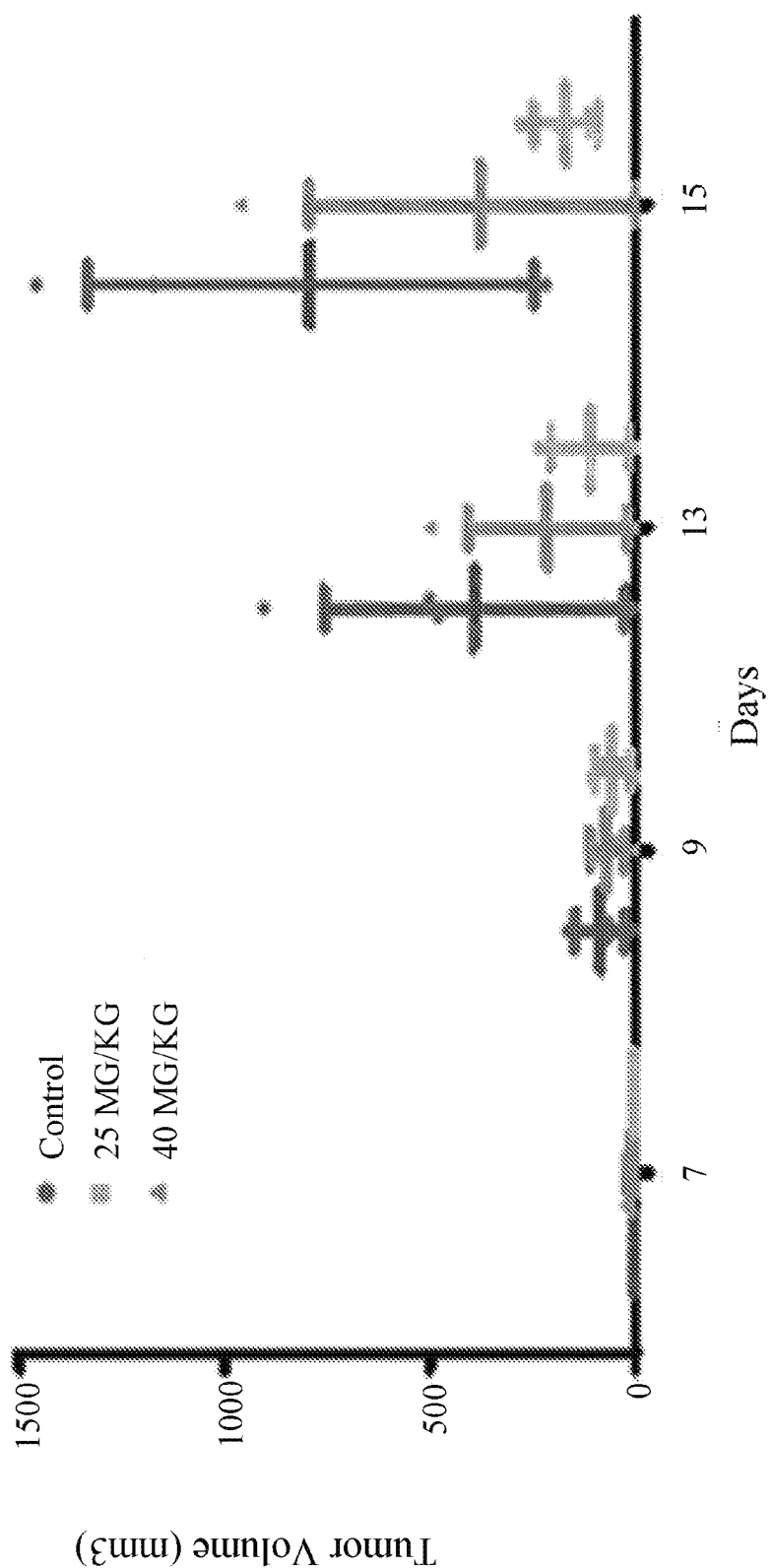
FIG. 17 is a graph showing that SS-2-08 reduces in vivo tumor growth in the syngeneic SM1 murine melanoma model.

SS-2-08 reduces tumor growth in syngeneic murine SM1 melanoma tumor as shown in FIG. 17.

All patents and publications cited herein are fully incorporated by reference in their entirety.

What is claimed is:

1. A method of eliminating, reducing, relieving, reversing, and/or ameliorating cancer in a subject in need thereof, the method comprising administering a therapeutically effective amount of a compound having Formula I:

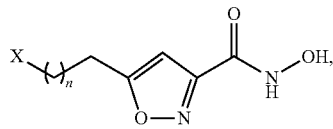

or a pharmaceutically acceptable salt, solvate, or prodrug thereof, to the subject; wherein:

X is selected from the group consisting of:

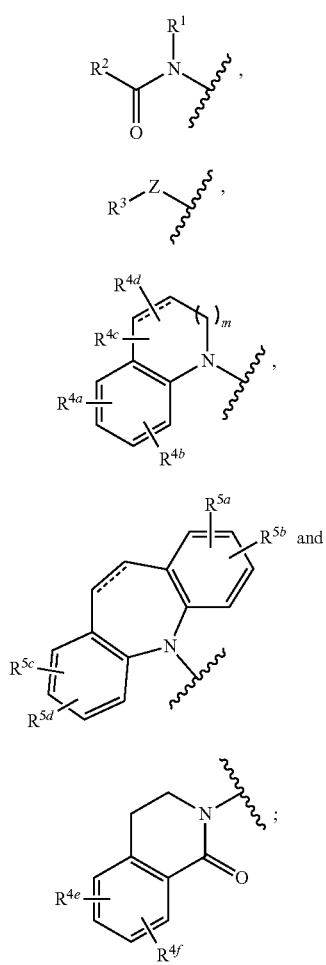

$R_1$ is selected from the group consisting of hydrogen and C1-4 alkyl;

$R^2$ is selected from the group consisting of optionally substituted $C_6$-$C_{14}$ aryl and aralkyl;

$R^3$ is selected from the group consisting of optionally substituted $C_6$-$C_{14}$ aryl, optionally substituted 5- to 14-membered heteroaryl, and —C(=O)NR$^d$R$^e$;

$R^{4a}$, $R^{4b}$, $R^{4c}$ and $R^{4f}$ are independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

$R^{4c}$ and $R^{4d}$ are independently selected from the group consisting of hydrogen and $C_{1-4}$ alkyl; or $R^{4c}$ and $R^{4d}$ taken together form a —C(=O)— with the carbon atom to which they are attached; $R^{5a}$, $R^{5b}$, $R^{5c}$, and $R^{5d}$ are independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, and haloalkoxy;

Z is selected from the group consisting of —O—, —N(R$^8$)—, and —C(=O)—; or

Z is absent;

$R^8$ is selected from the group consisting of hydrogen, $C_{1-4}$ alkyl, optionally substituted $C_{3-6}$ cycloalkyl, optionally substituted $C_6$-$C_{14}$ aryl, aralkyl, optionally substituted 5- to 14-membered heteroaryl, and heteroaralkyl;

m is 0, 1, or 2;

n is 1, 2, 3, 4, 5, or 6;

==== represents a single or double bond;

$R^a$, $R^b$, $R^d$, $R^e$ nd Re are independently selected from the group consisting of hydrogen, $C_{1-6}$ alkyl, optionally substituted $C_{3-6}$ cycloalkyl, optionally substituted $C_6$-$C_{14}$ aryl, and optionally substituted 5- to 14-membered heteroaryl; or $R^a$ and $R^b$ taken together with the nitrogen atom to which they are attached form an optionally substituted 3- to 12-membered heterocyclo; or $R^d$ and $R^e$ taken together with the nitrogen atom to which they are attached form an optionally substituted 3- to 12-membered heterocyclo; and $R^c$ is $C_{1-4}$ alkyl, with the proviso that when Z is absent, $R^3$ is a bicyclic or tricyclic $C_{10-14}$ aryl, a bicyclic or tricyclic 9- to 14-membered heteroaryl, or —C(=O)NR$^d$R$^e$.

2. The method of claim 1 further comprising administering a therapeutically effective amount of a second therapeutic agent.

3. The method of claim 2, wherein the second therapeutic agent is one or more of a chemotherapeutic agent, radiation, and an immunotherapy.

4. The method of claim 1, the method comprising administering a therapeutically effective amount of a compound having Formula II:

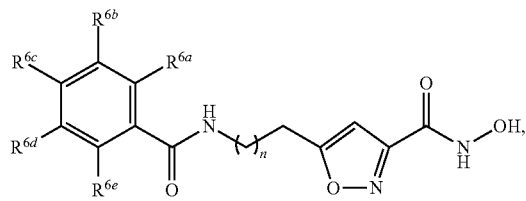

or a pharmaceutically acceptable salt, solvate, or prodrug thereof, wherein:

$R^{6a}$, $R^{6b}$, $R^{6c}$, $R^{6d}$, and $R^{6e}$ are each independently selected from the group consisting of hydrogen, halogen, hydroxy, nitro, cyano, —NR$^a$R$^b$, —C(=O)NR$^a$R$^b$, —C(=O)R$^c$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-6}$ cycloalkyl, optionally substituted phenyl, optionally substituted 5- or 6-membered heteroaryl, and optionally substituted 5- or 6-membered heterocyclo;

$R^a$ and $R^b$ are independently selected from the group consisting of hydrogen and $C_{1-4}$ alkyl; or R$^a$ and R$^b$ taken together with the nitrogen atom to which they are attached form a 3- to 10-membered heterocyclo;

R$^c$ is C$_{1-4}$ alkyl; and n is 1, 2, or 3.

5. The method of claim 4, wherein R$^{6a}$, R$^{6b}$, R$^{6c}$, R$^{6d}$, and R$^{6e}$ are each independently selected from the group consisting of hydrogen, halogen, hydroxy, nitro, cyano, —NR$^a$R$^b$, —C(=O)NR$^a$R$^b$, —C(=O)R$^c$, C$_{1-4}$ alkyl, C$_{1-4}$ alkoxy, and C$_{1-4}$ haloalkyl.

6. The method of claim 5, wherein R$^{6a}$, R$^{6b}$, R$^{6c}$, R$^{6d}$, and R$^{6e}$ are each independently selected from the group consisting of hydrogen, halogen, cyano, C$_{1-4}$ alkyl, and C$_{1-4}$ alkoxy.

7. The method of claim 1, the method comprising administering a therapeutically effective amount of a compound having Formula III:

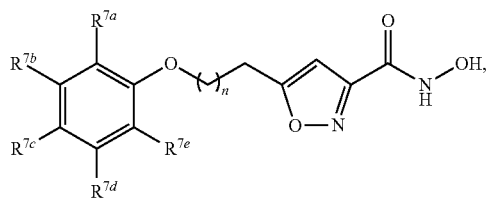

III or a pharmaceutically acceptable salt, solvate, or prodrug thereof, wherein:

R$^{7a}$, R$^{7b}$, R$^{7c}$, R$^{7d}$, and R$^{7e}$ are each independently selected from the group consisting of hydrogen, halogen, hydroxy, nitro, cyano, —NR$^a$R$^b$, —C(=O)NR$^a$R$^b$, —C(=O)R$^c$, C$_{1-6}$ alkyl, C$_{2-6}$ alkenyl, C$_{2-6}$ alkynyl, C$_{1-6}$ alkoxy, C$_{1-6}$ haloalkyl, haloalkoxy, optionally substituted C$_{3-6}$ cycloalkyl, optionally substituted phenyl, optionally substituted 5- or 6-membered heteroaryl, and optionally substituted 5- or 6-membered heterocyclo;

R$^a$ and R$^b$ are independently selected from the group consisting of hydrogen and C$_{1-4}$ alkyl; or R$^a$ and R$^b$ taken together with the nitrogen atom to which they are attached form a 3- to 10-membered heterocyclo;

R$^c$ is C$_{1-4}$ alkyl; and n is 1, 2, or 3.

8. The method of claim 7, wherein R$^{7a}$, R$^{7b}$, R$^{7c}$, R$^{7d}$, and R$^{7e}$ are each independently selected from the group consisting of hydrogen, halogen, hydroxy, nitro, cyano, —NR$^a$R$^b$, —C(=O)NR$^a$R$^b$, —C(=O)R$^c$, C$_{1-4}$ alkyl, C$_{1-4}$ alkoxy, and C$_{1-4}$ haloalkyl.

9. The method of claim 8, wherein lea, R$^{7a}$, R$^{7b}$, R$^{7c}$, R$^{7d}$, and R$^{7e}$ are each independently selected from the group consisting of hydrogen, halogen, cyano, C$_{1-4}$ alkyl, and C$_{1-4}$ alkoxy.

10. The method of claim 1, the method comprising administering a therapeutically effective amount of a compound having Formula IV:

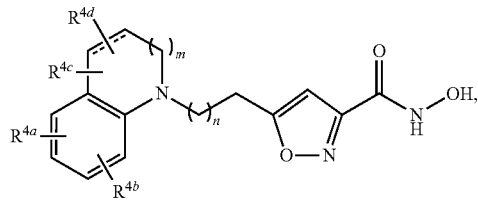

IV or a pharmaceutically acceptable salt, solvate, or prodrug thereof, wherein:

R$^{4a}$ and R$^{4b}$ are independently selected from the group consisting of hydrogen, halogen, cyano, C$_{1-4}$ alkyl, and C$_{1-4}$ alkoxy;

R$^{4c}$ and R$^{4d}$ are independently selected from the group consisting of hydrogen and methyl;

m is 0 or 1;

n is 1, 2, or 3; and

==== represents a single or double bond.

11. The method of claim 10, wherein m is 0 and ==== represents a double bond.

12. The method of claim 10, wherein m is 1 and ==== represents a single bond.

13. The method of claim 1, the method comprising administering a therapeutically effective amount of a compound having Formula V:

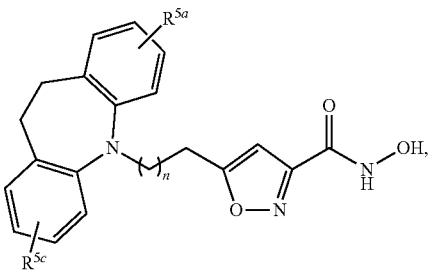

V or a pharmaceutically acceptable salt, solvate, or prodrug thereof, wherein:

R$^{5a}$ and R$^{5c}$ are independently selected from the group consisting of hydrogen, halogen, cyano, C$_{1-4}$ alkyl, and C$_{1-4}$ alkoxy; and n is 1, 2, or 3.

14. The method of claim 13, wherein n is 1 or 2.

15. The method of claim 1, the method comprising administering a therapeutically effective amount of a compound, or a pharmaceutically acceptable salt, solvate, or prodrug thereof, selected from the group consisting of:

5-(2-benzamidoethyl)-N-hydroxyisoxazole-3-carboxamide;

5-(2-(3,4-dichlorobenzamido)ethyl)-N-hydroxyisoxazole-3-carboxamide;

5-(2-(2-naphthamido)ethyl)-N-hydroxyisoxazole-3-carboxamide;

5-(2-([1,1'-biphenyl]-3-carboxamido)ethyl)-N-hydroxyisoxazole-3-carboxamide;

5-(4-(5,6-dichloro-1H-indol-1-yl)butyl)-N-hydroxyisoxazole-3-carboxamide;

5-(4-(6-chloro-3,4-dihydroquinolin-1(2H)-yl)butyl)-N-hydroxyisoxazole-3-carboxamide;

5-(4-(6-chloro-4,4-dimethyl-3,4-dihydroquinolin-1(2H)-yl)butyl)-N-hydroxyisoxazole-3-carboxamide;
5-(3-(3,4-dichlorophenoxy)propyl)-N-hydroxyisoxazole-3-carboxamide;
5-(4-(2,8-dichloro-10,11-dihydro-5H-dibenzo[b,f]azepin-5-yl)butyl)-N-hydroxyisoxazole-3-carboxamide;
5-(2-(4-bromobenzamido)ethyl)-N-hydroxyisoxazole-3-carboxamide;
5-(2-(4-fluorobenzamido)ethyl)-N-hydroxyisoxazole-3-carb oxamide;
5-(2-(4-chlorobenzamido)ethyl)-N-hydroxyisoxazole-3-carboxamide;
N-hydroxy-5-(2-(4-methoxybenzamido)ethyl)isoxazole-3-carboxamide;
5-(2-(4-(dimethylamino)benzamido)ethyl)-N-hydroxyisoxazole-3-carb oxamide;
5-(2-(4-cyclopropylbenzamido)ethyl)-N-hydroxyisoxazole-3-carboxamide;
5-(2-(3,4-difluorobenzamido)ethyl)-N-hydroxyisoxazole-3-carboxamide;
5-(2-(3-chloro-4-fluorobenzamido)ethyl)-N-hydroxyisoxazole-3-carb oxamide;
5-(2-(4-chloro-3-fluorobenzamido)ethyl)-N-hydroxyisoxazole-3-carb oxamide;
5-(2-(3-(dimethylamino)benzamido)ethyl)-N-hydroxyisoxazole-3-carb oxamide;
N-hydroxy-5-(2-(3-(pyridin-3-yl)benzamido)ethyl)isoxazole-3-carboxamide;
5-(3-benzamidopropyl)-N-hydroxyisoxazole-3-carb oxamide;
N-hydroxy-5-(2-(4-(trifluoromethoxy)benzamido)ethyl)isoxazole-3-carboxamide;
5-(2-((4,5-dichloroindoline-1-carboxamido)ethyl)-N-hydroxyisoxazole-3-carboxamide;
5-(2-((6,7-dichloroisoquinolin-3-yl)amino)ethyl)-N-hydroxyisoxazole-3-carboxamide;
5-(3-(5,6-dichloro-1H-benzo[d]imidazol-2-yl)propyl)-N-hydroxyisoxazole-3-carboxamide;
5-(2-((5,6-dichloro-1-methyl-1H-benzo[d]imidazol-2-yl)oxy)ethyl)-N-hydroxyisoxazole-3-carboxamide;
N-hydroxy-5-(2-(4-((trifluoromethyl)thio)benzamido)ethyl)isoxazole-3-carboxamide;
5-(4-(4,5-dichloroindolin-1-yl)-4-oxobutyl)-N-hydroxyisoxazole-3-carboxamide;
5-(2-((6,7-dichloroquinolin-2-yl)amino)ethyl)-N-hydroxyisoxazole-3-carboxamide;
5-(3-(5,6-dichlorobenzo[d]thiazol-2-yl)propyl)-N-hydroxyisoxazole-3-carboxamide;
5-(3-(5,6-dichlorobenzo[d]oxazol-2-yl)propyl)-N-hydroxyisoxazole-3-carboxamide;
N-hydroxy-5-(2-(4-(trifluoromethyl)benzamido)ethyl)isoxazole-3-carboxamide;
2-(3-(hydroxycarbamoyl)isoxazol-5-yl)ethyl-4,5-dichloroindoline-1-carboxylate;
5-(2-((6,7-dichloronaphthalen-2-yl)amino)ethyl)-N-hydroxyisoxazole-3-carboxamide;
5-(2-((5,6-dichlorobenzo[d]thiazol-2-yl)amino)ethyl)-N-hydroxyisoxazole-3-carboxamide;
N-hydroxy-5-(2-(phenanthridin-6-ylamino)ethyl)isoxazole-3-carboxamide;
5-(2-(2-(3,4-dichlorophenyl)acetamido)ethyl)-N-hydroxyisoxazole-3-carboxamide;
5-(2-(6,7-dichloro-1-oxo-3,4-dihydroisoquinolin-2(1H)-yl)ethyl)-N-hydroxyisoxazole-3-carboxamide;
5-(2-((5,6-dichloroisoquinolin-1-yl)amino)ethyl)-N-hydroxyisoxazole-3-carboxamide;
N-hydroxy-5-(2-(2-phenylacetamido)ethyl)isoxazole-3-carboxamide;
2-(3-(hydroxycarbamoyl)isoxazol-5-yl)ethyl(3,4-dichlorophenyl)(methyl)carbamate;
5-(2-((5,6-dichloroisoquinolin-1-yl)oxy)ethyl)-N-hydroxyisoxazole-3-carboxamide;
5-(2-(N-butylbenzamido)ethyl)-N-hydroxyisoxazole-3-carboxamide;
5-(4-((3,4-dichlorophenyl)amino)butyl)-N-hydroxyisoxazole-3-carboxamide;
5-(3-((3,4-dichlorophenyl)amino)propyl)-N-hydroxyisoxazole-3-carboxamide;
N-hydroxy-5-(3-(naphthalen-1-ylamino)propyl)isoxazole-3-carboxamide;
N-hydroxy-5-(3-(quinolin-8-ylamino)propyl)isoxazole-3-carboxamide;
5-(4-(8-chloro-2-methyl-1,2,3,4-tetrahydro-5H-pyrido[4,3-b]indol-5-yl)butyl)-N-hydroxyisoxazole-3-carboxamide;
5-(4-((4-chlorophenyl)(cyclohexyl)amino)butyl)-N-hydroxyisoxazole-3-carboxamide;
5-(4-(bis(4-chlorophenyl)amino)butyl)-N-hydroxyisoxazole-3-carboxamide;
5-(4-((4-chlorobenzyl)(4-chlorophenyl)amino)butyl)-N-hydroxyisoxazole-3-carboxamide;
N-hydroxy-5-(3-(naphthalen-1-yloxy)propyl)isoxazole-3-carboxamide; and
N-hydroxy-5-(3-(quinolin-8-yloxy)propyl)isoxazole-3-carboxamide.

* * * * *

UNITED STATES PATENT AND TRADEMARK OFFICE
CERTIFICATE OF CORRECTION

| | | |
|---|---|---|
| PATENT NO. | : 12,024,493 B2 | Page 1 of 1 |
| APPLICATION NO. | : 17/590503 | |
| DATED | : July 2, 2024 | |
| INVENTOR(S) | : Villagra et al. | |

It is certified that error appears in the above-identified patent and that said Letters Patent is hereby corrected as shown below:

In the Claims

In Column 103, Claim 1, Line 53, delete "C1-4" insert --$C_{1\text{-}4}$--, therefor.

In Column 104, Claim 1, Line 18, delete "$R^e$ nd Re" insert --and $R^e$--, therefor.

In Column 105, Claim 6, Line 14, delete "$R^{6c}$" insert --$R^{6e}$--, therefor.

In Column 105, Claim 9, Line 60, after "wherein" delete "lea,".

Signed and Sealed this
Nineteenth Day of November, 2024

Katherine Kelly Vidal
*Director of the United States Patent and Trademark Office*